(12) United States Patent
Anton et al.

US009206448B2

(10) Patent No.: US 9,206,448 B2
(45) Date of Patent: *Dec. 8, 2015

(54) EXTRACTION SOLVENTS DERIVED FROM OIL FOR ALCOHOL REMOVAL IN EXTRACTIVE FERMENTATION

(75) Inventors: Douglas Robert Anton, Wilmington, DE (US); Jelena Cirakovic, Wilmington, DE (US); Bruce A. Diner, Chadds Ford, PA (US); Michael Charles Grady, Oaklyn, NJ (US); Francis J. Woerner, Bear, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 625 days.

This patent is subject to a terminal disclaimer.

(21) Appl. No.: 13/162,828

(22) Filed: Jun. 17, 2011

(65) Prior Publication Data

US 2011/0312044 A1  Dec. 22, 2011

Related U.S. Application Data

(60) Provisional application No. 61/368,436, filed on Jul. 28, 2010, provisional application No. 61/356,290, filed on Jun. 18, 2010, provisional application No. 61/368,451, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.
| | |
|---|---|
| C12P 1/00 | (2006.01) |
| C12N 9/00 | (2006.01) |
| C12N 15/00 | (2006.01) |
| C12N 1/14 | (2006.01) |
| C07H 21/04 | (2006.01) |
| C12P 7/16 | (2006.01) |
| B01D 3/00 | (2006.01) |
| B01D 21/26 | (2006.01) |
| C07C 29/86 | (2006.01) |
| C11B 1/02 | (2006.01) |
| C11B 13/00 | (2006.01) |
| C12M 1/00 | (2006.01) |
| C12P 7/64 | (2006.01) |
| C12P 7/18 | (2006.01) |

(52) U.S. Cl.
CPC . *C12P 7/16* (2013.01); *B01D 3/002* (2013.01); *B01D 21/26* (2013.01); *C07C 29/86* (2013.01); *C11B 1/025* (2013.01); *C11B 13/00* (2013.01); *C12M 1/00* (2013.01); *C12M 21/12* (2013.01); *C12M 45/04* (2013.01); *C12M 45/09* (2013.01); *C12N 1/14* (2013.01); *C12N 15/00* (2013.01); *C12P 7/18* (2013.01); *C12P 7/6418* (2013.01); *B01D 21/262* (2013.01); *Y02E 50/10* (2013.01); *Y02E 50/16* (2013.01); *Y02E 50/17* (2013.01); *Y02W 30/74* (2015.05)

(58) Field of Classification Search
CPC .................................. C12N 1/14; C12P 7/16
See application file for complete search history.

(56) References Cited

U.S. PATENT DOCUMENTS

| | | | |
|---|---|---|---|
| 5,221,357 A | 6/1993 | Brink | |
| 6,646,146 B1 | 11/2003 | Sinnema et al. | |
| 7,851,188 B2 | 12/2010 | Donaldson et al. | |
| 7,932,063 B2 | 4/2011 | Dunson et al. | |
| 8,373,008 B2 | 2/2013 | Grady et al. | |
| 8,373,009 B2 | 2/2013 | Grady et al. | |
| 8,409,834 B2 * | 4/2013 | Burlew et al. | 435/155 |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2 * | 10/2013 | Burlew et al. | 435/41 |

(Continued)

FOREIGN PATENT DOCUMENTS

| | | |
|---|---|---|
| GB | 2146638 A | 4/1985 |
| JP | 1986192291 | 8/1986 |

(Continued)

OTHER PUBLICATIONS

Campos et al. Production of acetone butanol ethanol from degermed corn using Clostridium beijerinckii BA101. Appl Biochem Biotechnol. 2002 Spring;98-100:553-61.*

(Continued)

*Primary Examiner* — Yong Pak

(57) ABSTRACT

In an alcohol fermentation process, oil derived from biomass is chemically converted into an extractant available for in situ removal of a product alcohol such as butanol from a fermentation broth. The glycerides in the oil can be chemically converted into a reaction product, such as fatty acids, fatty alcohols, fatty amides, fatty acid methyl esters, fatty acid glycol esters, and hydroxylated triglycerides, and mixtures thereof, which forms a fermentation product extractant having a partition coefficient for a product alcohol greater than a partition coefficient of the oil of the biomass for the product alcohol. Oil derived from a feedstock of an alcohol fermentation process can be chemically converting into the fermentation product extractant. The oil can be separated from the feedstock prior to the feedstock being fed to a fermentation vessel, and the separated oil can be chemically converted to a fermentation product extractant, which can then contacted with a fermentation product comprising a product alcohol, whereby the product alcohol is separated from the fermentation product.

14 Claims, 5 Drawing Sheets

(56) References Cited

U.S. PATENT DOCUMENTS

Figure 1:
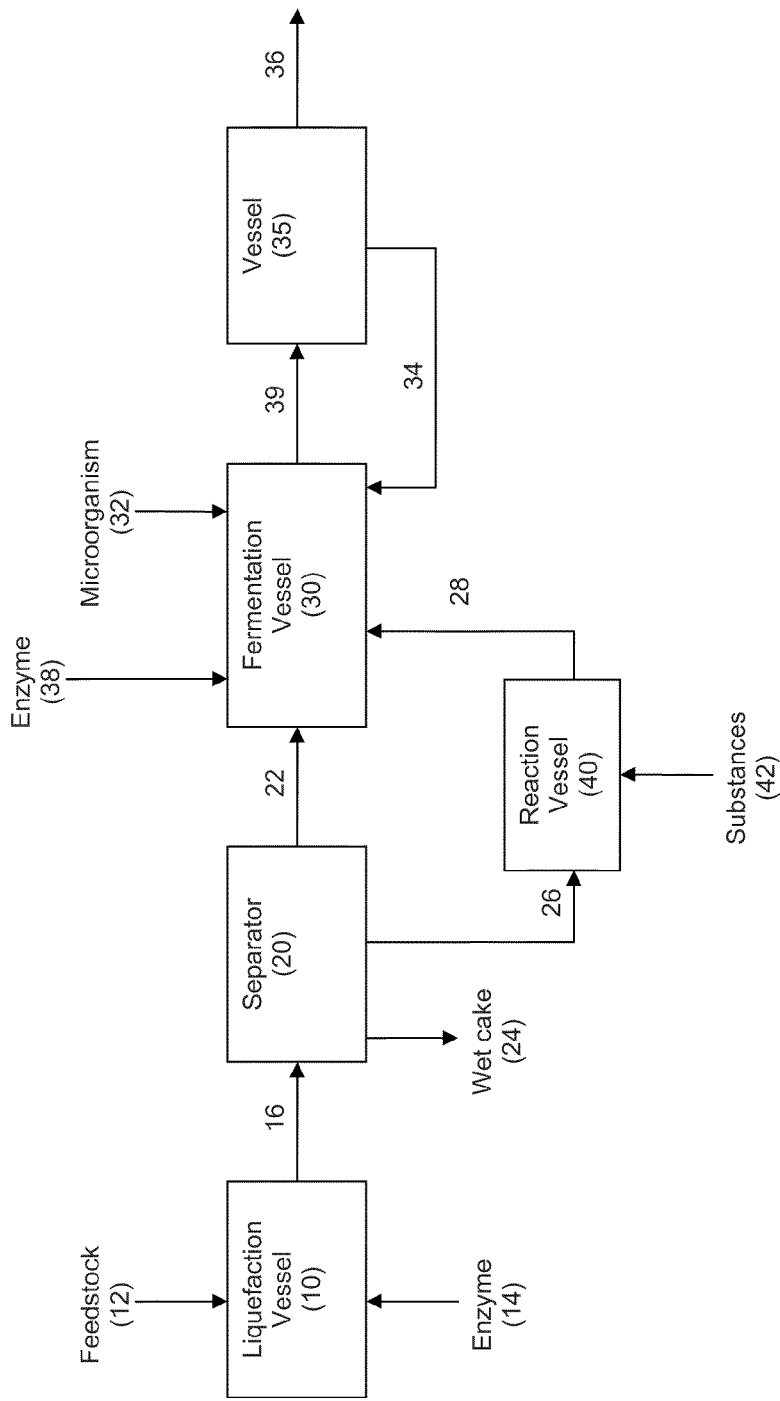

| | | |
|---|---|---|
| 8,563,788 B2 | 10/2013 | Grady et al. |
| 8,569,552 B2 | 10/2013 | Grady et al. |
| 8,574,406 B2 | 11/2013 | Grady et al. |
| 8,617,861 B2 | 12/2013 | Grady et al. |
| 8,628,643 B2 | 1/2014 | Grady et al. |
| 8,697,404 B2 | 4/2014 | Anton et al. |
| 8,759,044 B2 | 6/2014 | DiCosimo et al. |
| 8,765,425 B2 | 7/2014 | DiCosimo et al. |
| 8,906,204 B2 | 12/2014 | Xu |
| 8,968,522 B2 | 3/2015 | Xu et al. |
| 8,968,523 B2 | 3/2015 | Xu et al. |
| 2007/0014905 A1 | 1/2007 | Chen et al. |
| 2007/0031918 A1 | 2/2007 | Dunson et al. |
| 2007/0077635 A1 | 4/2007 | Brunner et al. |
| 2008/0176298 A1 | 7/2008 | Randhava et al. |
| 2008/0182308 A1 | 7/2008 | Donaldson et al. |
| 2008/0274526 A1 | 11/2008 | Bramucci et al. |
| 2009/0017164 A1 | 1/2009 | Schisler et al. |
| 2009/0163376 A1 | 6/2009 | Li et al. |
| 2009/0171129 A1 | 7/2009 | Evanko et al. |
| 2009/0181153 A1 | 7/2009 | Bendorf et al. |
| 2009/0269823 A1 | 10/2009 | Bramucci et al. |
| 2009/0305363 A1 | 12/2009 | Anthony |
| 2009/0305370 A1 | 12/2009 | Grady |
| 2010/0081154 A1 | 4/2010 | Flint et al. |
| 2010/0092603 A1 | 4/2010 | Bruinsma et al. |
| 2010/0124773 A1 | 5/2010 | Yang |
| 2010/0143995 A1 | 6/2010 | Erdner-Tindall et al. |
| 2010/0159551 A1 | 6/2010 | Redford |
| 2011/0008863 A1 | 1/2011 | Zhu et al. |
| 2011/0097773 A1 | 4/2011 | Grady et al. |
| 2011/0124060 A1 | 5/2011 | Anthony et al. |
| 2011/0136193 A1 | 6/2011 | Grady et al. |
| 2011/0244536 A1 | 10/2011 | Nagarajan et al. |
| 2011/0294179 A1 | 12/2011 | Grady et al. |
| 2011/0312053 A1 | 12/2011 | Burlew et al. |
| 2012/0015416 A1 | 1/2012 | Anthony et al. |
| 2012/0156738 A1 | 6/2012 | Anton et al. |
| 2012/0208246 A1 | 8/2012 | Anton et al. |
| 2012/0323047 A1 | 12/2012 | Dauner et al. |
| 2013/0164795 A1 | 6/2013 | Lowe et al. |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0295661 A1 | 11/2013 | Roesch et al. |
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |
| 2014/0256020 A1 | 9/2014 | DiCosimo et al. |
| 2014/0273127 A1 | 9/2014 | Fuchs et al. |
| 2014/0273130 A1 | 9/2014 | Anthony et al. |
| 2014/0303408 A1 | 10/2014 | Zaher et al. |
| 2014/0311889 A1 | 10/2014 | Zaher et al. |
| 2014/0363865 A1 | 12/2014 | Burlew et al. |
| 2015/0010975 A1 | 1/2015 | Burlew et al. |
| 2015/0010984 A1 | 1/2015 | Bhalla et al. |
| 2015/0060259 A1 | 3/2015 | Xu |

FOREIGN PATENT DOCUMENTS

| | | |
|---|---|---|
| WO | WO2009015333 | 1/2009 |
| WO | WO2009026706 | 3/2009 |
| WO | 2009149270 A2 | 12/2009 |
| WO | 2010049491 A1 | 5/2010 |
| WO | WO2010059919 | 5/2010 |
| WO | 2010119339 A2 | 10/2010 |
| WO | 2011063402 A2 | 5/2011 |
| WO | WO2012036857 | 3/2012 |

OTHER PUBLICATIONS

Ishizaki et al. Extractive acetone-butanol-ethanol fermentation using methylated crude palm oil as extractant in batch culture of Clostridium saccharoperbutylacetonicum N1-4 (ATCC 13564). J Biosci Bioeng. 1999;87(3):352-6.*

Ezeji et al. Butanol fermentation research: upstream and downstream manipulations. Chem Rec. 2004;4(5):305-14.*

Akada et al., PCR-mediated seamless gene deletion and marker recycling in saccharomyces cerevisiae, Yeast, 2006, pp. 399-405, vol. 23.

Bellion et al., Microb. Growth C1 Compd., [Int. Symp.], 7th (1993), pp. 415-432, Editor(s): Murrell, J. Collin; Kelly, Don P. Publisher: Intercept, Andover, UK.

Horton et al., Engineering hybrid genes without the use of restriction enzymes: gene splicing by overlap extension, Gene, 1989, pp. 61-68, vol. 77.

Kohlhase et al., Catalytic Effects in the Ammonolysis of Vegetable Oils, The Journal of the American Oil Chemists' Society, 1971, pp. 265-270, vol. 48.

Lynd et al., Microbial Cellulose Utilization: Fundamentals of Biotechnology, Microbiology and Molecular Biology Reviews, Sep. 2002, pp. 506-577, vol. 66, No. 3.

Ma et al., Plasmid construction by homologous recombination in yeast, Gene, 1987, pp. 201-216, vol. 58.

Malinowski, Two-phase partitioning bioreactors in fermentation technology, Biotechnology Advances, 2001, pp. 525-538, vol. 19.

Methods in Yeast Genetics, 2005, Cold Spring Harbor Laboratory Press, Cold Spring Harbor, NY, pp. 201-202.

Oudshoorn et al., Assessment of Options for Selective 1-Butanol Recovery from Aqueous Solution, Industrial and Engineering Chemistry Research, 2009, pp. 7325-7336, vol. 48.

Roe et al., Fatty Acid Amides. IV. Reaction of Fats With Ammonia and Amines, The Journal of the American Oil Chemists' Society, Jan. 1952, pp. 18-22, vol. 29.

Roffler, Steve Ronald: Extractive fermentation—lactic acid and acetone/butanol production, 1986, pp. 1-289, PhD. Dissertation in Chemical Engineering, University of California, Berkeley.

Sulter et al., Proliferation and metabolic significance of peroxisomes in candida boidinii during growth on D-alanine or oleic acid as the sole carbon source, Archives of Microbiology,1990, pp. 485-489, vol. 153, No. 9.

Wach et al., New heterologous modules for classical or PCR-based gene disruptions in saccharomyces cerevisiae, Yeast, 1994, pp. 1793-1808, vol. 10.

U.S. Appl. No. 12/980,607, filed Dec. 29, 2010.
U.S. Appl. No. 13/162,631, filed Jun. 17, 2011.
U.S. Appl. No. 13/162,643, filed Jun. 17, 2011.
U.S. Appl. No. 13/163,243, filed Jun. 17, 2011.

International Search Report and Written Opinion dated Oct. 10, 2011, International Application No. PCT/US2011/040842.

Ban et al., Whole cell biocatalyst for biodiesel fuel production utilizing Rhizopus oryzae cells immobilized within biomass support particles, Biochemical Engineering Journal, 2001, pp. 39-43, vol. 8.

Barros et al., Integration of Enzyme Catalysis in an Extraction Fermentation Process, Studies in Organic Chemistry 29, 1986.

Bligh et al., A Rapid Method of Total Lipid Extraction and Purification, Canadian Journal of Biochemistry and Physiology, Aug. 1959, pp. 911-917, vol. 37, No. 8.

Gupta et al., Bacterial lipases: an overview of production, purification and biochemical properties, Applied Microbiology and Biotechnology, 2004, pp. 763-781, vol. 64.

Kim et al., Extractive Recovery of Products from Fermentation Broths, Biotechnology and Bioprocess Engineering, 1999, 4:1-11.

Oliveira et al., Production and Extractive Biocatalysis of Ethanol Using Microencapsulated Yeast Cells and Lipase System, Journal of Chemical Technology and Biotechnology, 1991, 52:219-225.

(56) References Cited

OTHER PUBLICATIONS

Oliveira et al., Immobilization of Saccharomyces cerevisiae Cells and Rhizomucor miehi Lipase for the Production and Extractive Biocatalysis of Ethanol, Bioprocess Engineering, 1997, 16:349-353.

Oliveira et al., Improvement of Alcoholic Fermentations by Simultaneous Extraction and Enzymatic Esterification of Ethanol, Journal of Molecular Catalysis B: Enzymatic, 1998, 5:29-33.

Oliveira et al., Effect of extraction and Enzymatic Esterification of Ethanol on Glucose Consumption by Two Saccharomyces cerevisiae Strains: A comparative study, Journal of Chemical Technology and Biotechnology, 2001, 76:285-290.

Yoo et al., Enzymatic Synthesis of Sugar Fatty Acid Esters, Journal of Industrial Engineering Chemistry, 2007, pp. 1-5, vol. 13, No. 1.

U.S. Appl. No. 13/193,147, filed Jul. 28, 2011.

U.S. Appl. No. 14/415,928, filed Jan. 20, 2015 (Butamax).

U.S. Appl. No. 14/428,731, filed Mar. 20, 2015 (Butamax).

* cited by examiner

EXTRACTION SOLVENTS DERIVED FROM OIL FOR ALCOHOL REMOVAL IN EXTRACTIVE FERMENTATION

This application claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on July 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates the production of fermentative alcohols such as butanol and in particular, to extraction solvents for extractive fermentation, and processes for converting oil derived from biomass into the extraction solvents.

BACKGROUND OF THE INVENTION

Butanol is an important industrial chemical with a variety of applications including use as a fuel additive, as a feedstock chemical in the plastics industry, and as a food-grade extractant in the food and flavor industry. Accordingly, there is a high demand for butanol as well as for efficient and environmentally friendly production methods.

Production of butanol utilizing fermentation by microorganisms is one environmentally friendly production method. Some microorganisms that produce butanol in high yields also have low butanol toxicity thresholds, such that butanol needs to be removed from the fermentation vessel as it is being produced. In situ product removal (ISPR) (also referred to as extractive fermentation) removes butanol from the fermentation vessel as it is produced, thereby allowing the microorganism to produce butanol at high yields. One method for ISPR that has been described in the art is liquid-liquid extraction (U.S. Patent Application Publication No. 2009/0305370). In order to be technically and economically viable, ideally, liquid-liquid extraction calls for good contact between the extractant and the fermentation broth for efficient mass transfer of the product alcohol into the extractant; good phase separation of the extractant from the fermentation broth (during and after fermentation); efficient recovery and recycle of the extractant; minimal degradation of the capacity of the extractant to extract the product alcohol (by, e.g., preventing the lowering of the partition coefficient for the product alcohol into the extractant) and contamination of the extractant by lipids that lower the partition coefficient over a long-term operation.

In particular, the extractant can become contaminated with lipid over time with each recycle, for example, by the build-up of lipids present in the biomass that is fed to the fermentation vessel as feedstock of hydrolysable starch. As an example, a liquified corn mash loaded to a fermentation vessel at 30 wt % dry corn solids can result in a fermentation broth that contains about 1.2 wt % corn oil during conversion of glucose to butanol by simultaneous saccharification and fermentation (SSF) (with saccharification of the liquified mash occurring during fermentation by the addition of glucoamylase to produce glucose). The dissolution of the corn oil lipids in oleyl alcohol (OA) serving as an extractant during ISPR can result in build-up of lipid concentration with each OA recycle, decreasing the partition coefficient for the product alcohol in OA as the lipid concentration in OA increases with each recycle of OA.

In addition, the presence of the undissolved solids during extractive fermentation can negatively affect the efficiency of the alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids ultimately removed as Dried Distillers' Grains with Solubles (DDGS), slow the disengagement of extractant drops from the fermentation broth, and/or result in a lower fermentation vessel volume efficiency.

Several approaches for reducing the degradation of the partition coefficient of the extractant used in extractive fermentation have included wet milling, fractionation, and removal of solids. Wet milling is an expensive, multi-step process that separates a biomass (e.g., corn) into all of its key components (germ, pericarp fiber, starch, and gluten) in order to capture value from each co-product separately. This process gives a purified starch stream; however, it is costly and includes the separation of the biomass into its non-starch components, which is unnecessary for fermentative alcohol production. Fractionation removes fiber and germ, which contains a majority of the lipids present in ground whole corn, resulting in corn that has a higher starch (endosperm) content. Dry fractionation does not separate the germ and fiber, and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids, including germ containing lipids, from liquified mash prior to use in fermentation can substantially eliminate undissolved solids, as described for example in co-pending, commonly owned U.S. Provisional Patent Application No. 61/356,290, filed Jun. 18, 2010. However, it would be advantageous if the degradation of the partition coefficient of the extractant can be reduced even without fractionation or removal of undissolved solids. Thus, there is a continuing need to develop more efficient methods and systems for producing product alcohols such as butanol, through extractive fermentation in which the degradation of the partition coefficient of the extractant is reduced.

Moreover, the extractant (e.g., oleyl alcohol) is typically added to the process, rather than produced at a step in the process and therefore, the extractant is a raw material expense. Since the extractant can be lost to adsorption on non-fermentable solids and diluted with lipids introduced into the process, the economy of the alcohol production process can be affected by the efficiency of the extractant recovery and recycle. Thus, there exists a continuing need for alternative extractants for ISPR that can result in a more economical process by reducing capital and/or operating costs.

BRIEF SUMMARY OF THE INVENTION

The present invention satisfies the above needs by providing methods for producing product alcohols, such as butanol, in which the lipids in a biomass are converted into an extractant that can be used in ISPR, and in which the amount of lipids that are fed to the fermentation vessel, with the feedstock and/or upon extractant recycle, are decreased. The present invention provides further related advantages, as will be made apparent by the description of the embodiments that follow.

Chemical conversion of lipids derived from biomass to extractants including fatty acids, fatty alcohols, fatty amides, fatty acid esters, fatty acid glycol esters, and triglycerides, and mixtures thereof (collectively referred to herein as "fatty acid extractants") can decrease the amount of lipids present in the ISPR extractant. The triglycerides may be hydroxylated or alkoxylated (e.g., methoxylated, ethoxylated). Fatty acid extractants would not be expected to decrease the partition coefficient of the product alcohol, such as isobutanol, into the extractant phase as much as lipids. Moreover, the fatty acid extractants can be used as the ISPR extractant. The fatty acid extractants can be derived from the biomass supplying fermentable carbon fed to the fermentation vessel. The fatty acid extractants can therefore be produced at a step in the alcohol production process and be used in place of, or in addition to, a supplied, exogenous ISPR extractant that is not produced in the process (such as externally supplied oleyl alcohol), thereby reducing or even eliminating the raw material expense for the ISPR extractant.

In addition, extractants may also be produced by converting oil derived from biomass or feedstock into fatty acids using high temperature and/or high pressure conditions. Furthermore, oil derived from biomass or feedstock may be treated with one or more lipases to produce fatty acids or subjected to hydrogenation to produce fatty alcohols.

The present invention is directed to a composition comprising a recombinant microorganism capable of producing alcohol from a feedstock; alcohol; and at least one extractant selected from the group consisting of fatty acid, fatty alcohol, fatty amide, fatty ester, triglycerides, and mixtures thereof; wherein the extractant is produced from the feedstock. In one embodiment, the extractant is a mixture of fatty amides, and in a further embodiment, the mixture of fatty amides comprises linoleamide, oleamide, palmitamide, or stearamide. In another embodiment, the extractant is a mixture of fatty amides and fatty acids, and in a further embodiment, the mixture of fatty amides and fatty acids comprises linoleamide, linoleic acid, oleamide, oleic acid, palmitamide, palmitic acid, stearamide, or stearic acid. In one embodiment, the extractant is selected from hydroxylated triglycerides, alkoxylated triglycerides, hydroxylated fatty acids, alkoxylated fatty acids, hydroxylated fatty alcohols, and alkoxylated fatty alcohols. In one embodiment, the triglycerides may be methoxylated or ethoxylated. In another embodiment, the extractant is selected from saturated fatty acids, unsaturated fatty acids, saturated fatty alcohols, unsaturated fatty alcohols, saturated fatty amides, unsaturated fatty amides, saturated fatty esters, unsaturated fatty esters, and mixtures thereof. In one embodiment, the extractant may be a liquid or solid. In a further embodiment, the extractant may be in the form of beads. In one embodiment, the alcohol is $C_1$ to $C_8$ alkyl alcohols. In another embodiment, the feedstock comprises rye, wheat, corn, cane, barley, cellulosic material, lignocellulosic material, or mixtures thereof.

In one embodiment, the extractant comprises one or more fatty amides of the formula $R(C=O)N(R')(R'')$, wherein
R is independently selected from the group consisting of $C_3$ to $C_{27}$ alkyl groups optionally interrupted with one or more double bonds, and
R' and R" are independently selected from the group consisting of hydrogen and $C_1$-$C_6$ alkyl groups optionally containing one or more hydroxyl groups.

In another embodiment, the extractant comprises one or more fatty esters of the formula $R—(C=O)—OCHR'CHR''—OH$, wherein
R is independently selected from the group consisting of $C_3$ to $C_{27}$ alkyl groups optionally interrupted with one or more double bonds, and
R' and R" are independently selected from the group consisting of hydrogen and $C_1$-$C_4$ alkyl groups.

In one embodiment, the extractant comprises one or more fatty esters of the formula $R—(C=O)—OR'$, wherein
R is independently selected from the group consisting of $C_3$ to $C_{27}$ alkyl groups optionally interrupted with one or more double bonds, and
R' is an alkyl group of 8 carbons or less.

The present invention is directed to a method for producing an extractant comprising providing a biomass comprising oil; contacting the oil with one or more substances capable of chemically converting the oil into an extractant selected from the group consisting of fatty acids, fatty alcohols, fatty amides, fatty esters, triglycerides, and mixtures thereof, whereby at least a portion of the oil is converted to the extractant. In one embodiment, the triglycerides may be hydroxylated or alkoxylated (e.g., methoxylated, ethoxylated). In one embodiment, the extractant may be a liquid or solid. In a further embodiment, the extractant may be in the form of beads. In one embodiment, the method further comprises the step of separating the oil from the biomass prior to contacting the oil with the one or more substances. In one embodiment, the one or more substances is selected from aqueous ammonium hydroxide, anhydrous ammonia, ammonium acetate, ammonia in water, hydrogen peroxide, toluene, glacial acetic acid, lipase, and cation exchange resin. In another embodiment, the extractant has a partition coefficient for a product alcohol greater than the partition coefficient of the oil for the product alcohol prior to the oil being converted to extractant. In one embodiment, the product alcohol is $C_1$ to $C_8$ alkyl alcohols. In another embodiment, the biomass comprises corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, or mixtures thereof.

The present invention is also directed to a method for producing a product alcohol comprising: (a) providing biomass comprising oligosaccharides and oil; (b) contacting the biomass with a saccharification enzyme capable of converting oligosaccharides into monosaccharides; (c) separating the oil from the biomass of (a) or (b); (d) contacting the separated oil with one or more reactants or solvents to form an extractant; (e) contacting the biomass with a fermentation broth comprising a recombinant microorganism capable of converting the monosaccharides to a product alcohol and whereby a product alcohol is produced; and (f) contacting the product alcohol with the extractant, wherein the extractant has a partition coefficient for the product alcohol that is greater than the partition coefficient of the oil of the biomass for the product alcohol. In one embodiment, the one or more reactants or solvents is selected from aqueous ammonium hydroxide, anhydrous ammonia, ammonium acetate, ammonia in water, hydrogen peroxide, toluene, glacial acetic acid, lipase, and cation exchange resin. In one embodiment, the extractant is selected from fatty acid, fatty alcohol, fatty amide, fatty ester, triglycerides, and mixtures thereof. In one embodiment, the extractant is selected from hydroxylated triglycerides, alkoxylated triglycerides (e.g., methoxylated, ethoxylated), hydroxylated fatty acids, alkoxylated fatty acids, hydroxylated fatty alcohols, and alkoxylated fatty alcohols. In another embodiment, the extractant is selected from saturated fatty acids, unsaturated fatty acids, saturated fatty alcohols, unsaturated fatty alcohols, saturated fatty amides, unsaturated fatty amides, saturated fatty esters, unsaturated fatty esters, and mixtures thereof. In one embodiment, the extractant may be a liquid or solid. In a further embodiment, the extractant may be in the form of beads. In one embodiment, the alcohol is $C_1$ to $C_8$ alkyl alcohols. In another embodiment, the oil comprises one or more oils selected from tallow oil, corn oil, canola oil, capric/caprylic triglycerides, castor oil, coconut oil, cottonseed oil, fish oil, jojoba oil, lard, linseed oil, neetsfoot oil, oiticica oil, palm oil, peanut oil, rapeseed oil, rice oil, safflower oil, soya oil, sunflower oil, tung oil, jatropha oil, wheat oil, rye oil, barley oil, and vegetable oil blends.

In one embodiment, the extractant comprises one or more fatty amides of the formula R(C=O)N(R')(R"), wherein
R is independently selected from the group consisting of $C_3$ to $C_{27}$ alkyl groups optionally interrupted with one or more double bonds, and
R' and R" are independently selected from the group consisting of hydrogen and $C_1$-$C_6$ alkyl groups optionally containing one or more hydroxyl groups.

In another embodiment, the extractant comprises one or more fatty esters of the formula R—(C=O)—OCHR'CHR"—OH, wherein
R is independently selected from the group consisting of $C_3$ to $C_{27}$ alkyl groups optionally interrupted with one or more double bonds, and
R' and R" are independently selected from the group consisting of hydrogen and $C_1$-$C_4$ alkyl groups.

In one embodiment, the extractant comprises one or more fatty esters of the formula R—(C=O)—OR', wherein
R is independently selected from the group consisting of $C_3$ to $C_{27}$ alkyl groups optionally interrupted with one or more double bonds, and
R' is an alkyl group of 8 carbons or less.

The present invention is directed to a method for producing a product alcohol comprising: (a) providing a fermentation broth comprising a recombinant microorganism capable of producing a product alcohol in a fermentation vessel and whereby a product alcohol is produced; (b) contacting the fermentation broth with an extractant to form a two-phase mixture comprising an aqueous phase and an organic phase, wherein the product alcohol and the oil partition into the organic phase such that the organic phase comprises the product alcohol and the oil; (c) separating the organic phase from the aqueous phase; (d) separating the product alcohol from the organic phase; and optionally steps (b) and (c) occur concurrently. In one embodiment, the method further comprises the step of producing a feedstock slurry; separating the feedstock slurry to produce (i) an aqueous layer, (ii) oil layer, and (iii) a solids layer; and feeding the aqueous layer to the fermentation vessel. In another embodiment, the method further comprises the step of further comprising: contacting the oil of the oil layer with one or more substances capable of chemically converting the oil into an extractant selected from the group consisting of fatty acids, fatty alcohols, fatty amides, fatty esters, triglycerides, and mixtures thereof, whereby at least a portion of the oil is converted to the extractant.

In one embodiment, the extractant is selected from fatty acid, fatty alcohol, fatty amide, fatty ester, triglycerides, and mixtures thereof. In another embodiment, the extractant is selected from hydroxylated triglycerides, alkoxylated triglycerides (e.g., methoxylated, ethoxylated), hydroxylated fatty acids, alkoxylated fatty acids hydroxylated fatty alcohols, and alkoxylated fatty alcohols. In one embodiment, the extractant is selected from saturated fatty acids, unsaturated fatty acids, saturated fatty alcohols, unsaturated fatty alcohols, saturated fatty amides, unsaturated fatty amides, saturated fatty esters, unsaturated fatty esters, and mixtures thereof. In one embodiment, the extractant may be a liquid or solid. In a further embodiment, the extractant may be in the form of beads. In one embodiment, the product alcohol is $C_1$ to $C_8$ alkyl alcohols. In another embodiment, the extractant has a partition coefficient for the product alcohol that is greater than the partition coefficient of the oil of the oil layer for the product alcohol. In one embodiment, the product alcohol is $C_1$ to $C_8$ alkyl alcohols. In another embodiment, the oil comprises one or more oils selected from tallow oil, corn oil, canola oil, capric/caprylic triglycerides, castor oil, coconut oil, cottonseed oil, fish oil, jojoba oil, lard, linseed oil, neetsfoot oil, oiticica oil, palm oil, peanut oil, rapeseed oil, rice oil, safflower oil, soya oil, sunflower oil, tung oil, jatropha oil, wheat oil, rye oil, barley oil, and vegetable oil blends.

In some embodiments, a method of removing oil derived from biomass from a fermentation process includes: contacting a biomass feedstream including an amount of oil with one or more substances capable of chemically converting the oil into an extractant selected from the group consisting of fatty acids, fatty alcohols, fatty amides, fatty acid methyl esters, fatty acid glycol esters, triglycerides and mixtures thereof, whereby at least a portion of the oil is converted to the extractant. The triglycerides may be hydroxylated or alkoxylated (e.g., methoxylated, ethoxylated). The extractant has a partition coefficient for a fermentative alcohol greater than the partition coefficient of the oil for the fermentative alcohol. In some embodiments the biomass feedstream is milled corn and the oil is corn oil. In some embodiments, the method also includes contacting the biomass feedstream having the extractant with a fermentation broth, the fermentation broth including the fermentative alcohol, wherein the fermentative alcohol partitions into the extractant.

The present invention is directed to a method for producing an extractant comprising providing a biomass comprising oil; and converting at least a portion of the oil into an extractant selected from the group consisting of fatty acids, fatty alcohols, fatty amides, fatty esters, triglycerides, and mixtures thereof. In one embodiment, the step of converting the oil into an extractant comprises one or more of the steps of incubating the oil in the presence of tetrahydrofuran and lithium aluminum hydride; incubating the oil with sodium hydroxide; incubating the oil with sulfuric acid and methanol; incubating the oil with anhydrous ammonia in the presence of ammonium acetate; incubating the oil with ammonia in water; contacting the oil with toluene, cation exchange resin, glacial acetic acid, lipase, and hydrogen peroxide; incubating the oil under high temperature conditions, or incubating the oil under high pressure conditions.

In some embodiments, an in situ method of producing an extractant for in situ removal of a product alcohol includes: (a) providing biomass including fermentable sugars and oil, the oil including triglycerides; (b) separating the oil of (a) from the biomass; and (c) contacting the separated oil with one or more reactants or solvents capable of chemically reacting the triglycerides to obtain a reaction product selected from the group consisting of fatty acids, fatty alcohols, fatty amides, a mixture of fatty amides and fatty acids, fatty acid methyl esters, fatty acid glycol esters, triglycerides, and mixtures thereof, whereby the triglycerides in the oil are converted into the reaction product. The triglycerides may be hydroxylated or alkoxylated (e.g., methoxylated, ethoxylated). The reaction product forms a fermentation product extractant having a partition coefficient for the product alcohol greater than a partition coefficient of the oil of the biomass for the product alcohol.

In some embodiments, a method for producing butanol includes: (a) providing biomass including oligosaccharides and oil, the oil including glycerides; (b) contacting the biomass with a saccharification enzyme capable of converting oligosaccharides into monosaccharides; (c) separating the oil from the biomass of (a) or (b); (d) contacting the separated oil with a composition including one or more reactants or solvents whereby the glycerides in the oil form an extractant; (e) contacting the biomass with a recombinant microorganism capable of converting the monosaccharides to butanol whereby a fermentation product comprising butanol is produced; and (f) contacting the fermentation product with the extractant of (d) whereby the butanol is separated from the fermentation product. The extractant has a partition coefficient for the butanol greater than the partition coefficient of the oil of the biomass for the butanol. In some embodiments, the extractant of step (d) is selected from the group consisting of fatty acids, fatty alcohols, fatty amides, a mixture of fatty amides and fatty acids, fatty acid methyl esters, fatty acid glycol esters, triglycerides, and mixtures thereof. The triglycerides may be hydroxylated or alkoxylated (e.g., methoxylated, ethoxylated).

In some embodiments, a method includes, at a step during a process to produce a product alcohol from a feedstock, converting at least of portion of a plant-derived oil to an extractant having a extractant partition coefficient for the product alcohol greater than a partition coefficient of the plant-derived oil for the product alcohol. In some embodiments, the plant-derived oil is derived from the feedstock.

In some embodiments, the product alcohol is isobutanol and the extractant partition coefficient is at least about 0.28. In some embodiments, the extractant partition coefficient for isobutanol is at least about 1. In some embodiments, the extractant partition coefficient for isobutanol is at least about 2.

In some embodiments, the process to produce a product alcohol from a feedstock includes (a) producing a feedstock slurry; (b) separating the feedstock slurry of (a) to produce a product including (i) an aqueous layer, (ii) a oil layer, and (iii) a solids layer; and (c) feeding the aqueous layer of (b) to a fermentation vessel. In some embodiments, the step of separating the feedstock slurry occurs by centrifugation. In some embodiments, the oil layer is plant-derived oil layer. In some embodiments, the process further includes obtaining at least a portion of plant-derived oil from the plant-derived oil layer.

In some embodiments, the process further includes adding the extractant to the fermentation vessel to form a two-phase mixture including an aqueous phase and a product alcohol-containing organic phase, whereby the product alcohol partitions into the product alcohol-containing organic phase.

In some embodiments, the process further includes fermenting sugar of the aqueous phase to produce the product alcohol, whereby the product alcohol partitions into the product alcohol-containing organic phase.

In some embodiments, a method of removing oil derived from biomass from a fermentation process includes (a) providing a fermentation broth including a product alcohol and oil derived from biomass, the oil including glycerides; (b) contacting the fermentation broth with an extractant to form a two-phase mixture comprising an aqueous phase and an organic phase, the product alcohol and the oil partitioning into the organic phase such that the organic phase comprises the product alcohol and the oil; (c) separating the organic phase from the aqueous phase; (d) separating the product alcohol from the organic phase; and (e) contacting the organic phase with a composition comprising one or more reactants or solvents whereby the glycerides in the oil form additional extractant; and (f) repeat step (b) by contacting the fermentation broth with the additional extractant of step (e).

In some embodiments, the additional extractant is selected from the group consisting of fatty acid, fatty alcohol, fatty amide, fatty acid methyl ester, fatty acid glycol ester, triglyceride, and mixtures thereof. The triglycerides may be hydroxylated or alkoxylated (e.g., methoxylated, ethoxylated).

In some embodiments, the product alcohol is butanol.

In some embodiments, an in situ fermentation extractant-forming composition includes (a) oil derived from biomass; (b) one or more substances capable of chemically converting the oil into one or more products selected from the group consisting of fatty acids, fatty alcohols, fatty amides, fatty acid methyl esters, fatty acid glycol esters, and triglycerides; and (c) the one or more products, wherein the one or more products are in an amount from about 50 wt % to about 99 wt % of the composition. The triglycerides may be hydroxylated or alkoxylated (e.g., methoxylated, ethoxylated).

In some embodiments, a composition includes a recombinant microorganism capable of producing butanol, butanol, and at least one solvent selected from the group consisting of fatty acid, fatty alcohol, fatty amide, fatty acid methyl ester, fatty acid glycol ester, triglyceride, and mixtures thereof. The triglycerides may be hydroxylated or alkoxylated (e.g., methoxylated, ethoxylated).

In some embodiments, a composition includes a recombinant microorganism capable of producing butanol, butanol, and fatty alcohols.

In some embodiments, a composition includes a recombinant microorganism capable of producing butanol, butanol, and a mixture of fatty amides, wherein the mixture of fatty amides comprises linoleamide, oleamide, palmitamide, and stearamide.

In some embodiments, a composition includes a composition comprising a recombinant microorganism capable of producing butanol, butanol, and corn oil, wherein the corn oil is from about 28% to about 67% hydroxylated.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which lipids are removed from a liquefied biomass before fermentation, and in which the removed lipids are converted into an extractant and supplied to a fermentation vessel.

Figure 2:
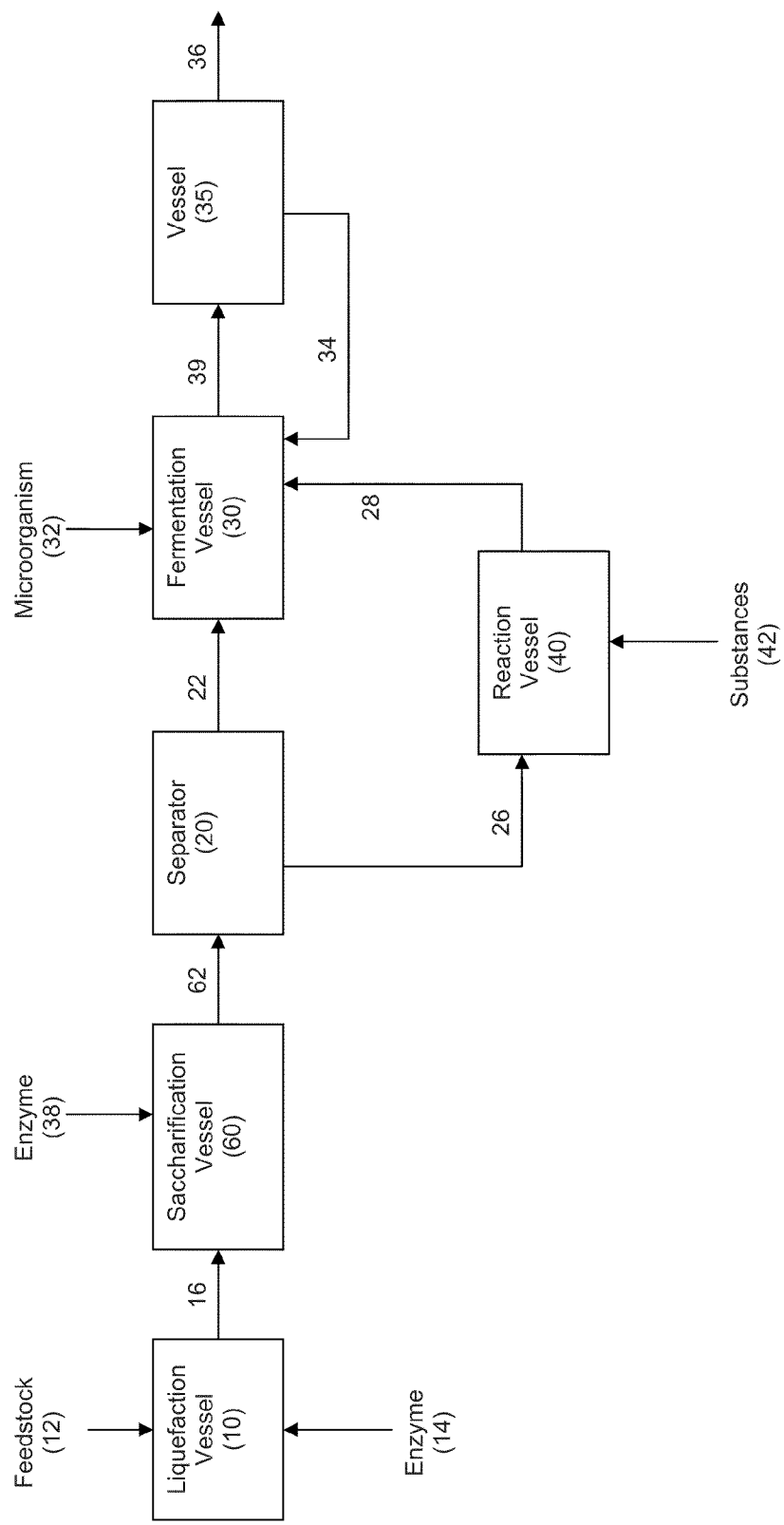

FIG. 2 schematically illustrates an exemplary method and system of the present invention, in which lipids are removed from a liquefied and saccharified biomass before fermentation, and in which the removed lipids are converted into an extractant and supplied to a fermentation vessel.

Figure 3:
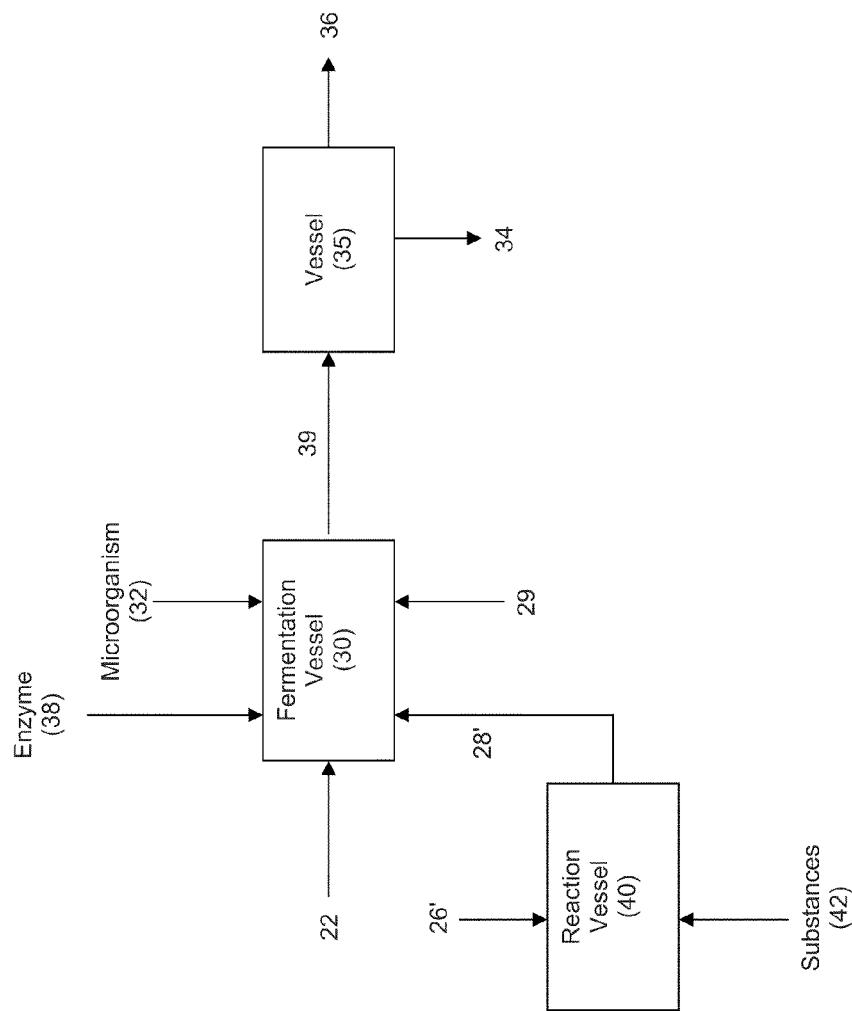

FIG. 3 schematically illustrates an exemplary method and system of the present invention, in which lipids are removed from a biomass and converted into an extractant that is supplied to a fermentation vessel.

Figure 4:
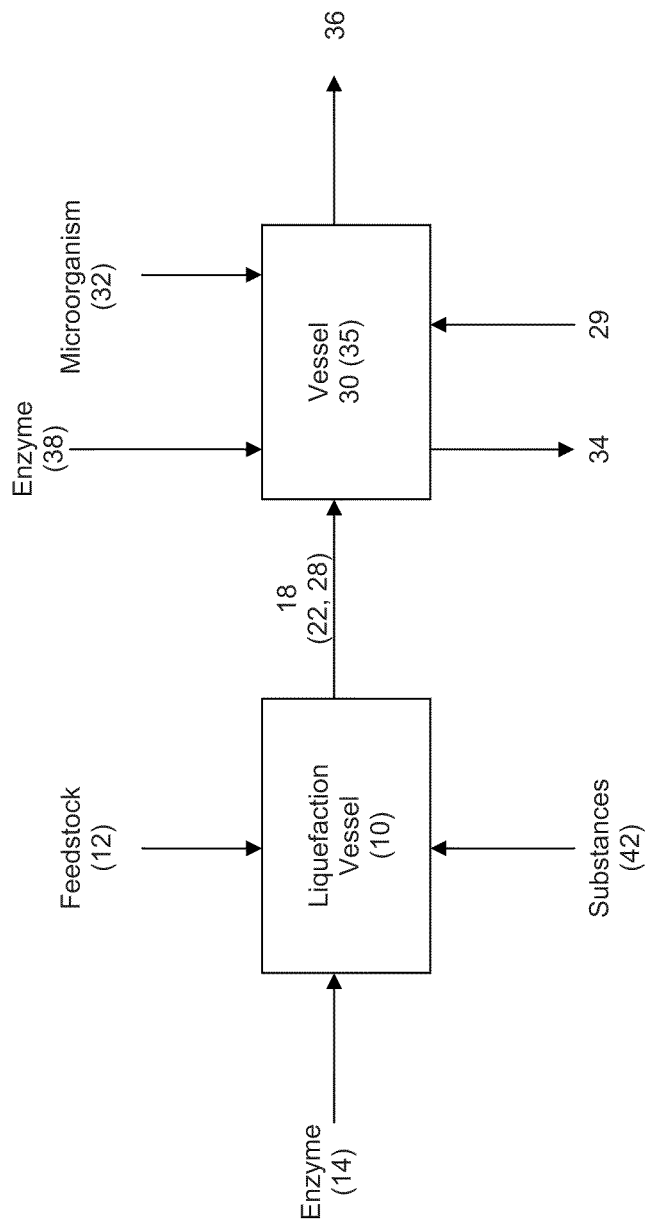

FIG. 4 schematically illustrates an exemplary method and system of the present invention, in which lipids in a biomass feedstream are converted into an extractant and supplied to a fermentation vessel.

Figure 5:
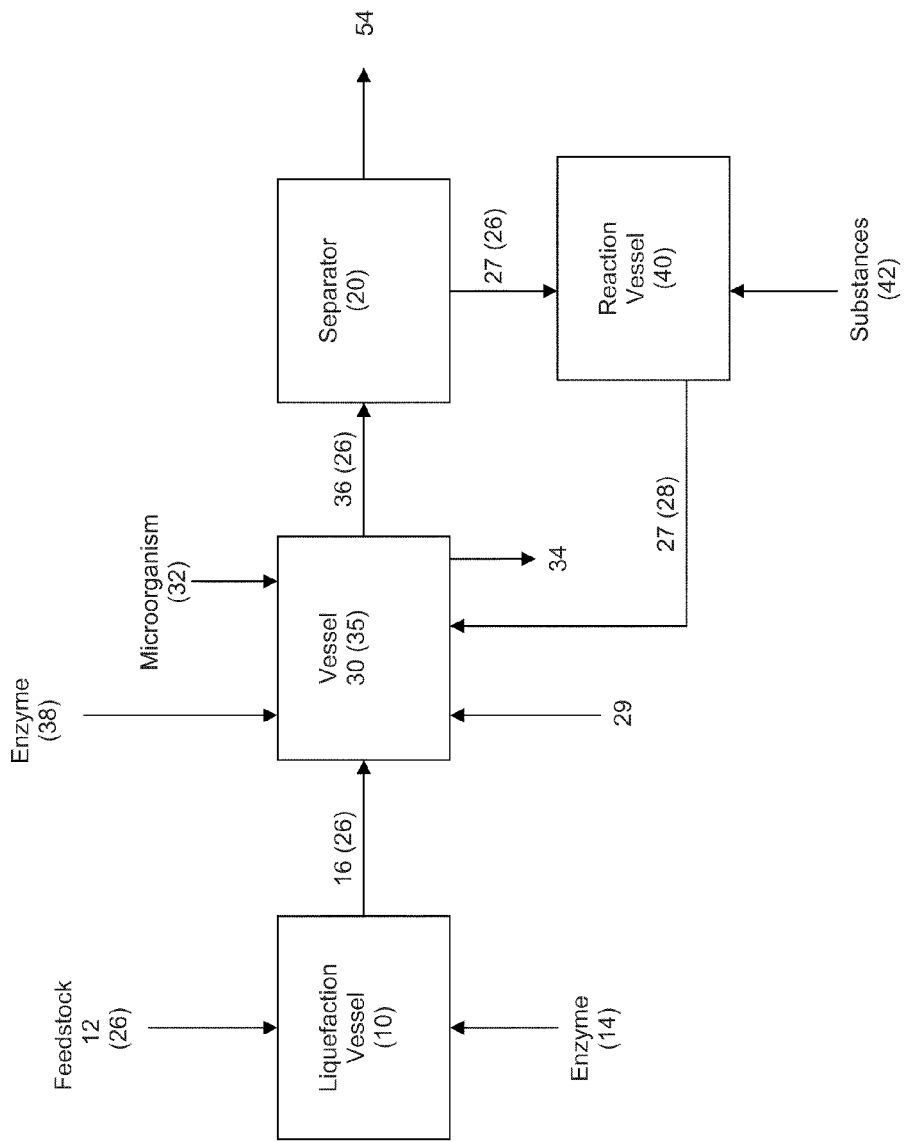

FIG. 5 schematically illustrates an exemplary method and system of the present invention, in which lipids present in a first extractant exiting a fermentation vessel are separated from the first extractant and converted into a second extractant that is supplied to a fermentation vessel.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore, "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolysable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstock include, but are not limited to, rye, wheat, corn, cane, barley, cellulosic material, lignocellulosic material, or mixtures thereof. Where reference is made to "corn oil," it will be appreciated that the term encompasses the oil produced from a given feedstock in other embodiments of the present invention.

"Fermentation broth" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; one carbon substrates; and mixtures thereof.

"Fermentable sugar" as used herein refers to sugar capable of being metabolized by the microorganisms disclosed herein for the production of fermentative alcohol.

"Fermentation vessel" as used herein means the vessel in which the fermentation reaction by which product alcohol such as butanol is made from sugars is carried out.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessels may be one in the same vessel.

"Sugar" as used herein refers to oligosaccharides, disaccharides, and/or monosaccharides.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), and/or isobutanol (iBuOH or I-BUOH, also known as 2-methyl-1-propanol), either individually or as mixtures thereof.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis and recovery of an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used, and (iv) the alcohol equivalent of the butanol ester in either the organic or aqueous phase.

"In Situ Product Removal (ISPR)" as used herein means the selective removal of a specific fermentation product from a biological process such as fermentation to control the product concentration in the biological process as the product is produced.

"Extractant" or "ISPR extractant" as used herein means an organic solvent used to extract any product alcohol such as butanol isomer. The extractant may be a solid or liquid at fermentation temperature. From time to time, as used herein the term "solvent" may be used synonymously with "extractant."

"Fatty acid extractants" as used herein means extractants derived from native oil by chemically reacting the glycerides in the native oil with one or more solvents or reactants to obtain one or more reaction products selected from the group consisting of fatty acids, fatty alcohols, fatty amides, fatty acid methyl esters, fatty acid glycol esters, triglycerides, and mixtures thereof. The triglycerides may be hydroxylated or alkoxylated (e.g., methoxylated, ethoxylated).

"Native oil" as used herein refers to lipids obtained from plants (e.g., biomass) or animals. "Plant-derived oil" as used herein refers to lipids obtain from plants, in particular. From time to time, "lipids" may be used synonymously with "oil" and "glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having a long, aliphatic chain of $C_4$ to $C_{22}$ carbon atoms, which is either saturated or unsaturated.

The term "fatty aldehyde" as used herein refers to an aldehyde having a long, aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated The term "fatty ester" as used herein refers to an ester having a long aliphatic chain of $C_4$ to $C_{22}$ carbon atoms, which is either saturated or unsaturated.

The term "water-immiscible" refers to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "separation" as used herein is synonymous with "recovery" and refers to removing a chemical compound from an initial mixture to obtain the compound in greater purity or at a higher concentration than the purity or concentration of the compound in the initial mixture.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention provides extractants obtained by chemical conversion of oil derived from biomass and methods of producing the extractants. In particular, the glycerides in the oil can be chemically converted into one or more products including fatty acids, fatty alcohols, fatty amides, fatty acid methyl esters, fatty acid glycol esters, and triglycerides, and mixtures thereof, collectively referred to herein as fatty acid extractants. The triglycerides may be hydroxylated or alkoxylated (e.g., methoxylated, ethoxylated). Fatty acid extractants can serve as extractants for in situ removal of a product alcohol such as butanol from a fermentation broth. Thus, the present invention also provides methods for producing a product alcohol such as butanol through extractive fermentation using the extractants that were produced from the biomass oil. The present invention also provides methods for removing oil from an alcohol fermentation process by separating the oil derived from a feedstock. The feedstock can be liquefied to create a slurry prior to oil removal. Thus, the slurry includes a fermentable carbon source, oil, and undissolved solids. The oil, and in some embodiments, the undissolved solids, can be removed from the slurry prior to the slurry being fed to the fermentation vessel. Removal of the oil and in some embodiments, the undissolved solids, can reduce the loss, degradation of the partition coefficient of the extractant over time that is attributable to the presence of the oil (and in some embodiments the solids) in the fermentation vessel. Moreover, the separated oil can be chemically converted into a fatty acid extractant which can be fed to the fermentation vessel. The fatty acid extractant can have a partition coefficient for a fermentative alcohol greater than a partition coefficient of the oil for the fermentative alcohol. Further, the fatty acid extractant can be used in place of or in addition to a commercial exogenous extractant such as oleyl alcohol that was not chemically converted from the feedstock according to the methods of the present invention. Thus, the methods of the present invention can reduce the raw material expense associated with the exogenous extractant by producing an extractant at a step in a fermentation process via chemical conversion of oil derived from a feedstock.

The present invention will be described with reference to the Figures. FIG. 1 illustrates an exemplary process flow diagram for production of fermentative alcohol according to an embodiment of the present invention. As shown, a feedstock 12 can be introduced to an inlet in a liquefaction vessel 10 and liquefied to produce a feedstock slurry 16. Feedstock 12 contains hydrolysable starch that supplies a fermentable carbon source (e.g., fermentable sugar such as glucose), and can be a biomass such as, but not limited to rye, wheat, corn, cane, barley, cellulosic material, lignocellulosic material, or mixtures thereof, or can otherwise be derived from a biomass. In some embodiments, feedstock 12 can be one or more components of a fractionated biomass and in other embodiments, feedstock 12 can be a milled, unfractionated biomass. In some embodiments, feedstock 12 can be corn such as dry milled, unfractionated corn kernels, and the undissolved particles can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn, in which the undissolved solids have not been separated therefrom. However, it should be understood that the exemplary methods and systems described herein can be modified for different feedstocks whether fractionated or not, as apparent to one of skill in the art. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil can provide a fatty acid extractant having a high oleic acid content for contacting with a fermentation broth. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond may provide advantages with respect to melting point without sacrificing suitable thermal and oxidative stability for process considerations.

The process of liquefying feedstock 12 involves hydrolysis of starch in feedstock 12 into sugars including, for example, dextrins and oligosaccharides, and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10.

Feedstock slurry 16 produced from liquefying feedstock 12 includes sugar, oil, and undissolved solids derived from the feedstock. Feedstock slurry 16 can be discharged from an outlet of liquefaction vessel 10. In some embodiments, feedstock 12 is corn or corn kernels and therefore, feedstock slurry 16 is a corn mash slurry.

Feedstock slurry 16 is introduced into an inlet of a separator 20 which is configured to remove some, or preferably substantially all, of the oil present in the feedstock slurry 16. The removed oil is provided as a stream 26 to a reaction vessel 40, and the remaining feedstock including the sugar and water is discharged as an aqueous stream 22 to a fermentation vessel 30. Aqueous stream 22 can include the undissolved solids of the slurry 16, but since the oil 26 was removed via separator 20, the fermentation broth in fermentation vessel 30 still has a reduced amount of oil. The oil stream 26 discharged from separator 20 has an amount of glycerides, particularly triglycerides, which are contacted with one or more substances 42 in reaction vessel 40. Substances 42 are reactants or solvents capable of chemically converting at least a portion of the glycerides in oil 26 into a fatty acid extractant 28. In some embodiments, the amount of fatty acid extractant 28 in the oil from chemical conversion of the glycerides via substances 42 can be at least about 17 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, at least about 95 wt %, or at least about 99 wt %.

Separator 20 can be any suitable separator known in the art for removing oil from an aqueous feedstream, including but not limited to, siphoning, aspiration decantation, centrifugation, using a gravity settler, membrane-assisted phase splitting, and the like. In some embodiments, separator 20 can also remove the undissolved solids in feedstock slurry 16 and discharge the undissolved solids as a solid phase or wet cake 24. For example, in some embodiments, separator 20 can includes a filter press, vacuum filtration, or a centrifuge for separating the undissolved solids from feedstock slurry 16. For example, in some embodiments, separator 20 includes a tricanter centrifuge 20 that agitates or spins feedstock slurry 16 to produces a centrifuge product comprising an aqueous layer containing the sugar and water (i.e., stream 22), a solids layer containing the undissolved solids (i.e., wet cake 24), and an oil layer (i.e., oil stream 26). When slurry 16 is a corn mash slurry, then oil 26 is free corn oil. The term free corn oil as used herein means corn oil that is freed from the corn germ. For a corn mash slurry as feedstock slurry 16, wet cake 24 includes at least about 50% by weight of the undissolved particles present in the feedstock slurry, at least about 55% by weight of the undissolved particles present in the feedstock slurry, at least about 60% by weight of the undissolved particles present in the feedstock slurry, at least about 65% by weight of the undissolved particles present in the feedstock slurry, at least about 70% by weight of the undissolved particles present in the feedstock slurry, at least about 75% by weight of the undissolved particles present in the feedstock slurry, at least about 80% by weight of the undissolved particles present in the feedstock slurry, at least about 85% by weight of the undissolved particles present in the feedstock slurry, at least about 90% by weight of the undissolved particles present in the feedstock slurry, at least about 95% by weight of the undissolved particles present in the feedstock slurry, or about 99% by weight of the undissolved particles present in the feedstock slurry.

When wet cake 24 is removed via centrifuge 20, in some embodiments, a portion of the oil from feedstock 12, such as corn oil when the feedstock is corn, remains in wet cake 24. In such instances, wet cake 24 includes corn oil in an amount of less than about 20% by weight of dry solids content of wet cake 24. Wet cake 24 can be discharged out an outlet located near the bottom of centrifuge 20. Wet cake 24 can also include a portion of the fermentable carbon and water. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 24 can be dried to form Dried Distillers' Grains with Solubles (DDGS) through any suitable known process. The formation of the DDGS from wet cake 24 formed in centrifuge 20 has several benefits. Because the undissolved solids do not go to the fermentation vessel, the DDGS does not have trapped extractant and/or product alcohol such as butanol, it is not subjected to the conditions of the fermentation vessel, and it does not contact the microorganisms present in the fermentation vessel. These benefits make it easier to process and sell DDGS, for example as animal feed. Methods and systems for removing undissolved solids from feedstock 16 via centrifugation are described in detail in co-pending, commonly owned U.S. Provisional Patent Application No. 61/356,290, filed on Jun. 18, 2010, which is incorporated herein in its entirety by reference thereto.

In some embodiments, oil 26 is not discharged separately from wet cake 24, but rather oil 26 is included as part of wet cake 24 and is ultimately present in the DDGS. In such instances, the oil can be separated from the DDGS and converted to a fatty acid extractant for subsequent use in the same or different alcohol fermentation process. In any case, removal of the oil component of the feedstock is advantageous to alcohol production such as butanol production because oil present in the fermentation vessel can dilute the ISPR extractant and can reduce the partition coefficient of the fermentative alcohol into the organic phase. Also, the oil can break down into fatty acids and glycerin, which can accumulate in the water and reduce the amount of water that is available for recycling throughout the system. Thus, removal of the oil component of the feedstock can also increase the efficiency of the product alcohol production by increasing the amount of water that can be recycled through the system.

Aqueous stream 22 and a microorganism 32 are introduced to a fermentation vessel 30 to be included in a fermentation broth held in fermentation vessel 30. Fermentation vessel 30 is configured to ferment aqueous stream 22 to produce a product alcohol such as butanol. In particular, microorganism 32 metabolizes the fermentable sugar in slurry 16 and excretes a product alcohol. Microorganism 32 is selected from the group of bacteria, cyanobacteria, filamentous fungi, and yeasts. In some embodiments, microorganism 32 can be a bacteria, such as $E.\ coli$. In some embodiments, microorganism 32 can be a fermentative recombinant microorganism. Aqueous solution 22 can include the sugar, for example, in the form of oligosaccharides, and water, and can comprise less than about 20 g/L of monomeric glucose, more preferably less than about 10 g/L or less than about 5 g/L of monomeric glucose. Suitable methodology to determine the amount of monomeric glucose is well known in the art. Such suitable methods known in the art include HPLC.

In some embodiments, aqueous stream 22 is subjected to a saccharification process in order to break the complex sugars (e.g., oligosaccharides) in stream 22 into monosaccharides that can be readily metabolized by microorganism 32. Any known saccharification process, normally utilized by the industry can be used including, but not limited to, the acid process, the acid-enzyme process, or the enzyme process. In some embodiments, simultaneous saccharification and fermentation (SSF) can occur inside fermentation vessel 30. In some embodiments, an enzyme 38 such as glucoamylase, can be introduced to an inlet in fermentation vessel 30 in order to breakdown the starch to glucose which can be metabolized by microorganism 32.

In situ product removal (ISPR) can be utilized to remove the product alcohol from fermentation vessel 30 as the product alcohol is produced by microorganism 32. For extractive fermentation, such ISPR includes liquid-liquid extraction. Liquid-liquid extraction can be performed according to the processes described in U.S. Patent Application Publication No. 2009/0305370, the disclosure of which is hereby incorporated in its entirety. U.S. Patent Application Publication No. 2009/030537 describes methods for producing and recovering butanol from a fermentation broth using extractive fermentation, the methods comprising the step of contacting the fermentation broth with a water immiscible extractant. Typically, the extractant can be an organic extractant selected from the group consisting of fatty acids, fatty alcohols, fatty amides, a mixture of fatty amides and fatty acids, esters of fatty acids, fatty aldehydes, fatty acid methyl esters, fatty acid glycol esters, triglycerides and mixtures thereof, to form a two-phase mixture comprising an aqueous phase and an organic phase. With reference to the embodiment of FIG. 1, fermentation vessel 30 has one or more inlets for receiving one or more water immiscible ISPR extractants, including fatty acid extractant 28 from vessel 40. Fatty acid extractant 28 contacts the fermentation broth and forms a two-phase mixture comprising an aqueous phase and an organic phase. The product alcohol present in the fermentation broth partitions into the organic phase. The biphasic mixture can be removed from fermentation vessel 30 as stream 39 and introduced into a vessel 35, in which separation of the aqueous and organic phases is performed to produce an alcohol-containing organic phase 36 and an aqueous phase 34. The alcohol-containing organic phase 36 is separated from the aqueous phase 34 of the biphasic mixture 39 using methods known in the art, including but not limited to, siphoning, decantation, centrifugation, using a gravity settler, membrane-assisted phase splitting, and the like. All or part of the aqueous phase 34 can be recycled into fermentation vessel 30 as fermentation medium (as shown), or otherwise discarded and replaced with fresh medium, or treated for the removal of any remaining product alcohol and then recycled to fermentation vessel 40. The alcohol-containing organic phase 36 is treated to recover the product alcohol, and the resulting alcohol-lean extractant can then be recycled back (not shown) into fermentation vessel 30, usually in combination with fresh make-up extractant 28, for further extraction of the product alcohol. Alternatively, fresh extractant 28 can be continuously added to the fermentation vessel to replace the extractant removed in biphasic mixture stream 39.

In some embodiments, one or more additional ISPR extractants can be introduced into fermentation vessel 30, such as extractant 29 illustrated in the embodiments of FIGS. 3-5, to form a two-phase mixture comprising an aqueous phase and an organic phase, with the product alcohol partitioning into the organic phase. Such one or more additional extractants 29 can be another fatty acid extractant and/or an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. In some embodiments, ISPR extractant 29 can be a carboxylic acid, and in some embodiments, ISPR extractant 29 can be a free fatty acid. In some embodiments, the carboxylic acid or free fatty acid can have a chain of 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments.

In some embodiments, ISPR extractant 29 is one or more of the following fatty acids: azaleic, capric, caprylic, castor, coconut (i.e., as a naturally-occurring combination of fatty acids including lauric, myrisitic, palmitic, caprylic, capric, stearic, caproic, arachidic, oleic, and linoleic, for example), dimer, isostearic, lauric, linseed, myristic, oleic, palm oil, palmitic, palm kernel, pelargonic, ricinoleic, sebacic, soya, stearic acid, tall oil, tallow, and #12 hydroxy stearic. In some embodiments, ISPR extractant 29 is one or more of diacids, for example, azelaic acid and sebacic acid. Thus, in some embodiments, ISPR extractant 29 can be a mixture of two or more different fatty acids. In some embodiments, ISPR extractant 29 can be free fatty acids produced from enzymatic hydrolysis of native oil such as biomass lipids as described, for example, in co-pending, commonly owned U.S. Provisional Patent Application No. 61/368,444, filed on Jul. 28, 2010. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art.

In the embodiment of FIG. 1, the product alcohol is extracted from the fermentation broth in situ, with the separation of the biphasic mixture 39 occurring in a separate vessel 35. In situ extractive fermentation can be carried out in a batch mode or a continuous mode in fermentation vessel 30. For in situ extractive fermentation, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production, for example, the ISPR extractant can contact the fermentation medium at a time before the butanol concentration reaches a toxic level. After contacting the fermentation medium with the ISPR extractant, the butanol product partitions into the extractant, decreasing the concentration of butanol in the aqueous phase containing the microorganism, thereby limiting the exposure of the production microorganism to the inhibitory butanol product.

The volume of the ISPR extractant to be used depends on a number of factors including the volume of the fermentation medium, the size of the fermentation vessel, the partition coefficient of the extractant for the butanol product, and the fermentation mode chosen, as described below. The volume of the extractant can be about 3% to about 60% of the fermentation vessel working volume. Depending on the efficiency of the extraction, the aqueous phase titer of butanol in the fermentation medium can be, for example, from about 5 g/L to about 85 g/L, from about 10 g/L to about 40 g/L, from about 10 g/L to about 20 g/L, from about 15 g/L to about 50 g/L, or from about 20 g/L to about 60 g/L. Without being held to theory, it is believed that higher butanol titer may obtained with the extractive fermentation method, in part, from the removal of the toxic butanol product from the fermentation medium, thereby keeping the level below that which is toxic to the microorganism.

In a batchwise mode of in situ extractive fermentation, a volume of organic extractant is added to the fermentation vessel and the extractant is not removed during the process. This mode requires a larger volume of organic extractant to minimize the concentration of the inhibitory butanol product in the fermentation medium. Consequently, the volume of the fermentation medium is less and the amount of product produced is less than that obtained using the continuous mode. For example, the volume of the extractant in the batchwise mode can be 20% to about 60% of the fermentation vessel working volume in one embodiment, and about 30% to about 60% in another embodiment.

Gas stripping (not shown) can be used concurrently with the organic extractant to remove the product alcohol from the fermentation medium.

In some embodiments, separation of the biphasic mixture can occur in the fermentation vessel, as shown in the embodiments of later described FIGS. 4 and 5. In particular, in a continuous mode of in situ extractive fermentation, in one embodiment, extractant 28 may be introduced into fermentation vessel 30 to obtain the biphasic mixture therein, with the alcohol-containing organic-phase stream 36 exiting directly from fermentation vessel 30. Aqueous phase stream 34 can also exit directly from fermentation vessel 30, be treated for the removal of any remaining product alcohol and recycled, or discarded and replaced with fresh fermentation medium. The extraction of the alcohol product by the ISPR extractant can be done with or without the removal of microorganism 32 from the fermentation broth. Microorganism 32 can be removed from the fermentation broth by means known in the art including, but not limited to, filtration or centrifugation. For example, aqueous phase stream 34 can include microorganism 32 such as a yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

In a continuous mode of in situ extractive fermentation, the volume of the extractant can be about 3% to about 50% of the fermentation vessel working volume in one embodiment, about 3% to about 30% in another embodiment, 3% to about 20% in another embodiment; and 3% to about 10% in another embodiment. Because the product is continually removed from the reactor, a smaller volume of extractant is required enabling a larger volume of the fermentation medium to be used.

As an alternative to in situ extractive fermentation, the product alcohol can be extracted from the fermentation broth downstream of fermentation vessel 30. In such an instance, the fermentation broth can be removed from fermentation vessel 30 and introduced into vessel 35. Extractant 28 can then be introduced in vessel 35 and contacted with the fermentation broth to obtain biphasic mixture 39 in vessel 35, which is then separated into the organic 36 and aqueous 34 phases. Alternatively, extractant 28 can be added to the fermentation broth in a separate vessel (not shown) prior to introduction to vessel 35.

Fatty acid extractant 28 has a partition coefficient for the product alcohol greater than the partition coefficient of oil 26 for the product alcohol. For example, where the feedstock 12 is corn, corn oil 26, if present in the fermentation broth, can have a partition coefficient for the product alcohol of less than about 0.28, whereas fatty acid extractant 28 derived from corn oil 26 can have a partition coefficient of about 0.28 and greater. In one embodiment, fatty acid extractant 28 has a partition coefficient for the product alcohol such as butanol of at least about 1, at least about 2 in another embodiment, at least about 2.5 in another embodiment, at least about 2.75 in another embodiment, and at least about 3 in another embodiment. Thus, removal of the oil component of the feedstock increases the efficiency of the product alcohol production in extractive fermentation by not only reducing the threat to degradation of the partition coefficient of the ISPR extractant, but also by serving as a raw material for the production of a fatty acid extractant that can partition the product alcohol from the aqueous phase more so than the oil itself. Moreover, fatty acid extractant 28 derived from oil 26 in feedstock 12 can be used alone or in combination with an exogenous extractant (e.g., externally supplied oleyl alcohol), thereby reducing or eliminating the cost associated with the exogenous extractant.

Moreover, in the instance that fatty acid extractant 28 includes free fatty acids, a rate of glucose consumption by microorganism 32 in fermentation vessel 30 can be higher in the presence of such free fatty acids than in the absence of such free fatty acids. Thus, in some embodiments of the present invention, the fermentation broth can be contacted with a fatty acid extractant having free fatty acids, whereby the free fatty acids can increase glucose uptake by microorganism 32 compared to the glucose uptake when an ISPR extractant without free fatty acids (e.g., oleyl alcohol) is used in extractive fermentation. For example, as illustrated in Table 1 of Example 2 described below, fatty amide/fatty acid mixtures used as fatty acid extractants in extractive fermentation can provide a higher rate of glucose uptake by a *Saccharomyces* butanologen than when using oleyl alcohol as an extractant. Methods for producing a product alcohol from a fermentation process in which free fatty acids are produced at a step in the process and are contacted with microorganism cultures in a fermentation vessel for improving microorganism growth rate and glucose consumption are described in co-pending, commonly owned U.S. Provisional Patent Application No. 61/368,451, filed on Jul. 28, 2010, which is incorporated herein in its entirety by reference thereto.

In some embodiments, the system and processes of FIG. 1 can be modified such that simultaneous saccharification and fermentation in fermentation vessel 30 is replaced with a separate saccharification vessel 60 between separator 20 and fermentation vessel 30, as should be apparent to one of skill in the art.

In still other embodiments, as shown, for example, in the embodiment of FIG. 2, saccharification can occur in a separate saccharification vessel 60 which is located between separator 20 and liquefaction vessel 10. FIG. 2 is substantially identical to FIG. 1 except for the inclusion of separate saccharification vessel 60 receiving enzyme 38, with oil stream 26 being separated from a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 and is introduced into separator 20. Feedstock stream 62 includes monosaccharides, oil, and undissolved solids derived from the feedstock. In separator 20, feedstock stream 62 is separated into oil stream 26 and a substantially aqueous stream 23, which is fed to fermentation vessel 30. In the embodiment shown, aqueous stream 23 includes undissolved solids. Alternatively, the solids can be removed in separator 20 as a wet cake 24, as described with reference to the embodiment of FIG. 1. The oil stream 26 discharged from separator 20 has an amount of glycerides, particularly triglycerides, which are contacted with one or more substances 42 in reaction vessel 40. Substances 42 chemically converts at least a portion of the glycerides from oil 26 into fatty acid extractant 28 which is fed to fermentation vessel 30. The remaining process operations of the embodiment of FIG. 2 are identical to FIG. 1 and therefore, will not be described in detail again.

In some embodiments of the present invention, as shown, for example, in the embodiment of FIG. 3, extractive fermentation can employ a fatty acid extractant 28' that is derived from a biomass source that is the same or different from the biomass source of feedstock 12, but that is not derived from the actual oil contained in feedstock 12. For example, in the instance when feedstock 12 is corn, fatty acid extractant 28' can be derived from corn oil, but the corn oil producing extractant 28' is not the corn oil contained in feedstock 12 and separated to reaction vessel 40 as provided in the embodiment of FIG. 1. As another example, fatty acid extractant 28' can be derived from soybeans (or soya) as the biomass source, whereas the biomass source of feedstock 12 is corn. Any possible combination of different biomass sources for extractant 28' versus feedstock 12 can be used, as should be apparent to one of skill in the art.

In some embodiments, fatty acid extractant 28' is derived from any native oil and therefore, can be derived from either a biomass source or alternatively, an animal source.

In the embodiment of FIG. 3, liquefied aqueous stream 22 is fed to fermentation vessel 30 along with saccharification enzyme 38 and microorganism 32, whereby a product alcohol is produced by simultaneous saccharification and fermentation (SSF). In some embodiments, saccharification can occur in a separate vessel such as described with reference to the embodiment of FIG. 2, for example. In some embodiments, preferably, liquefied aqueous stream 22 has had at least oil 26 removed via separator 20 (see FIG. 1) and in some embodiments, also has the undissolved solids removed as wet cake 24, prior to introduction to fermentation vessel 30 (see FIG. 1). A native oil, such as a plant-derived oil, is introduced into reaction vessel 40 as stream 26' along with substance(s) 42 for chemically converting at least a portion of oil 26' to fatty acid extractant 28'. Oil stream 26' is not oil 26 derived from feedstock slurry 16 upstream (see FIG. 1). Any plant-derived oil or other native oil that can be chemically converted to fatty acid extractant 28' for ISPR can be the source of oil stream 26'. Fatty acid extractant 28' from reaction vessel 40 is then introduced to fermentation vessel 30, whereby the product alcohol partitions into the fatty acid extractant 28' to a greater extent that the product alcohol would partition into oil 26' if present in the fermentation vessel.

Thus, in some embodiments, the product alcohol is extracted using fatty acid extractant 28' obtained from a plant-derived oil 26' that that is not the same oil 26 originally introduced in the process via feedstock 12. Optionally, one or more additional extractants 29 can be introduced into fermentation vessel 30 for preferentially partitioning the product alcohol from the aqueous phase. The one or more additional extractants 29 can be an exogenous extractant such as exogenously supplied oleyl alcohol, that was not produced in the process and/or can be another fatty acid extractant. In some embodiments, such other fatty acid extractant 29 can be produced from an oil that is derived from a biomass source that is the same or different from either of the biomass sources of fermentation vessel feed stream 22 and oil stream 26'.

The remaining process operations of the embodiment of FIG. 3 are identical to FIGS. 1 and 2, except for aqueous phase 34 not shown as being fed back to fermentation vessel 30 and therefore, will not be described in detail again. It should be understood, however, that in any of the embodiments presented herein, that all or part of aqueous phase 34 can be recycled, discarded, and/or further treated to remove product alcohol as described above with reference to FIG. 1.

In some embodiments of the present invention, the oil derived from feedstock 12 is not separated in separator 20, but rather is chemically converted into a fatty acid extractant in situ, for example, in feedstock 12 either prior to or during liquefaction, in slurry 16, or in saccharified stream 62 (see FIG. 2). For example, in the embodiment of FIG. 4, feedstock 12 is fed to liquefaction vessel 10 along with appropriate enzyme 14, for example, alpha-amylase, for hydrolyzing the starch in feedstock 12 to produce a liquefied feedstock. Also introduced into liquefaction vessel 10, either before, during, or after liquefaction of feedstock 12, are one or more substances 42 for chemically converting the oil present in feedstock 12 to fatty acid extractant 28. Substances 42 can be introduced to liquefaction vessel 10 either before or after the addition of enzyme 14, and the oil in feedstock 12 can be converted to extractant 28 either before, during, or after liquefaction of feedstock 12. In any case, oil in feedstock 12 is converted to fatty acid extractant 28, such that a biphasic stream 18 exits liquefaction vessel 10. Biphasic stream 18 includes both fatty acid extractant 28 as well as the sugar, water, and undissolved solids forming liquefied aqueous phase 22. In some embodiments, where fatty acid extractant includes fatty acids, aqueous phase 22 of biphasic stream 18 can include glycerol (glycerin) from converting the glycerides in the oil to fatty acids. In some embodiments, such glycerol, if present, can be removed from the stream 18 prior to introduction into fermentation vessel 30.

With reference to FIG. 4, biphasic stream 18 (i.e., streams 22, 28) is contacted with the fermentation broth in fermentation vessel 30 to form a biphasic mixture. In fermentation vessel 30, product alcohol produced by SSF partitions into an organic phase including fatty acid extractant 28. Alternatively, in some embodiments, the process can be modified to include a separate saccharification vessel as discussed in connection with FIG. 2. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIGS. 1-3. Optionally, one or more additional extractants 29 can be introduced into fermentation vessel 30 to form an organic phase that preferentially partitions the product alcohol from the aqueous phase. The remaining process operations of the embodiment of FIG. 4 are identical to the previously described figures and therefore, will not be described in detail again.

In some embodiments of the present invention, biomass oil present in feedstock 12 can be separated from the process streams at a step following alcoholic fermentation. The post-fermentation separated oil can then be converted to a fatty acid extractant and introduced as an ISPR extractant in the fermentation vessel. For example, in the embodiment of FIG. 5, feedstock 12 is liquefied to produced feedstock slurry 16 which includes oil 26 derived from the feedstock. Feedstock slurry 16 can also include undissolved solids from the feedstock. Alternatively, the undissolved solids can be separated from slurry 16 via a separator such as a centrifuge (not shown). Feedstock slurry 16 containing oil 26 is introduced directly to fermentation vessel 30 containing a fermentation broth including saccharification enzyme 38 and microorganism 32. A product alcohol is produced by SSF in fermentation vessel 30. Alternatively, in some embodiments, the process can be modified to include a separate saccharification vessel as discussed in connection with FIG. 2.

ISPR extractant 29 is introduced to fermentation vessel 30 to form a biphasic mixture, and the product alcohol is removed by partitioning into the organic phase of the ISPR extractant 29. Oil 26 also partitions into the organic phase. ISPR extractant 29 can be one or more fatty acid extractants and/or exogenous organic extractants not derived from native oil (e.g., oleyl alcohol). If extractant 29 is a fatty acid extractant, the extractant 29 can be fatty acid extractant 28' (see FIG. 3) produced from a native oil such as a plant-derived oil that is not the same oil originally introduced in the process via feedstock 12.

Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIGS. 1-3. Organic phase stream 36 including oil 26 is introduced into a separator 50 to recover product alcohol 54 from extractant 29. The resulting alcohol-lean extractant 27 includes recovered extractant 29 and oil 26. Extractant 27 including oil 26 is introduced into reaction vessel 40 and contacted with one or more substances 42 (e.g., reactants and/or solvents) which chemically convert at least a portion of oil 26 into fatty acid extractant 28.

Extractant 27 including into fatty acid extractant 28 can then be recycled back into fermentation vessel 30. Such recycled extractant stream 27 can be a separate stream or a combined stream with fresh, make-up extractant stream 29. The subsequent withdrawal of alcohol-containing organic phase 36 can then include fatty acid extractant 28 and ISPR extractant 29, in addition to oil 26 and the product alcohol. Organic phase 36 can then be treated to recover the product alcohol, react the oil to form a fatty acid extractant, and be recycled back into fermentation vessel 30 as the resulting alcohol-lean fatty acid extractant 28 and alcohol-lean extractant 29. In some embodiments, use of extractant 29 can be phased out as the fermentation process is operated over time, because the process itself can produce a sufficient amount of fatty acid extractant 28 for extracting the product alcohol. Thus, the ISPR extractant can be recycled extractant 27 and fatty acid extractant 28 as a make up ISPR extractant via reaction vessel 40.

Alternatively, in some embodiments, organic phase stream 36 including oil 26 can be introduced into reaction vessel 40 prior to product alcohol recovery 54 in separator 50. In such embodiments, organic phase stream 36 can be introduced in reaction vessel 50 and contacted with one or more substances 42 for producing fatty acid extractant 28. The resulting organic phase stream 36 including fatty acid extractant 28 can then be introduced into separator 50 to recover product alcohol 54, and the resulting alcohol-lean extractant can then be recycled back into fermentation vessel 30 as extractant stream 27 including fatty acid extractant 28. In still other embodiments, oil 26 can be separated from organic phase stream 36 or extractant stream 27 prior to contacting oil 26 with substance(s) 42 for producing fatty acid extractant 28. Fatty acid extractant 28 can then be used as an ISPR extractant fed to fermentation vessel 30, a different fermentation vessel (e.g., operating in parallel or in series with fermentation vessel 30 in an alcohol manufacturing plant), or stored for later use.

Thus, FIGS. 1-5 provide various non-limiting embodiments of methods and systems involving fermentation processes and fatty acid extractants 28 produced from biomass-derived oil 26, and fatty acid extractants 28' produced from native oil such as plant-derived oil 26' that can be used to remove product alcohol in extractive fermentation. These fatty acid extractants 28 and 28' may be selected from the group consisting of fatty acids, fatty alcohols, fatty amides, fatty acid methyl esters, fatty acid glycol esters, triglycerides, and mixtures thereof. The triglycerides may be hydroxylated or alkoxylated (e.g., methoxylated, ethoxylated). Chemical conversion of glycerides from native oil to the fatty acid extractants described herein can be conducted using any reaction scheme known in the art. With reference to plant-derived oil such as corn oil, for example, in some embodiments, hydroxylated triglycerides as a fatty acid extractant 28 or 28' can be produced by contacting corn oil as oil 26 or 26' with various reactants and solvents 42 (see Example 1 below for details) to achieve hydroxylation shown in Equation I:

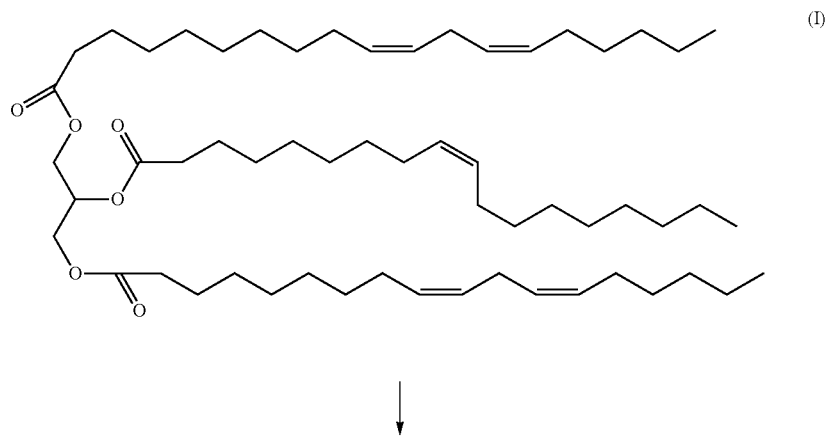

(I)

-continued

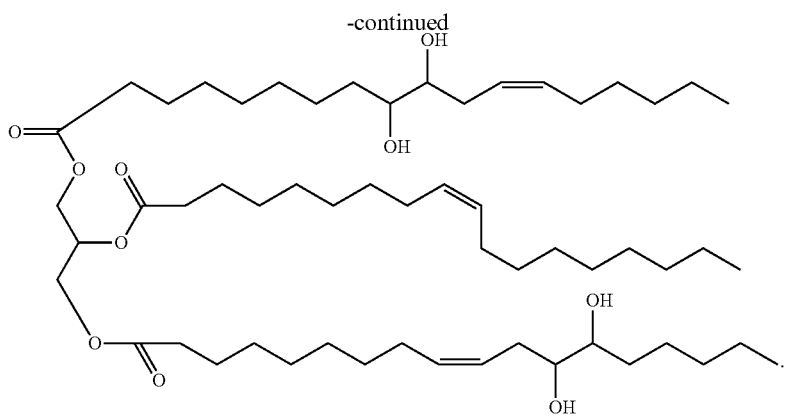

In some embodiments, corn oil triglycerides as oil 26 or 26' can be reacted with aqueous ammonium hydroxide as reactant 42 to obtain fatty amide and fatty acid, which together or separately can be used as fatty acid extractants 28 or 28', as described in Roe, et al., Am. Oil Chem. Soc. 29:18-22, 1952, and shown in Equation II, for example:

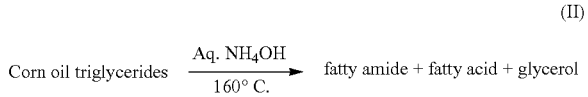
(II)

In some embodiments, aqueous ammonium hydroxide is about 28 wt % ammonia in water. In some embodiments, the mixture of corn oil fatty amides and corn oil fatty acids produced according to Equation (II) can be used to produce a single fatty acid extractant 28 or 28'. In some embodiments, the mixture of fatty amides and fatty acids can include linoleamide, linoleic acid, oleamide, oleic acid, palmitamide, palmitic acid, stearamide, and stearic acid. In such embodiments, such mixture can be composed of about 37 wt % linoleamide, about 18% linoleic acid, about 19 wt % oleamide, about 9 wt % oleic acid, about 8.7 wt % palmitamide, about 4.3 wt % palmitic acid, about 1.2 wt % stearamide, and about 0.7 wt % stearic acid. It should be understood that other composition amounts are possible and can depend on the naturally-occurring amounts of linoleic acid, oleic acid, palmitic acid, and stearic acid in the corn oil used. For example, it would be expected that high-oleic corn oil as oil 26 or 26', which can have, for example, up to about 65 wt % oleic acid content, would produce a mixture that is higher in oleamide and oleic acid pursuant to the reaction of Equation (II) than would be produced when using normal corn oil which is about 24 wt % oleic acid content. In some embodiments, corn oil fatty amides and corn oil fatty acids produced according to Equation (II) can be mixed with fatty acids to vary the ratio of fatty amide to fatty acid in the fatty acid extractant 28 or 28'. In some embodiments, a mixture of fatty amide to fatty acid can be in a ratio of about 2:1 to about 1:2 mixture.

In some embodiments, pure corn oil fatty amides as fatty acid extractant 28 or 28' can be synthesized from corn oil as oil 26 or 26' using as substances 42 anhydrous ammonia as reactant with ammonium acetate as a catalyst, as described in Kohlhase, et al., J. Am. Oil Chem. Soc. 48:265-270, 1971, for example. In some embodiments, the pure corn oil fatty amides can include linoleamide, oleamide, palmitamide, and stearamide. In such embodiments, the pure corn oil fatty amides can be composed of about 55 wt % linoleamide, about 28 wt % oleamide, about 13 wt % palmitamide, and about 2 wt % stearamide. As noted above, it should be understood that other composition amounts are possible and can depend on the naturally-occurring amounts of linoleic acid, oleic acid, palmitic acid, and stearic acid in the corn oil used.

In some embodiment, fatty acid extractant 28 or 28' can include fatty amide of the formula $R(C=O)N(R')(R'')$, wherein R is independently selected from the group consisting of $C_3$ to $C_{27}$ alkyl groups optionally interrupted with one or more double bonds, and R' and R'' are independently selected from the group consisting of hydrogen and $C_1$-$C_6$ alkyl groups optionally containing one or more hydroxyl groups.

In some embodiments, corn oil fatty acids as a fatty acid extractant 28 or 28' can be synthesized from corn oil as oil 26 or 26' by base hydrolysis using NaOH and water as substances 42 (see, e.g., Example 4 below), according to the reaction of Equation III, for example:

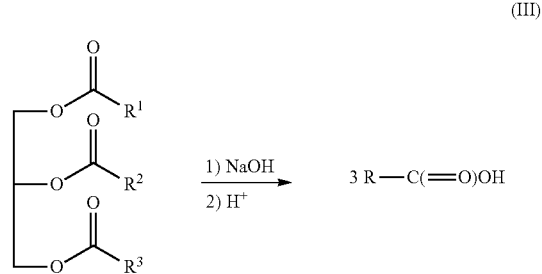
(III)

In some embodiments, pure corn oil fatty amides and pure corn oil fatty acids can be mixed to produce a single fatty acid extractant 28 or 28'. Such mixture of fatty amide to fatty acid can be a 2:1 mixture, and a 1:2 in other embodiments, for example.

In some embodiments, fatty alcohols as fatty acid extractant 28 or 28' can be produced from corn oil as oil 26 or 26' by reduction using tetrahydrofuran (THF) and $LiAlH_4$ as substances 42 (see, e.g., Example 3 below), according to the reaction of Equation IV, for example:

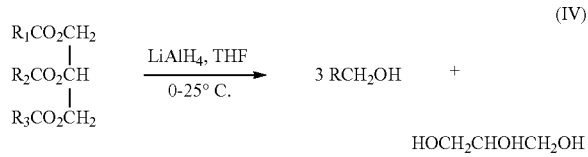

$$R_1CO_2CH_2$$
$$R_2CO_2CH \xrightarrow[0-25°\text{ C.}]{\text{LiAlH}_4, \text{THF}} 3\ RCH_2OH\ +\ \text{HOCH}_2\text{CHOHCH}_2\text{OH} \quad (IV)$$
$$R_3CO_2CH_2$$

In some embodiments, corn oil as oil 26 or 26' can be contacted with methanol and an acid catalyst as substances 42 to produce fatty acid esters as fatty acid extractant 28 or 28'. For example, corn oil can be reacted with an alcohol including, but not limited to, an alcohol of eight carbons or less, in the presence of sulfuric acid to yield fatty acid esters (see, e.g., Example 4 below), according to the reaction of Equation V:

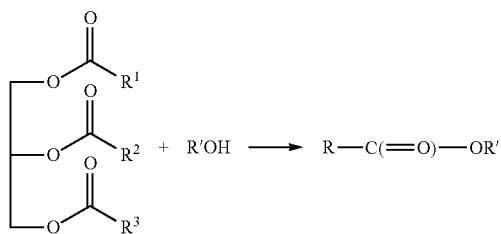

In some embodiments, corn oil as oil 26 or 26' can be converted to corn oil ethylene glycol ester (FAGE) as fatty acid extractant 28 or 28' by producing fatty acid methyl esters (FAME) (see Equation V, above) and further reacting FAME with ethylene glycol as an additional substance 42 (see, e.g., Example 5 below), according to the reaction of Equation VI, for example:

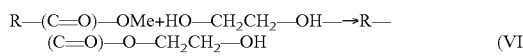

In some embodiments, fatty alcohols may be hydroxylated and may used as extractants. For example, fatty alcohols may be reacted with peracetic acid and then with an aqueous acid to hydroxylate the double bonds along the chain (see, e.g., Example 8) as shown in Equation VII:

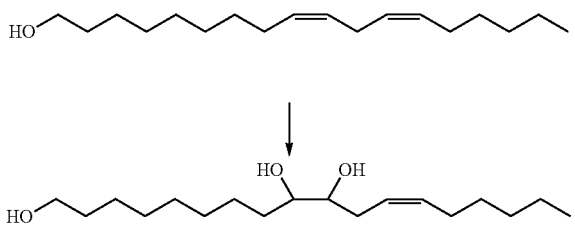

In some embodiments, the extractant may be a liquid or solid such as beads. An extractant that would be available in a solid form such as beads could be easily handled during the manufacturing process. In addition, the product alcohol (e.g., butanol) could be recovered from this extractant, for example, by gas stripping, dissolving in another solvent, or any other applicable method known to one skilled in the art.

In some embodiments, including any of the aforementioned embodiments described with reference to FIGS. 1-5, the fermentation broth in fermentation vessel 30 includes at least one recombinant microorganism 32 which is genetically modified (that is, genetically engineered) to produce butanol via a biosynthetic pathway from at least one fermentable carbon source into butanol. In particular, recombinant microorganisms can be grown in a fermentation broth which contains suitable carbon substrates. Additional carbon substrates may include, but are not limited to, monosaccharides such as fructose; oligosaccharides such as lactose maltose, or sucrose; polysaccharides such as starch or cellulose; or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Application Publication No. 2007/0031918 A1, which is herein incorporated by reference. In addition to an appropriate carbon source (from aqueous stream 22), fermentation broth must contain suitable minerals, salts, cofactors, buffers, and other components, known to those skilled in the art, suitable for the growth of the cultures and promotion of an enzymatic pathway comprising a dihydroxyacid dehydratase (DHAD).

Recombinant microorganisms to produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula,* or *Saccharomyces.* In one embodiment, recombinant microorganisms can be selected from the group consisting of *Escherichia coli, Lactobacillus plantarum,* and *Saccharomyces cerevisiae.* In one embodiment, the recombinant microorganism is a crabtree-positive yeast selected from *Saccharomyces, Zygosaccharomyces, Schizosaccharomyces, Dekkera, Torulopsis, Brettanomyces,* and some species of *Candida.* Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii,* and *Candida glabrata*. For example, the production of butanol utilizing fermentation with a microorganism, as well as which microorganisms produce butanol, is known and is disclosed, for example, in U.S. Patent Application Publication No. 2009/0305370, herein incorporated by reference. In some embodiments, microorganisms comprise a butanol biosynthetic pathway. Suitable isobutanol biosynthetic pathways are known in the art (see, e.g., U.S. Patent Application Publication No. 2007/0092957, herein incorporated by reference). In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in U.S. Patent Application Publication No. 2009/0305363, herein incorporated by reference.

Construction of certain strains, including those used in the Examples, is provided herein.

Construction of *Saccharomyces Cerevisiae* Strain BP1064 and Isobutanologen BP1083 (NGCI-070)

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, the construction of which is described in U.S. Patent Application No. 61/246,844, filed Sep. 29, 2009, herein incorporated by reference.) and pLH468 (SEQ ID NO: 2) to create isobutanologen strain NGCI-070 (BP1083).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 by upstream of the URA3 gene) and terminator (150 by downstream of the URA3 gene). Fragments A and C, each 500 by long, corresponded to the 500 by immediately upstream of the target gene (Fragment A) and the 3' 500 by of the target gene (Fragment C). Fragments A and C were used for integration of the cassette into the chromosome by homologous recombination. Fragment B (500 by long) corresponded to the 500 by immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 by region of the gene was also deleted. For integration of genes using this method, the gene to be integrated was included in the PCR cassette between fragments A and B.

URA3 Deletion

To delete the endogenous URA3 coding region, a ura3::loxP-kanMX-loxP cassette was PCR-amplified from pLA54 template DNA (SEQ ID NO: 3). pLA54 contains the K. lactis TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+ G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1% ) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 138) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 139) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccharomyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 by upstream and 150 by downstream of the URA3 coding region from *Saccharomyces cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass,). Genomic DNA was prepared using a Gentra® Puregene® Yeast/Bact. kit (Qiagen, Valencia, Calif.). The PCR product and pUC19 (SEQ ID NO: 140) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 141) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 142) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of Strains NYLA74 and NYLA83

Insertion-inactivation of endogenous PDC1 and PDC6 genes of S. cerevisiae. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from Achromobacter xylosoxidans (disclosed in U.S. Patent Application Publication No. 2009/0269823) was cloned. The coding region of this gene called sadB for secondary alcohol dehydrogenase (SEQ ID NO: 69) was amplified using standard conditions from A. xylosoxidans genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into E. coli Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in Saccharomyces cerevisiae (Ma, et al., Gene 58:201-216, 1987) as follows. The yeast-E. coli shuttle vector pRS425::GPM::kivD::ADH which contains the GPM1 promoter (SEQ ID NO: 72), kivD coding region from Lactococcus lactis (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 μg of the remaining vector fragment was transformed into S. cerevisiae strain BY4741 along with 1 μg of sadB PCR product. Transformants were selected on synthetic complete medium lacking leucine. The proper recombination event, generating pRS425::GPM-sadB (SEQ ID NO: 124), was confirmed by PCR using primers N142 and N459 (SEQ ID NOs: 108 and 109).

Construction of pdc6::P$_{GPM1}$-sadB Integration Cassette and PDC6 Deletion

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO:80) contains the URA3 marker from pRS426 (ATCC No. 77107) flanked by 75 by homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3'~50 by regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH 1 t.

Construction of pdc1:: PPDC1-ilvD Integration Cassette and PDC1 Deletion

A pdc1:: PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 110, 111, 112, and 113).

The outer primers for the SOE PCR (114117-27A and 114117-27D) contained 5' and 3'~50 by regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: PGPM1-sadB-ADH1t pdc1:: PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 by homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: PGPM1-sadB-ADH1t pdc1:: PPDC1-ilvD-FBA1t Δhis3.

Construction of pdc5::kanMX integration cassette and PDC5 deletion

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6:: PGPM1-sadB-ADH1t pdc1::PPDC1-ilvD-FBA1t Δhis3 pdc5::kanMX4. The strain was named NYLA74.

Deletion of HXK2 (hexokinase II)

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6::PGPM1-sadB-ADH1t pdc1:: PPDC1-ilvD-FBA1t Δhis3 Δhxk2.

Construction of NYLA93

Described below is insertion-inactivation of endogenous PDC1, PDC5, and PDC6 genes of S. cerevisiae. PDC1, PDC5, and PDC6 genes encode the three major isozymes of pyruvate decarboxylase. The resulting PDC inactivation strain was used as a host for expression vectors pYZ067 (SEQ ID NO: 129) and pYZ090 (SEQ ID NO: 1), the construction of which is described in U.S. Provisional Patent Application No. 61/246,844, filed Sep. 29, 2009, herein incorporated by reference.

Deletion of NAD-dependent glycerol 3-phosphate dehydrogenase

A gpd2::loxP-URA3-loxP cassette was PCR-amplified from pUC19::loxP-URA3-loxP plasmid template using Phusion® DNA polymerase (New England BioLabs Inc., Ipswich, Mass.) and primers LA512 and LA513 (SEQ ID NOs: 8 and 9) which generated a ~1.6 kb PCR product. pUC19::loxP-URA3-loxP (SEQ ID NO: 130) contains the URA3 marker from (ATCC No. 77107) flanked by loxP recombinase sites. The GPD2 portion of each primer was derived from the 5' region upstream of the GPD2 promoter and 3' region downstream of the coding region such that integration of the loxP-URA3-loxP marker results in replacement of the GPD2 coding region. The PCR product was transformed into NYLA83 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the GPD2 locus with replacement of the HXK2 coding region using primers LA516 and N175 (SEQ ID NO: 132 and 101). The URA3 marker is recycled by transformation with pRS423::P$_{GAL1}$-cre (SEQ ID NO: 131) and plating on synthetic complete media lacking histidine supplemented with 2% glucose at 30° C. Colonies are patched onto YP (1% galactose) plates at 30° C. to induce URA3 marker excision and are transferred onto YPD plates at 30° C. for recovery. Removal of the URA3 marker is confirmed by patching colonies from the YPD plates onto synthetic complete media lacking uracil to verify the absence of growth. The identified correct clones have the genotype: BY4700 pdc6:: P$_{GPM1}$-sadB-ADH1t pdc1:: P$_{PDC1}$-ilvD-FBA1t Δhis3 Δhxk2 Δgpd2::loxP. The strain was named NYLA92.

Construction of pdc5::loxP-kanMX-loxP integration cassette and PDC5 deletion

A pdc5::loxP-kanMX-loxP cassette was PCR-amplified from plasmid pUC19::loxP-kanMX-loxP (SEQ ID NO: 135) using Phusion® DNA polymerase (New England BioLabs Inc., Ipswich, Mass.) and primers LA249 and LA397 (SEQ ID NOs: 136 and 137) which generated a ~2.2 kb PCR product. pUC19::loxP-kanMX-loxP (SEQ ID NO: 135) contains the kanMX gene from pFA6 (Wach, et al., Yeast 10:1793-1808, 1994) and K. lactis TEF1 promoter and terminator flanked by loxP recombinase sites. The PDC5 portion of each primer was derived from the 5' region upstream of the PDC5 promoter and 3' region downstream of the coding region such that integration of the loxP-kanMX-loxP marker results in replacement of the PDC5 coding region. The PCR product was transformed into NYLA92 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC5 locus with replacement of the PDC5 coding region using primers LA363 and LA364 (SEQ ID NOs: 133 and 134). The identified correct transformants have the genotype: BY4700 pdc6:: P$_{GPM1}$-sadB-ADH1t pdc1::P$_{PDC1}$-ilvD-FBA1t Δhis3 Δhxk2 Δgpd2::loxP Δpdc5:loxP-kanMX-loxP. The strain was named NYLA93.

NYLA93 (pYZ067/pYZ090)

Plasmid vectors pYZ067 and pYZ090 were simultaneously transformed into strain NYLA93 (BY4700 pdc6:: P$_{GPM1}$-sadB-ADH1t pdc1:: P$_{PDC1}$-ilvD-FBA1t Δhis3 Δhxk2 Δgpd2::loxP Δpdc5:loxP-kanMX-loxP) using standard genetic techniques (Methods in Yeast Genetics, 2005, Cold Spring Harbor Laboratory Press, Cold Spring Harbor, N.Y.) and the resulting strain (isobutanologen NYLA93, also referred to as NGCI-065) was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, ketoisovalerate decarboxylase (KivD) and horse liver alcohol dehydrogenase (HADH) in yeast.

Coding regions for Lactococcus lactis ketoisovalerate decarboxylase (KivD) and horse liver alcohol dehydrogenase (HADH) were synthesized by DNA2.0 based on codons that were optimized for expression in Saccharomyces cerevisiae (SEQ ID NO: 71 and 117, respectively) and provided in plasmids pKivDy-DNA2.0 and pHadhy-DNA2.0. The encoded proteins are SEQ ID NOs: 116 and 118, respectively. Individual expression vectors for KivD and HADH were constructed. To assemble pLH467 (pRS426::P$_{TDH3}$-kivDy-TDH3t), vector pNY8 (SEQ ID NO: 120; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 121) from pNY8 was PCR amplified to add an AscI site at the 5' end, and an SpeI site at the 3' end, using 5' primer OT1068 and 3' primer OT1067 (SEQ ID NOs: 122 and 123). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::P$_{TDH3}$-kivDy-TDH3t). pLH467 was verified by restriction mapping and sequencing.

pLH435 (pRS425::P$_{GPM1}$-Hadhy-ADH1t) was derived from vector pRS425::GPM-sadB (SEQ ID NO: 78) which is described in U.S. Provisional Patent Application No. 61/058970, Example 3, which is herein incorporated by reference. pRS425::GPM-sadB is the pRS425 vector (ATCC No. 77106) with a chimeric gene containing the GPM1 promoter (SEQ ID NO: 72), coding region from a butanol dehydrogenase of Achromobacter xylosoxidans (sad B; DNA SEQ ID NO: 69; protein SEQ ID NO: 70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO: 125 and 126) to generate vector pRS425-GPMp-sadB-NheI, which was verified by sequencing. pRS425::P$_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the P$_{TDH3}$-kivDy-TDH3t cassette together with the SalI-NotI fragment from pLH435 that contains the P$_{GPM1}$-Hadhy-ADH1t cassette in a triple ligation reaction. This yielded the vector pRS411::P$_{TDH3}$-kivDy-P$_{GPM1}$-Hadhy (pLH441), which was verified by restriction mapping.

In order to generate a co-expression vector for all three genes in the lower isobutanol pathway: ilvD, kivDy and Hadhy, pRS423 FBA ilvD(Strep) (SEQ ID NO: 127) was used, which is described in U.S. Provisional Patent Application No. 61/100,792, as the source of the IlvD gene. This shuttle vector contains an F1 origin of replication (nt 1423 to 1879) for maintenance in E. coli and a 2 micron origin (nt 8082 to 9426) for replication in yeast. The vector has an FBA1 promoter (nt 2111 to 3108; SEQ ID NO: 119) and FBA terminator (nt 4861 to 5860; SEQ ID NO: 128). In addition, it carries the His marker (nt 504 to 1163) for selection in yeast and ampicillin resistance marker (nt 7092 to 7949) for selection in E. coli. The ilvD coding region (nt 3116 to 4828; SEQ ID NO: 1154 protein SEQ ID NO: 115) from Streptococcus mutans UA159 (ATCC No. 700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-IlvD(Streptococcus mutans)-Lumio) with SacI and SacII (with SacII site blunt ended using T4 DNA polymerase), to give a vector with total length of 9,482 bp. The second step was to isolate the kivDyhADHy cassette from pLH441 with SacI and KpnI (with KpnI site blunt ended using T4 DNA polymerase) which gives a 6,063 by fragment. This fragment was ligated with the 9,482 by vector fragment from pRS423-FBA(SpeI)-IlvD (*Streptococcus mutans*)-Lumio. This generated vector pLH468 (pRS423::P$_{FBA1}$/-ilvD(Strep)Lumio-FBA1t-P$_{TDH3}$-kivDy-TDH3t-P$_{GPM1}$-hadhy-ADH1t), which was confirmed by restriction mapping and sequencing.

pYZ090 and pYZ067 pYZ090 was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of acetolactate synthase (ALS), and a chimeric gene having the coding region of the ilvC gene from *Lactococcus lactis* (nt 3634-4656) expressed from the yeast ILV5 promoter (2433-3626) and followed by the ILV5 terminator (nt 4670-5292) for expression of keto-acid reductoisomerase (KARI).

pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of DHAD, 2) the coding region for HADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lactococcus lactis* (nt 7175-8821) expressed from the yeast TDH3 promoter (nt 8830-9493) followed by the TDH3 terminator (nt 5682-7161) for expression of ketoisovalerate decarboxylase.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention, in which partition coefficients of fatty acid extractants for butanol are demonstrated. It should be understood that, while the above-mentioned chemical conversions and the following examples involve corn oil as the plant-derived oil for producing fatty acid extractants, other native oils such as plant-derived oils may be used without departing from the present invention. From the above discussion and these Examples, one skilled in the art can ascertain essential characteristics of the present invention and can make various changes and modifications of the invention to adapt to various uses and conditions without departing from the present invention.

As used herein, the meaning of abbreviations used was as follows: "g" means gram(s), "kg" means kilogram(s), "L" means liter(s), "mL" means milliliter(s), "mL/L" means milliliter(s) per liter, "mL/min" means milliliter(s) per min, "μL" means microliter(s), "DI" means deionized, "uM" means micrometer(s), "nM" means nanometer(s), "w/v" means weight/volume, "GC" means gas chromatograph, "OD" means optical density, "OD$_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

Examples 1-6 describe exemplary methods for chemically converting corn oil into the following fatty acid extractants: hydroxylated triglycerides (Example 1), fatty amides and mixtures with fatty acids (Example 2), fatty alcohols (Example 3), fatty acids (Example 4), fatty acid methyl esters (Example 5); and fatty acid glycol esters (Example 6). Example 7 provides a series of comparative examples of extractive fermentation experiments that were conducted using the water-immiscible extractants listed in Tables 3 and 7-10, for which the performance data are summarized in Table 11.

Example 1

Hydroxylated Triglycerides from Corn Oil

A. Corn Oil hydroxylation (63% hydroxylation)

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% H$_2$O$_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. NaHCO$_3$ solution (50 mL), and brine (50 mL). The organic layer was dried over anh. Na$_2$SO$_4$ and concentrated in vacuo to obtain 48.9 g of yellow oil. The $^1$H NMR analysis of the crude reaction product showed that 63% of double bonds were epoxidized.

To a 500 mL round bottom flask was added epoxidized corn oil (20.0 g), tetrahydrofuran (THF) (100.0 mL), and sulfuric acid (50 mL of 1.7 M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. Na$_2$SO$_4$ and concentrated in vacuo to obtain 19.9 g of dark yellow oil (63% hydroxylation corn oil).

B. Corn Oil Hydroxylation (47% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% H$_2$O$_2$ in water) was added dropwise over one hour. The mixture was stirred at 60° C. for one hour, upon which time the reaction mixture was worked up: the resin was removed by filtration, and the filtrate partitioned between ethyl acetate (75 mL) and water (50 mL). After the layers were separated, the organic layer was washed with sat. aq. NaHCO$_3$ solution (50 mL), and brine (50 mL). The organic layer was dried over anh. Na$_2$SO$_4$ and concentrated in vacuo to obtain 49.8 g of yellow oil. The $^1$H NMR analysis of the crude reaction product showed that 47% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.2 g of dark yellow oil (47% hydroxylation corn oil).

C. Corn Oil Hydroxylation (28% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 47.2 g of yellow oil. The $^1H$ NMR analysis of the crude reaction product showed that 28% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 20.3 g of dark yellow oil (28% hydroxylation corn oil).

Partition coefficient measurement

To a 5 mL vial was added 0.910 g of the 67% hydroxylated corn oil, and 0.910 mL of 3wt % iBuOH water solution. The biphasic mixture was vigorously stirred using Vortex Genie® for 10 minutes. Upon mixing, the separation of layers was aided by centrifuging the mixture using Fisher Scientific Centrific 228 centrifuge (3300 rpm) for 10 minutes. 0.100 g of both layers were taken. The organic, upper layer was diluted to 1.00 mL with toluene solution of ethylene glycol diethylether (10.1 mg/mL), and the water layer was diluted to 1.00 mL with methanol solution of ethylene glycol diethylether (10.2 mg/mL). The concentrations of i-BuOH in both phases were measured using a calibrated gas chromatograph (GC). The same procedure was repeated for 47% and 28% hydroxylated corn oil. The partition coefficient thus measured was 3.2 for the 67% hydroxylated corn oil, 2.3 for the 47% hydroxylated corn oil, and 2.1 for the 28% hydroxylated corn oil.

The above outlined procedure was repeated with 6% i-BuOH water solution. The partition coefficients for 67% -, 47% -, and 28% -hydroxylated corn oils were 2.9, 2.9, and 2.0, respectively.

Example 2

Fatty Amides Plus Fatty Acids, and Pure Fatty Amides from Corn Oil

Corn oil was reacted with aqueous ammonium hydroxide in a manner similar to that described by Roe, et al., J. Am. Oil Chem. Soc. 29:18-22, 1952. Mazola® corn oil (0.818 L, 755 g) was placed in a 1 gallon stainless steel reactor to which was added 1.71 L (1540 g) of aqueous ammonium hydroxide (28% as $NH_3$). The reactor was heated with stirring to 160° C. and was maintained at that temperature with stirring for 7 h during which time the pressure reached 400 psi. The reactor was cooled and the product, a creamy white solid, was removed and the reactor rinsed with ethyl acetate. The product was dissolved in 5 L ethyl acetate and washed 5 times with 500 mL each of water which was neutralized with $H_2SO_4$. The ethyl acetate was then dried over anhydrous $Na_2SO_4$ and the solvent removed on a rotary evaporator leaving a light brown soft solid.

$^{13}C$ NMR in $CDCl_3$ indicated that the product contained an approximate 2:1 ratio of fatty amide to fatty acid and that the conversion of the corn oil to product was quantitative. The product had a melting point of 57-58° C., but dropped about 11° C. when saturated with water.

Pure corn oil fatty amide was synthesized from corn oil according to Kohlhase, et al., J. Am. Oil Chem. Soc. 48:265-270, 1971 using anhydrous ammonia with ammonium acetate as a catalyst.

Three grams of ammonium acetate were placed in a 400 mL stainless steel shaker tube to which was added 51.8 g of corn oil. Anhydrous ammonia (89.7 g) was then added and the reactor sealed and heated for 7 h at 125° C. during which time the pressure reached 1300 psi. The reactor was cooled, the light colored solid removed and the reactor rinsed with ethyl acetate. The product dissolved in ethyl acetate was then worked up as in the case of the fatty amide/fatty acid mixture above.

Fatty acids were synthesized from corn oil by base hydrolysis using NaOH as described below in Example 4.

Three preparations: (1) the 2:1 mixture of corn oil fatty amide and corn oil fatty acid from aqueous ammonia, (2) a 2:1 mixture of pure corn oil fatty amide:pure corn oil fatty acid, and (3) a 1:2 mixture of pure corn oil fatty amide:corn oil fatty acid, were all tested for their ability to extract isobutanol from a 3% solution in water. Seven hundred milligrams of each was added to 2.1 mL of water containing 3% isobutanol in a 20 mL scintillation vial and placed on a rotary shaker overnight at 30° C. In all three cases, the organic phase became liquid at this temperature, indicating a further lowering of the melting point with the uptake of isobutanol. Fifty microliters of the upper phase were diluted with either 200 μL of toluene containing ethylene glycol diethylether (10.068 mg/mL) as a GC standard or 200 μL of isopropanol containing the same concentration of ethylene glycol diethylether. Fifty microliters of the lower phase was diluted with 150 μL of methanol and 50 μL of isopropanol containing the same concentration of ethylene glycol diethylether. The concentrations of isobutanol in both phases were determined using a calibrated GC. The partition coefficients measured were as follows: 3.81 for (1), 4.31 for (2), and 3.58 for (3).

Fatty amide/fatty acid aqueous ammonia preparation (1), and a preparation (1 a) constituted by preparation (1) mixed 1:1 with pure corn oil fatty acid (equivalent to 1:2 fatty amide: fatty acid) were incubated in shake flasks with fermentation broth containing the *Saccharomyces* butanologen NGCI-070 at a ratio of 3 parts broth to 1 part amide/acid mixture. Preparation (1) was a soft solid, while preparation (1a) was a liquid at 30° C. Starting at a glucose concentration of 8.35 g/L, the shake flasks were then incubated for 25 h on an incubator shaker and the consumption of glucose followed as a function of time. Table 1 indicates that the fatty amide/fatty acid mixtures at both ratios were not toxic to the butanologen and even showed higher rates of glucose uptake than with oleyl alcohol.

TABLE 1

| Flask | Glucose conc. (g/L) | | |
|---|---|---|---|
| | Time = 0 | 18 hrs | 25 hrs |
| Oleyl Alcohol | 8.35 | 4.26 | 0 |
| Oleyl Alcohol | 8.35 | 4.46 | 0 |
| 2:1 Synthesized Fatty Amide:Fatty Acid Mix (Preparation (1)) | 8.35 | 3.06 | 0 |
| 2:1 Synthesized Fatty Amide:Fatty Acid Mix (Preparation (1)) | 8.35 | 3.22 | 0 |
| 1:1 Synthesized Fatty Amide Fatty Acid Mix:Pure Fatty Acids (Preparation (1a)) | 8.35 | 2.73 | 0 |
| 1:1 Synthesized Fatty Amide Fatty Acid Mix:Pure Fatty Acids (Preparation (1a)) | 8.35 | 2.73 | 0 |

Example 3

Fatty Alcohols from Corn Oil

With reference to the reaction of Equation IV above for producing fatty alcohols from corn oil, a 22 L, round-bottom flask equipped with a mechanical stirrer, reflux condenser with $N_2$ source, addition funnel, internal thermocouple, and rubber septum was flame-dried under nitrogen. The flask was charged with 132 g (3.30 moles) of 95% lithium aluminum hydride powder that is weighed out in a dry box and loaded into a solids addition funnel. The 22 L flask was cooled with an ice bath, and 9.0 liters of anhydrous THF were added into the reactor via a cannula. The resulting slurry was cooled to 0-5° C. and a solution of 956 g (1.10 moles) of Wesson® corn oil in 1.00 liter of anhydrous THF was added dropwise over 2-3 hours while holding the reaction temperature at 5-20° C. After adding the corn oil, the slurry was stirred overnight at ambient temperature. When the reaction was done, as verified by TLC chromatography, it was quenched by the dropwise addition of a solution of 130 g of water dissolved in 370 mL of THF. Then 130 g of 15% aqueous NaOH solution was added followed by the addition of 400 g of water. The mixture was vigorously stirred while warming to room temperature and produced a white granular solid. The solids were filtered off using a fritted-glass filter funnel and washed with additional THF. The THF was removed on a rotary evaporator and the residue was taken up in 3.00 liters of ethyl acetate. The product solution was washed with 2×1.00 L of water, 1×1.00 L of brine, dried over $Na_2SO_4$, filtered, and concentrated in vacuo to give 836 g (97%) of fatty alcohols as yellow oil. The crude fatty alcohol mixture was then distilled (140° C./1 mmHg), and used in the following partition coefficients experiments.

Partition coefficient experiments

To each of the five 5-mL vials were added 1 mL of fatty alcohol mixture, and 1 mL of 3 wt % iBuOH water solution. The biphasic mixture was vigorously stirred using Vortex Genie® for 10, 20, 30, 40, and 60 minutes, respectively. Upon mixing, the separation of layers was aided by centrifuging the mixture using Fisher Scientific Centrific 228 centrifuge (3300 rpm) for 10 minutes. 0.100 mL of both layers were taken. The organic, upper layer was diluted to 1.00 mL with toluene solution of ethylene glycol diethylether, and the water layer was diluted to 1.00 mL with methanol solution of ethylene glycol diethylether. The concentrations of i-BuOH in both phases were measured using a calibrated GC. The partition coefficient thus measured was 2.70.

The same partition coefficient measurement, as described above was run for 6 wt % i-BuOH concentration. The partition coefficient thus measured was 3.06.

In the following Examples 4-6, the methods used for determination of the partition coefficients of the extractants was the quiescent method. For the quiescent method, 5 mL of either a 3% or 6% (w/v) solution of isobutanol in water was put into a vial and 5 mL of the solvent of interest was carefully added onto the top of the water solution so as not to mix the physical phases. After the indicated period of time, a sample of the clear portion of the solvent phase and of the aqueous phase were removed and analyzed for isobutanol content by GC. Any emulsion layer was ignored for this analysis. For the GC analysis, 100 uL of the sample was added to 400 uL of isopropanol. 500 uL of a solution of diethylene glycol diethyl ether (internal standard) was added and the solution was shot on a Carbowax® column with an FID detector and the concentration of isobutanol was determined.

Other methods known in the art can also be used for determining the partition coefficients of extractants according to the present invention. For example, the shaking method can be used. As an example for the shaking method, 5 mL of either a 3% of 6% (w/v) solution of isobutanol in water can be added to a centrifuge tube along with 5 mL of the solvent of interest. The tube can be shaken vigorously for 1 minute. The tube can be then spun in a centrifuge at approx. 12500 G for 15 minutes. Samples of the clear solvent layer and the clear aqueous layer can be removed and analyzed for isobutanol content by the method described above.

Example 4

Corn Oil Fatty Acids

Round bottom flask (5 L) was equipped with a mechanical stirrer, thermocouple, heating mantle, condenser, and nitrogen tee. Charged with 500 g of food grade corn oil, 1 L of water and 75 g of sodium hydroxide. Mixture was heated to 90° C. and held for three hours, during which time it became a single thick, emulsion-like single phase. At the end of this time, TLC shows no remaining corn oil in the mixture. The mixture was then cooled to 72° C. and 500 mL of 25% sulfuric acid was added to acidify the mixture. It was then cooled to room temperature and 2 L of diethyl ether was added. The ether layer was washed 3×1 L with 1% sulfuric acid, 1×1 L with saturated brine, dried over $MgSO_4$, and filtered. The ether was removed by rotovap and then the oil was purged with nitrogen overnight, obtaining 470 g of a yellow oil that partially crystallized overnight. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids.

The partition coefficient of isobutanol in the COFA/water system at an initial 6% I-BuOH concentration after 168 hours as determined by the quiescent method is 2.8.

Example 5

Corn Oil Fatty Acid Methyl Esters (FAME)

Round bottom flask (5 L) equipped with a mechanical stirrer, thermocouple, heating mantle, condenser, and nitrogen tee. Charged with 1500 g of food grade corn oil, 1500 g of methanol, and 30 g of concentrated sulfuric acid. The mixture was refluxed for 24 hours and followed by thin layer chromatography. The reaction was then cooled and the layers were separated. The organic layer was washed 1×1 L with water, 1×1 L with saturated sodium bicarbonate, 2×1 L with water, 1×1 L with saturated brine, and then dried over $MgSO_4$. The yield was 1416 g of a pale yellow oil. GCMS analysis shows the presence of the methyl esters of the acids 16:0, 18:2, 18:1, 18:0, 20:1, and 20:0. Titration for free fatty acids via AOCS method Ca 5a-40 shows a fatty acid content of 0.2% expressed as oleic acid.

The partition coefficient of isobutanol in the FAME/water system at an initial 6% I-BuOH concentration after 236 hours as determined by the quiescent method is 1.06.

Example 6

Corn Oil Ethylene Glycol Ester (FAGE)

Round bottom flask (3 L) was equipped with a mechanical stirrer, thermocouple, heating mantle, Dean-Stark trap, condenser, nitrogen purge, and nitrogen tee; and charged with 1000 g of Corn Oil Fatty Acid Methyl Ester (FAME) and 1000 g of ethylene glycol. 2 g of clean sodium is added to the mixture and it is heated to 60° C. After 90 minutes, the temperature was increased to 100° C. and nitrogen is slowly sub-surface sparged into the reaction. Methanol is collected in the Dean-Stark trap. The temperature is slowly increased to 160° C. over 3 hours and methanol continues to distill from the reaction. After another two hours, a total of 100 mL of methanol was collected. The reaction was cooled to room temperature and was neutralized with 20 g of 25% sulfuric acid. The layers were separated and the top layer was washed with 4×200 ml of 10% calcium chloride solution. Emulsions were formed but would separate with time. The organic layer was washed with 250 mL of saturated brine, dried over $MgSO_4$, and filtered to give 916 g of a clear yellow oil. Titration for free fatty acids via AOCS method Ca 5a-40 shows 2.9% of acid present—expressed as oleic acid. A sample was silanized by reacting 109 mg with 100 uL of N-methyl-N-(trimethylsilyl)trifluoroacetamide in 1 ml of dry pyridine. GCMS analysis of the silanized product shows the presence of the TMS derivatives of the 16:0, 18:2, and 18:1 acids, along with the 16:0, 18:2, 18:1, and 18:0 ethylene glycol monoesters.

The partition coefficient of isobutanol in the FAGE/water system at an initial 6% I-BuOH concentration after 192 hours as determined by the quiescent method is 2.3.

Example 7

Comparative Fermentation Examples

The materials listed in Table 2 were used in the comparative examples of Example 7. All commercial reagents were used as received. Solvents synthesized from corn oil were also used as received.

TABLE 2

| Materials |
| --- |
| Seed Flask and Fermentation Media Components |
| Yeast Nitrogen Base w/o amino acids, Becton Dickinson and Company (291920) |
| Yeast Dropout Mix, Sigma Aldrich (Y2001) |
| L-Leucine, Sigma Aldrich (L8000) |
| L-Tryptophan, Sigma Aldrich (T0254) |

TABLE 2-continued

| Materials |
| --- |
| Ethanol >99.5%, Sigma Aldrich (459844) |
| 50% w/w glucose solution |
| Ergosterol, Fluka (45480) |
| Tween 80, Sigma Aldrich (P8074) |
| Yeast Extract, Becton Dickinson and Company (212750) |
| Peptone, Becton Dickinson and Company (211820) |
| Nicotinic Acid, Alfa Aesar (Stock # A12683 or L02659) |
| Thiamine Hydrochloride, Sigma Aldrich (T4562) |
| Commercial Solvents |
| 90-95% Oleyl Alcohol, Cognis, Lot # CE81210020 |
| Oleic Acid, Sigma Aldrich (27728) |
| Isofol ™ 12, Sasol North America, Lot # 65604 |
| Synthesized Solvents (using the methods described in above Examples 2-4 and 6) |
| Corn Oil Fatty Acids |
| Corn Oil Ethylene Glycol Ester |
| Corn Oil Fatty Alcohols, Preparation A |
| Corn Oil Fatty Alcohols, Preparation B |
| Corn Oil Fatty Amides/Acids |
| Corn Oil Fatty Amides |
| Corn Oil Fatty Acid Methyl Ester + 1,2-Propanediol |
| Stock Solutions |
| 10X YEP |
| Add 100 g/L yeast extract and 200 g/L peptone in 500 mL of warm $diH_2O$ (60° C.). Continue heating while bringing solution to a final volume of 1 L then filter sterilize. |
| 1% Ergosterol in 50:50 v/v ethanol:tween 80 |
| Add 10 g/L ergosterol into a warm solution (50° C.) of 50:50 ethanol:tween heat until the ergosterol dissolves and filter sterilize. |
| 100X Nicotinic Acid/Thiamine Hydrochloride |
| Add 10 g/L nicotinic acid and 2 g/L thiamine to $diH_2O$ then filter sterilize. |
| Strains |
| NGCI-065 |
| NGCI-070 |

General Methods

Optical density was measured using an Amersham Biosciences Ultrospec 2100 Pro spectrophotometer. Measurements were typically made at a wavelength of 600 nanometers.

Glucose concentrations were measured using a YSI Life Sciences 2700 Select Biochemistry Analyzer. Fermentation samples were centrifuged at 13,200 rpm for 2 minutes in a 1.7 mL microcentrifuge tube and the aqueous supernatant analyzed for glucose concentration.

Fermentation conditions: 30% $pO_2$; temperature: 30° C.; pH 5.5 (unless noted otherwise); initial batch glucose: 20 g/L, maintained during production.

Both HPLC and GC analyses were used for the quantization of isobutanol in the aqueous phase and solvent phase respectively. Isobutanol in the aqueous was measured after filtration through a 0.2 um nylon filter with a HPLC (Agilent 1100, Agilent, Santa Clara, Calif.) under the following conditions:

Column: Bio-Rad, Aminex HPX-87H, No. 125-0143

Mobile Phase: 0.01 M $Na_2HPO_4$, pH=8.0

Injection Volume: 10 uL

Flow Rate: 0.6 mL/min

Run Time: 22.5 minutes

Column Temperature: 65° C.

Detectors: Refractive Index

Detector Temperature: 40° C.

UV Detection: 210 nm, 4 nm bandwidth, Ref 360 nm, 100 nm bandwidth.

The solvent phase was measured with a GC (HP6890, Agilent, Santa Clara, Calif.) under the following conditions:

Column: J&W Scientific DB Waxter (50 m×0.32 mm ID, 1 um film)
Gas Carrier: Helium 4 mL/min
Injection Volume: 2 uL
Make Up Flow Rate: 40 mL/min
Run Time: 29 minutes
Oven Temperature: 40° C. for 5 min, 40° C. to 230° C. @10° C./min., 5 min 230° C.
Injector Split: 1:5 @ 250° C.
Flame Ionization Detection: 250° C.

Comparative Examples

GLNOR635A-640A of Corn Oil Derived Extractants and Their Constituents

A series of comparative examples were conducted using the water-immiscible extractants listed in Table 3. The extractants were added to the fermentor broth at time zero exposing the culture to the solvent for the duration of the fermentation. Isobutanol concentrations in both the aqueous phase and organic phase were measured to calculate the partitioning coefficient of the extraction solvent. Glucose utilization was used to determine the biocompatability of the microorganism to the extractant.

TABLE 3

Composition of Extractants Used for Fermentation Examples GLNOR635-640A

| Example | Extractant |
| --- | --- |
| GLNOR635A | Oleyl Alcohol |
| GLNOR636A | Corn Oil Fatty Acids (COFA) |
| GLNOR637A | Oleic Acid |
| GLNOR638A | Oleic Acid |
| GLNOR639A | Oleic Acid |
| GLNOR640A | Oleic Acid |

The fermentations were carried out as described with the strain NGCI-065. The inoculum was prepared in two stages and incubated at 30° C. and 250 rpm in an incubator shaker (Innova 4200, New Brunswick Scientific, Edison, N.J.). The first stage or pre-seed was inoculated from a frozen glycerol seed stock, two vials were placed into a 250 mL flask with 30 mL of filter sterilized pre-seed media (Table 4) and grown for 24 hours to an OD of approximately 2. 15 mL of the pre-seed was then transferred to a 2 L flask with 270 mL of filter sterilized seed media (Table 5) for the second stage which was incubated for 24 hours. 30 mL of filter sterilized 10×YEP and 300 mL of filter sterilized 90-95% oleyl alcohol was then added and incubated for an additional 24 hours to a final OD of approximately 5-10 in the aqueous phase of the seed culture. For examples GLNOR639 and GLNOR640, the pH was 4.5.

TABLE 4

Pre-seed/Stage 1 Media Composition

| Pre-seed Media Components | Amount per Liter |
| --- | --- |
| Yeast Nitrogen Base w/o Amino Acids | 6.7 g |
| Yeast Dropout Mix | 1.4 g |
| L-Leucine (1% w/v Stock Soln) | 20 mL |

TABLE 4-continued

Pre-seed/Stage 1 Media Composition

| Pre-seed Media Components | Amount per Liter |
| --- | --- |
| L-Tryptophan (1% w/v Stock Soln) | 4 mL |
| Ethanol | 3.0 mL |
| 50% w/w glucose solution | 5.4 mL |

TABLE 5

Seed/Stage 2 Media Composition

| Seed Media Components | Amount per Liter |
| --- | --- |
| Yeast Nitrogen Base w/o Amino Acids | 6.7 g |
| Yeast Dropout Mix | 2.8 g |
| L-Leucine (1% w/v Stock Soln) | 20 mL |
| L-Tryptophan (1% w/v Stock Soln) | 4 mL |
| Ethanol | 3.0 mL |
| 50% w/w glucose solution | 50.4 mL |
| MES Buffer | 38.4 g |

| Additions after 24 hrs of incubation | Amount per Flask |
| --- | --- |
| 10X Yeast Extract Peptone (100 g/L YE and 200 g/L Peptone) | 30 mL |
| 90-95% Oleyl Alcohol | 300 mL |

Fermentation vessels (Applikon AD1010 Bioreactor, Applikon Biotechnology, Dover, N.J.) were sterilized with $diH_2O$ for 30 minutes (Amsco Renaissance 3033 Revas Steam Sterilizer, Steris Corporation, Mentor, Ohio). Once the vessels were finished sterilization in the autoclave and cooled to 30° C., the sterile $diH_2O$ was removed and the filter sterilized fermentation media was added to a volume of 280 mL. 70 mL of the aqueous phase from the second stage seed flasks was added to the fermentation vessel for a final aqueous volume of 350 mL. Immediately after inoculation, 100 mL of 10×YEP media supplementation was added as well as 450 mL of the respective extraction solvent for a final solvent to broth ratio of approximately 1:1. Fermentation set-point conditions were temperature 30° C., $pO_2$ 30%, pH 5.5 for GLNOR635A-638A and pH 4.5 for GLNOR639A-640A. The fermentation was sampled approximately every 8 hours from the time of inoculation to monitor glucose concentration, which was maintained between 5-20 g/L through the addition of 50% w/w glucose solution, and analyzed for isobutanol accumulation in both the aqueous phase and the extractant phase. Enough sample volume was taken at each time point to obtain a sample from both of the phases, then those samples were centrifuged in order to ensure a clean cut of each.

TABLE 6

Fermentation Media Composition

| Fermentation Media Components | Amount per Liter |
| --- | --- |
| Yeast Nitrogen Base w/o Amino Acids | 6.7 g |
| Yeast Dropout Mix | 2.8 g |
| L-Leucine (1% w/v Stock Soln) | 20 mL |
| L-Tryptophan (1% w/v Stock Soln) | 4 mL |

TABLE 6-continued

Fermentation Media Composition

| | Amount per Liter |
|---|---|
| Ethanol | 4.5 mL |
| 50% w/w glucose solution | 40.0 g |
| 1% Ergosterol in 50:50 (v/v) Ethanol:Tween 80 | 1.0 mL |
| Additions Post Inoculation | |
| 10X Yeast Extract Peptone (100 g/L YE and 200 g/L Peptone) | 100 mL |
| 90-95% Oleyl Alcohol | 450 mL |

Comparative Examples

GLNOR661A-666A of Corn Oil Derived Extractants and Their Constituents

Comparative examples GLNOR661A-666A were conducted using the water-immiscible extractants listed in Table 7. The examples in this set were performed the same as in the previous examples GLNOR635A-640A with the exception of the strain, pH, and supplement addition at time zero. Strain NGCI-070 was used, pH set point was 5.5, and 4 mL nicotinic acid/thiamine media supplementation was added instead of 100 mL yeast extract peptone for this series of examples.

TABLE 7

Composition of Extractants Used for Fermentation Examples GLNOR661-666A

| Example | Extractant |
|---|---|
| GLNOR661A | Oleyl Alcohol |
| GLNOR662A | No Solvent |
| GLNOR663A | Corn Oil Fatty Acids |
| GLNOR664A | Corn Oil Fatty Acids |
| GLNOR665A | Oleic Acid |
| GLNOR666A | Oleic Acid |

Comparative Examples

GLNOR690A-695A of Corn Oil Derived Extractants and Their Constituents

Comparative examples GLNOR690A-695A were conducted using the water-immiscible extractants listed in Table 8. The examples in this set were performed the same as in the previous examples GLNOR661A-666A. Strain NGCI-070 was used.

TABLE 8

Composition of Extractants Used for Fermentation Examples GLNOR690-695A

| Example | Extractant |
|---|---|
| GLNOR690A | Oleyl Alcohol |
| GLNOR691A | Oleyl Alcohol |
| GLNOR692A | Corn Oil Fatty Alcohols* |
| GLNOR693A | Corn Oil Fatty Alcohols* |

TABLE 8-continued

Composition of Extractants Used for Fermentation Examples GLNOR690-695A

| Example | Extractant |
|---|---|
| GLNOR694A | Corn Oil Ethylene Glycol Ester |
| GLNOR695A | Corn Oil Ethylene Glycol Ester |

*Synthesized Fatty Alcohols, Preparation A

Comparative Examples

GLNOR721A-726A of Corn Oil Derived Extractants and Their Constituents

Comparative examples GLNOR721A-726A were conducted using the water-immiscible extractants listed in Table 9. The examples in this set were performed the same as in the previous examples GLNOR690A-695A. Strain NGCI-070 was used.

TABLE 9

Composition of Extractants Used for Fermentation Examples GLNOR721-726A

| Example | Extractant |
|---|---|
| GLNOR721A | Corn Oil Fatty Acid Methyl Ester + 1,2-Propanediol |
| GLNOR722A | Corn Oil Fatty Acid Methyl Ester + 1,2-Propanediol |
| GLNOR723A | Corn Oil Fatty Alcohols** |
| GLNOR724A | Corn Oil Fatty Alcohols** |
| GLNOR725A | Corn Oil Fatty Amides/Acids* |
| GLNOR726A | Corn Oil Fatty Amides/Acids* |

*2:1 Synthesized Fatty Amide:Fatty Acid Mix (Preparation (1)) of Example 2
**Synthesized Fatty Alcohols, Preparation B

Comparative Examples

GLNOR749A-754A of Corn Oil Derived Extractants and Their Constituents

Comparative examples GLNOR749A-754A were conducted using the water-immiscible extractants listed in Table 10. The examples in this set were performed the same as in the previous examples GLNOR721A-726A. Strain NGCI-070 was used.

TABLE 10

Composition of Extractants Used for Fermentation Examples GLNOR749-754A

| Example | Extractant |
|---|---|
| GLNOR749A | Isofol ™ 12** |
| GLNOR750A | Isofol ™ 12 |
| GLNOR751A | Corn Oil Fatty Acids |
| GLNOR752A | Corn Oil Fatty Acids |
| GLNOR753A | Corn Oil Fatty Amides/Acids* |
| GLNOR754A | Corn Oil Fatty Amides/Acids* |

*1:1 Synthesized Fatty Amide Fatty Acid Mix:Pure Fatty Acids (Preparation (1a)) of Example 2
**Isofol ™ 12: 2-butyl-1-octanol The performance data for the fermentation examples GLNOR635A-640A, GLNOR661A-666A, GLNOR690A-695A, GLNOR721A-726A, GLNOR749A-754A are summarized in Table 11, which provides the aqueous isobutanol concentrations (g/L), solvent isobutanol concentrations (g/L), and solvent partition coefficients ($K_p$) for the exemplary corn oil derived extractants and their constituents as compared with conventional commercial solvents of oleyl alcohol and Isofol™.

TABLE 11

| Example | Solvent (g/L) | Aqueous (g/L) | Kp |
|---|---|---|---|
| GLNOR635 | 21.5 | 6.4 | 3.38 |
| GLNOR636 | 9.8 | 3.9 | 2.52 |
| GLNOR637 | 5.6 | 2.1 | 2.64 |
| GLNOR638 | 5.5 | 2.1 | 2.56 |
| GLNOR639 | 3 | 1.2 | 2.54 |
| GLNOR640 | 3 | 1.2 | 2.51 |
| GLNOR661 | 19 | 5.7 | 3.35 |
| GLNOR662 | X | 5.1 | X |
| GLNOR663 | 16.3 | 5.9 | 2.76 |
| GLNOR664 | 12.1 | 4.6 | 2.65 |
| GLNOR665 | 12 | 4.6 | 2.61 |
| GLNOR666 | 12.4 | 4.9 | 2.51 |
| GLNOR690 | 14.1 | 3.8 | 3.74 |
| GLNOR691 | 13.6 | 3.6 | 3.77 |
| GLNOR692 | NA | NA | NA |
| GLNOR693 | NA | NA | NA |
| GLNOR694 | 13.4 | 5 | 2.68 |
| GLNOR695 | 12.2 | 4 | 3.07 |
| GLNOR721 | 12.7 | 4.4 | 2.85 |
| GLNOR722 | 11.5 | 4.0 | 2.89 |
| GLNOR723 | 14.5 | 5.0 | 2.88 |
| GLNOR724 | 18.0 | 6.3 | 2.87 |
| GLNOR725 | NA | 6.2 | NA |
| GLNOR726 | NA | NA | NA |
| GLNOR749 | 20.0 | 5.0 | 4.05 |
| GLNOR750 | 20.1 | 4.8 | 4.22 |
| GLNOR751 | X | 1.8 | X |
| GLNOR752 | 14.3 | 6.0 | 2.38 |
| GLNOR753 | 12.0 | 4.3 | 2.81 |
| GLNOR754 | 19.5 | 7.2 | 2.71 |

Example 8

Fatty Alcohol Hydroxylation (65% Hydroxylation)

To a three-neck 250 mL flask, equipped with a mechanical stirrer and addition funnel was added fatty alcohol mixture (43 g, 0.16 mmol), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over 30 minutes. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 50 g of yellow oil. The $^1H$ NMR analysis of the crude reaction product showed that 65% of double bonds were epoxidized. The resulting mixture was taken on to the next step without purification.

To a 500 mL round bottom flask was added epoxidized fatty alcohols (14.5 g), THF (200.0 mL), and sulfuric acid (100 mL of 1.7M aqueous solution). The cloudy mixture was stirred at 50° C. overnight, and then worked up by partitioning between water (100 mL) and ethyl acetate (200 mL). The organic layer was washed with water (2×100 mL), followed by sat. aq. $NaHCO_3$ solution (100 mL), and then brine (100 mL). The organic layer was dried over anh. $Na_2SO_4$ and concentrated in vacuo to obtain 14.7 g of thick clear liquid and white solid mixture.

Measurement of the Partition Coefficient

To a 1 mL solution of 3% i-BuOH solution in water was added 1 mL of the hydroxylated fatty alcohol mixture, and the resulting two-phase mixture was stirred vigorously using a vortex for ten minutes. The experiment was done in duplicate, as well as on the 6% i-BuOH solution. After the mixing, the layers were separated, and the samples were taken from both layers to measure i-BuOH concentration using GC (Table 12). A partition coefficient of 3.7 was observed.

TABLE 12

Partition coefficient measurement data for i-BuOH partitioning between water and hydroxylated fatty alcohols

| Sample | i-BuOH (Amt) | Dilution Factor (20x) | Partition Coefficient | Total Conc. (mg/mL) |
|---|---|---|---|---|
| Organic layer i-BuOH, 3% | 1.13 | 22.6 | 3.53 | 29 |
| Organic layer i-BuOH, 3% | 1 | 20 | 3.45 | 25.8 |
| Water layer i-BuOH, 3% | 0.32 | 6.4 | | |
| Water layer i-BuOH, 3% | 0.29 | 5.8 | | |
| Organic layer i-BuOH, 6% | 2.15 | 43 | 3.91 | 54 |
| Organic layer i-BuOH, 6% | 1.96 | 39.2 | 3.84 | 49.4 |
| Water layer i-BuOH, 6% | 0.55 | 11 | | |
| Water layer i-BuOH, 6% | 0.51 | 10.2 | | |
| | | | 3.68 | |

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:
    a recombinant yeast capable of producing butanol from a feedstock;
    butanol; and
    at least one extractant comprising fatty acids selected from the group consisting of arachidic acid, azaleic acid, capric acid, caprylic acid, lauric acid, linoleic acid, myristic acid, oleic acid, palmitic acid, stearic acid, and mixtures thereof;
    wherein the extractant is produced from the feedstock.

2. The composition of claim 1, wherein the extractant comprises one or more fatty amides of the formula R(C=O)N(R')(R"), wherein
    R is independently selected from the group consisting of $C_3$ to $C_{27}$ alkyl groups optionally interrupted with one or more double bonds, and
    R' and R" are independently selected from the group consisting of hydrogen and $C_1$-$C_6$ alkyl groups optionally containing one or more hydroxyl groups.

3. The composition of claim 1, wherein the extractant comprises one or more fatty esters of the formula R—(C=O)—OCHR'CHR"—OH, wherein
    R is independently selected from the group consisting of $C_3$ to $C_{27}$ alkyl groups optionally interrupted with one or more double bonds, and
    R' and R" are independently selected from the group consisting of hydrogen and $C_1$-$C_4$ alkyl groups.

4. The composition of claim 1, wherein the extractant comprises one or more fatty esters of the formula R—(C=O)—OR', wherein
    R is independently selected from the group consisting of $C_3$ to $C_{27}$ alkyl groups optionally interrupted with one or more double bonds, and
    R' is an alkyl group of 8 carbons or less.

5. The composition of claim 1, wherein the extractant is a mixture of fatty amides, and wherein the mixture of fatty amides comprises linoleamide, oleamide, palmitamide, or stearamide.

6. The composition of claim 1, wherein the extractant is a mixture of fatty amides and fatty acids, and wherein the mixture of fatty amides and fatty acids comprises linoleamide, linoleic acid, oleamide, oleic acid, palmitamide, palmitic acid, stearamide, or stearic acid.

7. The composition of claim 1, wherein the fatty acids are hydroxylated fatty acids or alkoxylated fatty acids.

8. The composition of claim 1, wherein the feedstock comprises rye, wheat, corn, cane, barley, cellulosic material, lignocellulosic material, or mixtures thereof.

9. The composition of claim 1, wherein the recombinant yeast is selected from *Schizosaccharomyces, Kluyveromyces, Yarrowia, Pichia, Candida, Hansenula, Zygosaccharomyces,* and *Saccharomyces*.

10. The composition of claim 1, wherein the recombinant yeast is selected from *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii,* and *Candida glabrata*.

11. The composition of claim 1, wherein the recombinant yeast comprises a butanol biosynthetic pathway.

12. The composition of claim 1, wherein the recombinant yeast comprises an isobutanol biosynthetic pathway.

13. The composition of claim 9, wherein the recombinant yeast comprises a butanol biosynthetic pathway.

14. The composition of claim 9, wherein the recombinant yeast comprises an isobutanol biosynthetic pathway.

* * * * *

SEQUENCE LISTING

<160> NUMBER OF SEQ ID NOS: 143

<210> SEQ ID NO 1
<211> LENGTH: 11844
<212> TYPE: DNA
<213> ORGANISM: Artificial Sequence
<220> FEATURE:
<223> OTHER INFORMATION: Plasmid

<400> SEQUENCE: 1

```
tcccattacc gacatttggg cgctatacgt gcatatgttc atgtatgtat ctgtatttaa      60
aacacttttg tattattttt cctcatatat gtgtataggt ttatacggat gatttaatta     120
ttacttcacc acccttttatt tcaggctgat atcttagcct tgttactagt tagaaaaaga    180
cattttttgct gtcagtcact gtcaagagat tcttttgctg gcatttcttc tagaagcaaa    240
aagagcgatg cgtctttttcc gctgaaccgt tccagcaaaa aagactacca acgcaatatg    300
gattgtcaga atcatataaa agagaagcaa ataactcctt gtcttgtatc aattgcatta    360
taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga agtggaatt tgcagagcgt   1500
gagcagaaaa tccttttctga tttaaaacaa tatatgcatg aaggtgagca ggtgcctgca   1560
gattggaaat cagacagagc gcaccctctt gaaatcgtta agagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta attttagcaag tgacaagctt ccgaaagaat tcggggaact catgaaaacg    2160
aaagctctct agttaattaa tcatgtaatt agttatgtca cgcttacatt cacgccctcc    2220
cccacatcc gctctaaccg aaaaggaagg agttagacaa cctgaagtct aggtccctat    2280
```

-continued

```
ttattttttt atagttatgt tagtattaag aacgttattt atatttcaaa ttttttcttt     2340
ttttctgtac agacgcgtgt acgcatgtaa cattatactg aaaaccttgc ttgagaaggt     2400
tttgggacgc tcgaaggctt taatttgcgg gcggccgcac ctggtaaaac ctctagtgga     2460
gtagtagatg taatcaatga agcggaagcc aaaagaccag agtagaggcc tatagaagaa     2520
actgcgatac cttttgtgat ggctaaacaa acagacatct ttttatatgt ttttacttct     2580
gtatatcgtg aagtagtaag tgataagcga atttggctaa gaacgttgta agtgaacaag     2640
ggacctcttt tgcctttcaa aaaggattaa aatggagtta atcattgaga tttagttttc     2700
gttagattct gtatccctaa ataactccct tacccgacgg gaaggcacaa aagacttgaa     2760
taatagcaaa cggccagtag ccaagaccaa ataatactag agttaactga tggtcttaaa     2820
caggcattac gtggtgaact ccaagaccaa tatacaaaat atcgataagt tattcttgcc     2880
caccaattta aggagcctac atcaggacag tagtaccatt cctcagagaa gaggtataca     2940
taacaagaaa atcgcgtgaa caccttatat aacttagccc gttattgagc taaaaaacct     3000
tgcaaaattt cctatgaata agaatacttc agacgtgata aaaatttact ttctaactct     3060
tctcacgctg cccctatctg ttcttccgct ctaccgtgag aaataaagca tcgagtacgg     3120
cagttcgctg tcactgaact aaaacaataa ggctagttcg aatgatgaac ttgcttgctg     3180
tcaaacttct gagttccgc tgatgtgaca ctgtgacaat aaattcaaac cggttatagc     3240
ggtctcctcc ggtaccggtt ctgccacctc aatagagct cagtaggagt cagaacctct     3300
gcggtggctg tcagtgactc atccgcgttt cgtaagttgt gcgcgtgcac atttcgcccg     3360
ttcccgctca tcttgcagca ggcggaaatt ttcatcacgc tgtaggacgc aaaaaaaaaa     3420
taattaatcg tacaagaatc ttggaaaaaa aattgaaaaa ttttgtataa aagggatgac     3480
ctaacttgac tcaatggctt ttacacccag tatttccct tccttgttt gttacaatta     3540 tagaagcaag acaaaaacat atagacaacc tattcctagg agttatattt ttttacccta     3600
ccagcaatat aagtaaaaaa ctgtttaaac agtatggcag ttacaatgta ttatgaagat     3660
gatgtagaag tatcagcact tgctggaaag caaattgcag taatcggtta tggttcacaa     3720
ggacatgctc acgcacagaa tttgcgtgat tctggtcaca acgttatcat tggtgtgcgc     3780
cacggaaaat cttttgataa agcaaaagaa gatggctttg aaacatttga agtaggagaa     3840
gcagtagcta aagctgatgt tattatggtt ttggcaccag atgaacttca acaatccatt     3900
tatgaagagg acatcaaacc aaacttgaaa gcaggttcag cacttggttt tgctcacgga     3960
tttaatatcc attttggcta tattaaagta ccagaagacg ttgacgtctt tatggttgcg     4020
cctaaggctc caggtcacct tgtccgtcgg acttatactg aaggttttgg tacaccagct     4080
ttgtttgttt cacaccaaaa tgcaagtggt catgcgcgtg aaatcgcaat ggattgggcc     4140
aaaggaattg gttgtgctcg agtgggaatt attgaaacaa cttttaaaga agaaacagaa     4200
gaagatttgt ttggagaaca agctgttcta tgtggaggtt tgacagcact tgttgaagcc     4260
ggttttgaaa cactgacaga agctggatac gctggcgaat tggcttactt tgaagttttg     4320
cacgaaatga aattgattgt tgacctcatg tatgaaggtg ttttactaa aatgcgtcaa     4380 tccatctcaa atactgctga gtttggcgat tatgtgactg gtccacggat tattactgac     4440
gaagttaaaa agaatatgaa gcttgttttg gctgatattc aatctggaaa atttgctcaa     4500
gatttcgttg atgacttcaa agcggggcgt ccaaaattaa tagcctatcg cgaagctgca     4560
aaaaatcttg aaattgaaaa aattggggca gagctacgtc aagcaatgcc attcacacaa     4620
tctggtgatg acgatgcctt taaaatctat cagtaaggcc ctgcaggcct atcaagtgct     4680
```

```
ggaaactttt tctcttggaa tttttgcaac atcaagtcat agtcaattga attgacccaa    4740
tttcacattt aagattttt tttttcatc cgacatacat ctgtacacta ggaagccctg     4800
tttttctgaa gcagcttcaa atatatatat ttttttacata tttattatga ttcaatgaac   4860
aatctaatta aatcgaaaac aagaaccgaa acgcgaataa ataatttatt tagatggtga    4920
caagtgtata agtcctcatc gggacagcta cgatttctct ttcggttttg gctgagctac    4980
tggttgctgt gacgcagcgg cattagcgcg gcgttatgag ctaccctcgt ggcctgaaag    5040
atggcgggaa taaagcggaa ctaaaaatta ctgactgagc catattgagg tcaatttgtc    5100
aactcgtcaa gtcacgtttg gtggacggcc cctttccaac gaatcgtata tactaacatg    5160
cgcgcgcttc ctatatacac atatacatat atatatatat atatatgtgt gcgtgtatgt    5220
gtacacctgt atttaatttc cttactcgcg ggttttttctt ttttctcaat tcttggcttc    5280
ctctttctcg agcggaccgg atcctccgcg gtgccggcag atctatttaa atggcgcgcc    5340
gacgtcaggt ggcactttc ggggaaatgt gcgcggaacc cctatttgtt tattttttcta    5400 aatacattca aatatgtatc cgctcatgag acaataaccc tgataaatgc ttcaataata    5460
ttgaaaaagg aagagtatga gtattcaaca tttccgtgtc gcccttattc ccttttttgc    5520
ggcattttgc cttcctgttt ttgctcaccc agaaacgctg gtgaaagtaa aagatgctga    5580
agatcagttg ggtgcacgag tgggttacat cgaactggat ctcaacagcg gtaagatcct    5640
tgagagtttt cgccccgaag aacgttttcc aatgatgagc acttttaaag ttctgctatg    5700
tggcgcggta ttatcccgta ttgacgccgg gcaagagcaa ctcggtcgcc gcatacacta    5760
ttctcagaat gacttggttg agtactcacc agtcacagaa aagcatctta cggatggcat    5820
gacagtaaga gaattatgca gtgctgccat aaccatgagt gataacactg cggccaactt    5880
acttctgaca acgatcggag gaccgaagga gctaaccgct ttttgcaca acatggggga    5940 tcatgtaact cgccttgatc gttgggaacc ggagctgaat gaagccatac caaacgacga    6000
gcgtgacacc acgatgcctg tagcaatggc aacaacgttg cgcaaactat taactggcga    6060
actacttact ctagcttccc ggcaacaatt aatagactgg atggaggcgg ataaagttgc    6120
aggaccactt ctgcgctcgg cccttccggc tggctggttt attgctgata aatctggagc    6180
cggtgagcgt gggtctcgcg gtatcattgc agcactgggg ccagatggta agccctcccg    6240
tatcgtagtt atctacacga cggggagtca ggcaactatg gatgaacgaa atagacagat    6300
cgctgagata ggtgcctcac tgattaagca ttggtaactg tcagaccaag tttactcata    6360
tatactttag attgatttaa aacttcattt ttaatttaaa aggatctagg tgaagatcct    6420
ttttgataat ctcatgacca aaatccctta acgtgagttt tcgttccact gagcgtcaga    6480
ccccgtagaa aagatcaaag gatcttcttg agatcctttt tttctgcgcg taatctgctg    6540
cttgcaaaca aaaaaaccac cgctaccagc ggtggtttgt ttgccggatc aagagctacc    6600
aactcttttt ccgaaggtaa ctggcttcag cagagcgcag ataccaaata ctgttcttct    6660
agtgtagccg tagttaggcc accacttcaa gaactctgta gcaccgccta catacctcgc    6720
tctgctaatc ctgttaccag tggctgctgc cagtggcgat aagtcgtgtc ttaccgggtt    6780
ggactcaaga cgatagttac cggataaggc gcagcggtcg ggctgaacgg ggggttcgtg    6840
cacacagccc agcttggagc gaacgaccta caccgaactg agatacctac agcgtgagct    6900
atgagaaagc gccacgcttc ccgaagggag aaaggcggac aggtatccgg taagcggcag    6960
ggtcggaaca ggagagcgca cgagggagct tccaggggga aacgcctggt atctttatag    7020
```

```
tcctgtcggg tttcgccacc tctgacttga gcgtcgattt ttgtgatgct cgtcagggg    7080
gcggagccta tggaaaaacg ccagcaacgc ggccttttta cggttcctgg ccttttgctg    7140
gccttttgct cacatgttct ttcctgcgtt atccctgat tctgtggata accgtattac     7200
cgcctttgag tgagctgata ccgctcgccg cagccgaacg accgagcgca gcgagtcagt    7260
gagcgaggaa gcggaagagc gcccaatacg caaaccgcct ctccccgcgc gttggccgat    7320
tcattaatgc agctggcacg acaggtttcc cgactggaaa gcgggcagtg agcgcaacgc    7380
aattaatgtg agttagctca ctcattaggc accccaggct ttacacttta tgcttccggc    7440
tcgtatgttg tgtggaattg tgagcggata acaatttcac acaggaaaca gctatgacca    7500
tgattacgcc aagcttttc tttccaattt ttttttttc gtcattataa aaatcattac      7560
gaccgagatt cccgggtaat aactgatata attaaattga agctctaatt tgtgagttta    7620
gtatacatgc atttacttat aatacagttt tttagttttg ctggccgcat cttctcaaat    7680
atgcttccca gcctgctttt ctgtaacgtt caccctctac cttagcatcc cttcccttg     7740
caaatagtcc tcttccaaca ataataatgt cagatcctgt agagaccaca tcatccacgg    7800
ttctatactg ttgacccaat gcgtctccct tgtcatctaa acccacaccg ggtgtcataa    7860
tcaaccaatc gtaaccttca tctcttccac ccatgtctct tgagcaata aagccgataa     7920
caaaatcttt gtcgctcttc gcaatgtcaa cagtacccct agtatattct ccagtagata    7980
gggagccctt gcatgacaat tctgctaaca tcaaaaggcc tctaggttcc tttgttactt    8040
cttctgccgc ctgcttcaaa ccgctaacaa tacctgggcc caccacaccg tgtgcattcg    8100
taatgtctgc ccattctgct attctgtata cacccgcaga gtactgcaat ttgactgtat    8160
taccaatgtc agcaaatttt ctgtcttcga agagtaaaaa attgtacttg gcggataatg    8220
cctttagcgg cttaactgtg ccctccatgg aaaaatcagt caagatatcc acatgtgttt    8280
ttagtaaaca aattttggga cctaatgctt caactaactc cagtaattcc ttggtggtac    8340
gaacatccaa tgaagcacac aagtttgttt gcttttcgtg catgatatta aatagcttgg    8400
cagcaacagg actaggatga gtagcagcac gttccttata tgtagctttc gacatgattt    8460
atcttcgttt cctgcaggtt tttgttctgt gcagttgggt taagaatact gggcaatttc    8520
atgtttcttc aacactacat atgcgtatat ataccaatct aagtctgtgc tccttccttc    8580
gttcttcctt ctgttcggag attaccgaat caaaaaaatt tcaaggaaac cgaaatcaaa    8640
aaaagaata aaaaaaaat gatgaattga aaagcttgca tgcctgcagg tcgactctag      8700
tatactccgt ctactgtacg atacacttcc gctcaggtcc ttgtccttta acgaggcctt    8760
accactcttt tgttactcta ttgatccagc tcagcaaagg cagtgtgatc taagattcta    8820
tcttcgcgat gtagtaaaac tagctagacc gagaaagaga ctagaaatgc aaaaggcact    8880
tctacaatgg ctgccatcat tattatccga tgtgacgctg cattttttt ttttttttt     8940
tttttttttt tttttttttt tttttttttt ttttgtacaa atatcataaa aaagagaat    9000
cttttttaagc aaggatttc ttaacttctt cggcgacagc atcaccgact cggtggtac     9060
tgttggaacc acctaaatca ccagttctga tacctgcatc caaaaccttt ttaactgcat    9120
cttcaatggc tttaccttct tcaggcaagt tcaatgacaa tttcaacatc attgcagcag    9180
acaagatagt ggcgatagg ttgaccttat tctttggcaa atctggagcg gaaccatggc    9240
atggttcgta caaaccaaat gcggtgttct tgtctggcaa agaggccaag gacgcagatg    9300
gcaacaaacc caaggagcct gggataacg aggcttcatc ggagatgata tcaccaaaca    9360
tgttgctggt gattataata ccatttaggt gggttgggtt cttaactagg atcatggcgg    9420
```

```
cagaatcaat caattgatgt tgaactttca atgtagggaa ttcgttcttg atggtttcct    9480
ccacagtttt tctccataat cttgaagagg ccaaaacatt agctttatcc aaggaccaaa    9540
taggcaatgg tggctcatgt tgtagggcca tgaaagcggc cattcttgtg attctttgca    9600
cttctggaac ggtgtattgt tcactatccc aagcgacacc atcaccatcg tcttcctttc    9660
tcttaccaaa gtaaatacct cccactaatt ctctaacaac aacgaagtca gtacctttag    9720
caaattgtgg cttgattgga gataagtcta aagagagtc ggatgcaaag ttacatggtc    9780
ttaagttggc gtacaattga agttctttac ggattttag taaaccttgt tcaggtctaa     9840
cactaccggt accccattta ggaccaccca cagcacctaa caaaacggca tcagccttct    9900
tggaggcttc cagcgcctca tctggaagtg aacacctgt agcatcgata gcagcaccac     9960
caattaaatg attttcgaaa tcgaacttga cattggaacg aacatcagaa atagctttaa   10020
gaaccttaat ggcttcggct gtgatttctt gaccaacgtg gtcacctggc aaaacgacga   10080
tcttcttagg ggcagacatt acaatggtat atccttgaaa tatatataaa aaaaaaaaa    10140
aaaaaaaaa aaaaaatgc agcttctcaa tgatattcga atacgctttg aggagataca    10200
gcctaatatc cgacaaactg ttttacagat ttacgatcgt acttgttacc catcattgaa   10260
ttttgaacat ccgaacctgg gagttttccc tgaaacagat agtatatttg aacctgtata   10320
ataatatata gtctagcgct ttacggaaga caatgtatgt atttcggttc ctggagaaac   10380
tattgcatct attgcatagg taatcttgca cgtcgcatcc ccggttcatt ttctgcgttt   10440
ccatcttgca cttcaatagc atatctttgt taacgaagca tctgtgcttc attttgtaga   10500
acaaaaatgc aacgcgagag cgctaatttt tcaaacaaag aatctgagct gcattttac    10560
agaacagaaa tgcaacgcga aagcgctatt ttaccaacga agaatctgtg cttcattttt   10620
gtaaaacaaa aatgcaacgc gagagcgcta attttcaaa caaagaatct gagctgcatt    10680
tttacagaac agaaatgcaa cgcgagagcg ctattttacc aacaaagaat ctatacttct   10740
ttttgttct acaaaaatgc atcccgagag cgctattttt ctaacaaagc atcttagatt    10800
acttttttc tcctttgtgc gctctataat gcagtctctt gataacttt tgcactgtag     10860
gtccgttaag gttagaagaa ggctactttg gtgtctattt tctcttccat aaaaaaagcc   10920
tgactccact tcccgcgttt actgattact agcgaagctg cgggtgcatt ttttcaagat   10980
aaaggcatcc ccgattatat tctataccga tgtggattgc gcatactttg tgaacagaaa   11040
gtgatagcgt tgatgattct tcattggtca gaaaattatg aacggtttct tctattttgt   11100
ctctatatac tacgtatagg aaatgtttac attttcgtat tgttttcgat tcactctatg   11160
aatagttctt actacaattt ttttgtctaa agagtaatac tagagataaa cataaaaaat   11220
gtagaggtcg agtttagatg caagttcaag gagcgaaagg tggatgggta ggttatatag   11280
ggatatagca cagagatata tagcaaagag atactttga gcaatgtttg tggaagcggt    11340
attcgcaata ttttagtagc tcgttacagt ccggtgcgtt tttggttttt tgaaagtgcg   11400
tcttcagagc gcttttggtt ttcaaaagcg ctctgaagtt cctatacttt ctagagaata   11460
ggaacttcgg aataggaact tcaaagcgtt tccgaaaacg agcgcttccg aaaatgcaac   11520
gcgagctgcg cacatacagc tcactgttca cgtcgcacct atatctgcgt gttgcctgta   11580
tatatatata catgagaaga acggcatagt gcgtgtttat gcttaaatgc gtacttatat   11640
gcgtctattt atgtaggatg aaaggtagtc tagtacctcc tgtgatatta tcccattcca   11700
tgcggggtat cgtatgcttc cttcagcact acccttagc tgttctatat gctgccactc    11760
```

-continued

| | |
|---|---|
| ctcaattgga ttagtctcat ccttcaatgc tatcatttcc tttgatattg gatcatatgc | 11820 |
| atagtaccga gaaactagag gatc | 11844 |

<210> SEQ ID NO 2
<211> LENGTH: 15539
<212> TYPE: DNA
<213> ORGANISM: Artificial Sequence
<220> FEATURE:
<223> OTHER INFORMATION: Plasmid

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| tttttttttt ccacctagcg gatgactctt tttttttctt agcgattggc attatcacat | 420 |
| aatgaattat acattatata agtaatgtg atttcttcga agaatatact aaaaaatgag | 480 |
| caggcaagat aaacgaaggc aaagatgaca gagcagaaag ccctagtaaa gcgtattaca | 540 |
| aatgaaacca agattcagat tgcgatctct ttaaagggtg tccccctagc gatagagcac | 600 |
| tcgatcttcc cagaaaaaga ggcagaagca gtagcagaac aggccacaca atcgcaagtg | 660 |
| attaacgtcc acacaggtat agggtttctg gaccatatga tacatgctct ggccaagcat | 720 |
| tccggctggt cgctaatcgt tgagtgcatt ggtgacttac acatagacga ccatcacacc | 780 |
| actgaagact gcgggattgc tctcggtcaa gcttttaaag gggcctagg ggccgtgcgt | 840 |
| ggagtaaaaa ggtttggatc aggatttgcg cctttggatg aggcactttc cagagcggtg | 900 |
| gtagatcttt cgaacaggcc gtacgcagtt gtcgaacttg gtttgcaaag ggagaaagta | 960 |
| ggagatctct cttgcgagat gatcccgcat tttcttgaaa gctttgcaga ggctagcaga | 1020 |
| attaccctcc acgttgattg tctgcgaggc aagaatgatc atcaccgtag tgagagtgcg | 1080 |
| ttcaaggctc ttgcggttgc cataagagaa gccacctcgc ccaatggtac caacgatgtt | 1140 |
| ccctccacca aaggtgttct tatgtagtga caccgattat ttaaagctgc agcatacgat | 1200 |
| atatatacat gtgtatatat gtataccat gaatgtcagt aagtatgtat acgaacagta | 1260 |
| tgatactgaa gatgacaagg taatgcatca ttctatacgt gtcattctga acgaggcgcg | 1320 |
| ctttcctttt ttcttttttgc ttttttcttt tttttctctt gaactcgacg gatctatgcg | 1380 |
| gtgtgaaata ccgcacagat gcgtaaggag aaaataccgc atcaggaaat tgtaagcgtt | 1440 |
| aatattttgt taaaattcgc gttaaatttt tgttaaatca gctcattttt taaccaatag | 1500 |
| gccgaaatcg gcaaaatccc ttataaatca aagaataga ccgagatagg gttgagtgtt | 1560 |
| gttccagttt ggaacaagag tccactatta agaacgtgg actccaacgt caagggcga | 1620 |
| aaaccgtct atcagggcga tggcccacta cgtgaaccat caccctaatc aagttttttg | 1680 |
| gggtcgaggt gccgtaaagc actaaatcgg aaccctaaag ggagccccg atttagagct | 1740 |
| tgacggggaa agccggcgaa cgtggcgaga aggaaggga agaaagcgaa aggagcgggc | 1800 |
| gctagggcgc tggcaagtgt agcggtcacg ctgcgcgtaa ccaccacacc cgccgcgctt | 1860 |
| aatgcgccgc tacagggcgc gtccattcgc cattcaggct gcgcaactgt tgggaagggc | 1920 |
| gcggtgcggg cctcttcgct attacgccag ctggcgaaag gggatgtgc tgcaaggcga | 1980 |

-continued

```
ttaagttggg taacgccagg gttttcccag tcacgacgtt gtaaaacgac ggccagtgag    2040
cgcgcgtaat acgactcact atagggcgaa ttgggtaccg ggccccccct cgaggtcgac    2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tcctttcccc    2400
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttcctttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaaagta ttggatggtt    2820
aataccattt gtctgttctc ttctgacttt gactcctcaa aaaaaaaat ctacaatcaa     2880 cagatcgctt caattacgcc ctcacaaaaa ctttttttcct tcttcttcgc ccacgttaaa    2940
ttttatccct catgttgtct aacggatttc tgcacttgat ttattataaa aagacaaaga    3000
cataatactt ctctatcaat ttcagttatt gttcttcctt gcgttattct tctgttcttc    3060
tttttctttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300
tggtaaacta gccaaagtcg gtgttaagga agctggtgct tggccagttc agttcggaac    3360
aatcacggtt tctgatggaa tcgccatggg aaccccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccatttttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct caccggctg aatccgcaga aagaaagca gatattgaag aagctggtcg     3840
cgctgttgtc aaaatgctcg aaatgggctt aaaaccttct gacattttaa cgcgtgaagc    3900
ttttgaagat gctattactg taactatggc tctgggaggg tcaaccaact caacccttca    3960
cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctcctaaaaa atggcttcct    4140
tcatggtgac cgtatcactt gtactggcaa aacagtcgct gaaaatttga aggcttttga    4200
tgatttaaca cctggtcaaa aggttattat gccgcttgaa aatcctaaac gtgaagatgg    4260
tccgctcatt attctccatg gtaacttggc tccagacggt gccgttgcca aagtttctgg    4320
```

```
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaatgttgt tcctggttgc tgtggttaag cggccgcgtt   4860
aattcaaatt aattgatata gtttttaat gagtattgaa tctgtttaga ataatggaa   4920 tattattttt atttatttat ttatattatt ggtcggctct tttcttctga aggtcaatga   4980
caaaatgata tgaaggaaat aatgattct aaaattttac aacgtaagat attttacaa   5040 aagcctagct catcttttgt catgcactat tttactcacg cttgaaatta acggccagtc   5100
cactgcggag tcatttcaaa gtcatcctaa tcgatctatc gttttgata gctcattttg   5160 gagttcgcga ttgtcttctg ttattcacaa ctgttttaat ttttatttca ttctggaact   5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aacttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc cttttccct actccttta   5580 gtacggaaga caatgctaat aaataagagg gtaataataa tattattaat cggcaaaaaa   5640
gattaaacgc caagcgttta ttatcagaa agcaaacgtc gtaccaatcc ttgaatgctt   5700
cccaattgta tattaagagt catcacagca acatattctt gttattaaat taattattat   5760 tgattttga tattgtataa aaaaaccaaa tatgtataaa aaaagtgaat aaaaaatacc   5820
aagtatggag aaatatatta gaagtctata cgttaaacca cccgggcccc cctcgaggt   5880 cgacggtatc gataagcttg atatcgaatt cctgcagccc ggggatcca ctagttctag   5940 agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat ttttttata acttatttaa   6240 taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
```

```
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg aaaatccgc accctatcaa     6900 gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt tccatcagc     7740 tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagccacca   7920 tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagattttta    8640
catttctggt gttgaaggga agatatgag ctatacagcg gaatttccat atcactcaga    8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt tttttcatgt agatgatact gactgcacgc aaatataggc atgatttata    8880
ggcatgattt gatggctgta ccgataggaa cgctaagagt aacttcagaa tcgttatcct    8940
ggcggaaaaa attcatttgt aaactttaaa aaaaaagcc aatatcccca aaattattaa     9000
gagcgcctcc attattaact aaaatttcac tcagcatcca caatgtatca ggtatctact    9060
```

```
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc    9240
tgcaggcctc agctcttgtt ttgttctgca ataacttac ccatctttt caaaacttta    9300 ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcctg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg ttttcagcc   10380 ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca ataccaccg tctttatata   11040 cttattagtc aagtagggga ataatttcag ggaactggtt tcaaccttt tttcagctt   11100 tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt tttttgcctg tttgtgcccc tgttctctgt agttgcgcta agagaatgga   11280
cctatgaact gatggttggt gaagaaaaca atatttggt gctgggattc tttttttttc   11340
tggatgccag cttaaaaagc gggctccatt atatttagtg gatgccagga ataaactgtt   11400
cacccagaca cctacgatgt tatatattct gtgtaacccg cccctatttt gggcatgta   11460
```

```
cgggttacag cagaattaaa aggctaattt tttgactaaa taaagttagg aaaatcacta    11520
ctattaatta tttacgtatt ctttgaaatg gcagtattga taatgataaa ctcgaactga    11580
aaaagcgtgt tttttattca aaatgattct aactccctta cgtaatcaag gaatcttttt    11640
gccttggcct ccgcgtcatt aaacttcttg ttgttgacgc taacattcaa cgctagtata    11700
tattcgtttt tttcaggtaa gttcttttca acgggtctta ctgatgaggc agtcgcgtct    11760
gaacctgtta agaggtcaaa tatgtcttct tgaccgtacg tgtcttgcat gttattagct    11820
ttgggaattt gcatcaagtc ataggaaaat ttaaatcttg gctctcttgg gctcaaggtg    11880
acaaggtcct cgaaaatagg gcgcgcccca ccgcggtgga gctccagctt ttgttccctt    11940
tagtgagggt taattgcgcg cttggcgtaa tcatggtcat agctgtttcc tgtgtgaaat    12000
tgttatccgc tcacaattcc acacaacata cgagccggaa gcataaagtg taaagcctgg    12060
ggtgcctaat gagtgagcta actcacatta attgcgttgc gctcactgcc cgctttccag    12120
tcgggaaacc tgtcgtgcca gctgcattaa tgaatcggcc aacgcgcggg gagaggcggt    12180
ttgcgtattg ggcgctcttc cgcttcctcg ctcactgact cgctgcgctc ggtcgttcgg    12240
ctgcggcgag cggtatcagc tcactcaaag gcggtaatac ggttatccac agaatcaggg    12300
gataacgcag gaaagaacat gtgagcaaaa ggccagcaaa aggccaggaa ccgtaaaaag    12360
gccgcgttgc tggcgttttt ccataggctc cgcccccctg acgagcatca caaaaatcga    12420
cgctcaagtc agaggtggcg aaacccgaca ggactataaa gataccaggc gtttccccct    12480
ggaagctccc tcgtgcgctc tcctgttccg accctgccgc ttaccggata cctgtccgcc    12540
tttctccctt cgggaagcgt ggcgctttct catagctcac gctgtaggta tctcagttcg    12600
gtgtaggtcg ttcgctccaa gctgggctgt gtgcacgaac ccccgttca gcccgaccgc    12660 tgcgccttat ccggtaacta tcgtcttgag tccaacccgg taagacacga cttatcgcca    12720
ctggcagcag ccactggtaa caggattagc agagcgaggt atgtaggcgg tgctacagag    12780
ttcttgaagt ggtggcctaa ctacggctac actagaagaa cagtatttgg tatctgcgct    12840
ctgctgaagc cagttacctt cggaaaaaga gttggtagct cttgatccgg caaacaaacc    12900
accgctggta gcggtggttt ttttgtttgc aagcagcaga ttacgcgcag aaaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
taaaaatgaa gttttaaatc aatctaaagt atatatgagt aaacttggtc tgacagttac    13140
caatgcttaa tcagtgaggc acctatctca gcgatctgtc tatttcgttc atccatagtt    13200
gcctgactcc ccgtcgtgta gataactacg atacgggagg gcttaccatc tggccccagt    13260
gctgcaatga taccgcgaga cccacgctca ccggctccag atttatcagc aataaaccag    13320
ccagccggaa gggccgagcg cagaagtggt cctgcaactt tatccgcctc catccagtct    13380
attaattgtt gccgggaagc tagagtaagt agttcgccag ttaatagttt gcgcaacgtt    13440
gttgccattg ctacaggcat cgtggtgtca cgctcgtcgt ttggtatggc ttcattcagc    13500
tccggttccc aacgatcaag gcgagttaca tgatccccca tgttgtgcaa aaaagcggtt    13560
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga gaatagtgta tgcggcgacc gagttgctct    13740
tgcccggcgt caatacggga taataccgcg ccacatagca gaactttaaa agtgctcatc    13800
```

```
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttccttttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taattttca aacaaagaat ctgagctgca tttttacaga    14220
acagaaatgc aacgcgaaag cgctatttta ccaacgaaga atctgtgctt cattttttgta    14280 aaacaaaaat gcaacgcgag agcgctaatt tttcaaacaa agaatctgag ctgcattttt    14340
acagaacaga aatgcaacgc gagagcgcta ttttaccaac aaagaatcta tacttctttt    14400
ttgttctaca aaaatgcatc ccgagagcgc tattttcta acaaagcatc ttagattact    14460
ttttttctcc tttgtgcgct ctataatgca gtctcttgat aacttttgc actgtaggtc    14520 cgttaaggtt agaagaaggc tactttggtg tctatttct cttccataaa aaagcctga    14580 ctccacttcc cgcgtttact gattactagc gaagctgcgg gtgcattttt tcaagataaa    14640 ggcatcccccg attatattct ataccgatgt ggattgcgca tactttgtga acagaaagtg    14700
atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaattttt tgtctaaaga gtaatactag ataaacat aaaaaatgta    14880 gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggtttttga agtgcgtct    15060 tcagagcgct tttggttttc aaaagcgctc tgaagttcct atactttcta gagaatagga    15120
acttcggaat aggaacttca aagcgtttcc gaaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539
```

<210> SEQ ID NO 3
<211> LENGTH: 4586
<212> TYPE: DNA
<213> ORGANISM: Artificial Sequence
<220> FEATURE:
<223> OTHER INFORMATION: pLA54 plasmid

<400> SEQUENCE: 3

```
gggtaccgag ctcgaattca ctggccgtcg ttttacaacg tcgtgactgg gaaaaccctg      60
gcgttaccca acttaatcgc cttgcagcac atccccctttt cgccagctgg cgtaatagcg     120
aagaggcccg caccgatcgc ccttcccaac agttgcgcag cctgaatggc gaatggcgcc     180
tgatgcggta ttttctcctt acgcatctgt gcggtatttc acaccgcata tggtgcactc     240
tcagtacaat ctgctctgat gccgcatagt taagccagcc ccgacacccg ccaacacccg     300
ctgacgcgcc ctgacgggct tgtctgctcc cggcatccgc ttacagacaa gctgtgaccg     360
```

```
tctccgggag ctgcatgtgt cagaggtttt caccgtcatc accgaaacgc gcgagacgaa    420
agggcctcgt gatacgccta tttttatagg ttaatgtcat gataataatg gtttcttaga    480
cgtcaggtgg cacttttcgg ggaaatgtgc gcggaacccc tatttgttta tttttctaaa    540
tacattcaaa tatgtatccg ctcatgagac aataaccctg ataaatgctt caataatatt    600
gaaaaaggaa gagtatgagt attcaacatt tccgtgtcgc ccttattccc ttttttgcgg    660
cattttgcct tcctgttttt gctcacccag aaacgctggt gaaagtaaaa gatgctgaag    720
atcagttggg tgcacgagtg ggttacatcg aactggatct caacagcggt aagatccttg    780
agagttttcg ccccgaagaa cgttttccaa tgatgagcac ttttaaagtt ctgctatgtg    840
gcgcggtatt atcccgtatt gacgccgggc aagagcaact cggtcgccgc atacactatt    900
ctcagaatga cttggttgag tactcaccag tcacagaaaa gcatcttacg gatggcatga    960
cagtaagaga attatgcagt gctgccataa ccatgagtga taacactgcg ccaacttac    1020 ttctgacaac gatcggagga ccgaaggagc taaccgcttt tttgcacaac atggggatc    1080 atgtaactcg ccttgatcgt tgggaaccgg agctgaatga agccatacca aacgacgagc    1140
gtgacaccac gatgcctgta gcaatggcaa caacgttgcg caaactatta actggcgaac    1200
tacttactct agcttcccgg caacaattaa tagactggat ggaggcggat aaagttgcag    1260
gaccacttct gcgctcggcc cttccggctg gctggtttat tgctgataaa tctggagccg    1320
gtgagcgtgg gtctcgcggt atcattgcag cactggggcc agatggtaag ccctcccgta    1380
tcgtagttat ctacacgacg gggagtcagg caactatgga tgaacgaaat agacagatcg    1440
ctgagatagg tgcctcactg attaagcatt ggtaactgtc agaccaagtt tactcatata    1500
tactttagat tgatttaaaa cttcattttt aatttaaaag gatctaggtg aagatccttt    1560
ttgataatct catgaccaaa atcccttaac gtgagttttc gttccactga gcgtcagacc    1620
ccgtagaaaa gatcaaagga tcttcttgag atcctttttt tctgcgcgta atctgctgct    1680
tgcaaacaaa aaaaccaccg ctaccagcgg tggtttgttt gccggatcaa gagctaccaa    1740
ctctttttcc gaaggtaact ggcttcagca gagcgcagat accaaatact gtccttctag    1800
tgtagccgta gttaggccac cacttcaaga actctgtagc accgcctaca tacctcgctc    1860
tgctaatcct gttaccagtg gctgctgcca gtggcgataa gtcgtgtctt accgggttgg    1920
actcaagacg atagttaccg gataaggcgc agcggtcggg ctgaacgggg gttcgtgca    1980 cacagcccag cttggagcga acgacctaca ccgaactgag atacctacag cgtgagctat    2040
gagaaagcgc cacgcttccc gaagggagaa aggcggacag gtatccggta agcggcaggg    2100
tcggaacagg agagcgcacg agggagcttc caggggggaaa cgcctggtat ctttatagtc    2160
ctgtcgggtt tcgccacctc tgacttgagc gtcgattttt gtgatgctcg tcagggggc    2220 ggagcctatg gaaaaacgcc agcaacgcgg cctttttacg gttcctggcc ttttgctggc    2280
cttttgctca catgttcttt cctgcgttat cccctgattc tgtggataac cgtattaccg    2340
cctttgagtg agctgatacc gctcgccgca gccgaacgac cgagcgcagc gagtcagtga    2400
gcgaggaagc ggaagagcgc ccaatacgca aaccgcctct ccccgcgcgt tggccgattc    2460
attaatgcag ctggcacgac aggtttcccg actggaaagc gggcagtgag cgcaacgcaa    2520
ttaatgtgag ttagctcact cattaggcac cccaggcttt acactttatg cttccggctc    2580
gtatgttgtg tggaattgtg agcggataac aatttcacac aggaaacagc tatgaccatg    2640
attacgccaa gcttgcatgc ctgcaggtcg actctagagg atccccgcat tgcggattac    2700
```

```
gtattctaat gttcagataa cttcgtatag catacattat acgaagttat ctagggattc    2760
ataaccattt tctcaatcga attacacaga acacaccgta caaacctctc tatcataact    2820
acttaatagt cacacacgta ctcgtctaaa tacacatcat cgtcctacaa gttcatcaaa    2880
gtgttggaca gacaactata ccagcatgga tctcttgtat cggttctttt ctcccgctct    2940
ctcgcaataa caatgaacac tgggtcaatc atagcctaca caggtgaaca gagtagcgtt    3000
tatacagggt ttatacggtg attcctacgg caaaaatttt tcatttctaa aaaaaaaaag    3060 aaaaatttt ctttccaacg ctagaaggaa agaaaaatc taattaaatt gatttggtga     3120
ttttctgaga gttccctttt tcatatatcg aattttgaat ataaaaggag atcgaaaaaa    3180 ttttctatt caatctgttt ctggttttta tttgatagtt tttttgtgta ttattattat     3240
ggattagtac tggtttatat gggtttttct gtataacttc tttttatttt agtttgttta    3300
atcttatttt gagttacatt atagttccct aactgcaaga gaagtaacat aaaactcga    3360 gatgggtaag gaaaagactc acgtttcgag gccgcgatta aattccaaca tggatgctga   3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag cattttatcc gtactcctga tgatgcatgg ttactcacca ctgcgatccc    3660
cggcaaaaca gcattccagg tattagaaga atatcctgat tcaggtgaaa atattgttga    3720
tgcgctggca gtgttcctgc gccggttgca ttcgattcct gtttgtaatt gtccttttaa    3780
cagcgatcgc gtatttcgtc tcgctcaggc gcaatcacga atgaataacg gtttggttga    3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
cgcagaccga taccaggatc ttgccatcct atggaactgc ctcggtgagt tttctccttc    4080
attacagaaa cggctttttc aaaaatatgg tattgataat cctgatatga ataaattgca    4140
gtttcatttg atgctcgatg agttttttcta agtttaactt gatactacta gatttttct    4200 cttcatttat aaaattttg gttataattg aagctttaga agtatgaaaa aatccttttt    4260
tttcattctt tgcaaccaaa ataagaagct tcttttattc attgaaatga tgaatataaa    4320
cctaacaaaa gaaaaagact cgaatatcaa acattaaaaa aaaataaaag aggttatctg    4380
ttttcccatt tagttggagt ttgcatttc taatagatag aactctcaat taatgtggat    4440
ttagtttctc tgttcgtttt ttttttgtttt gttctcactg tatttacatt tctatttagt    4500
atttagttat tcatataatc tataacttcg tatagcatac attatacgaa gttatccagt    4560
gatgatacaa cgagttagcc aaggtg                                         4586
```

<210> SEQ ID NO 4
<211> LENGTH: 80
<212> TYPE: DNA
<213> ORGANISM: Artificial Sequence
<220> FEATURE:
<223> OTHER INFORMATION: Primer

<400> SEQUENCE: 4

```
ttccggtttc tttgaaattt ttttgattcg gtaatctccg agcagaagga gcattgcgga      60
ttacgtattc taatgttcag                                                  80
```

```
<210> SEQ ID NO 5
<211> LENGTH: 81
<212> TYPE: DNA
<213> ORGANISM: Artificial Sequence
<220> FEATURE:
<223> OTHER INFORMATION: Primer

<400> SEQUENCE: 5
gggtaataac tgatataatt aaattgaagc tctaatttgt gagtttagta caccttggct     60
aactcgttgt atcatcactg g                                              81

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gcctcgagtt ttaatgttac ttctcttgca gttaggga                             38

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gctaaattcg agtgaaacac aggaagacca g                                    31

<210> SEQ ID NO 8
<211> LENGTH: 90
<212> TYPE: DNA
<213> ORGANISM: Artificial Sequence
<220> FEATURE:
<223> OTHER INFORMATION: Primer

<400> SEQUENCE: 8
gtattttggt agattcaatt ctctttccct ttccttttcc ttcgctcccc ttccttatca     60
gcattgcgga ttacgtattc taatgttcag                                      90

<210> SEQ ID NO 9
<211> LENGTH: 90
<212> TYPE: DNA
<213> ORGANISM: Artificial Sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc     60
accttggcta actcgttgta tcatcactgg                                      90

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggtgcggg cctcttcgct a                                               21

<210> SEQ ID NO 11
```

<211> LENGTH: 21
<212> TYPE: DNA
<213> ORGANISM: Artificial Sequence
<220> FEATURE:
<223> OTHER INFORMATION: Primer

<400> SEQUENCE: 11
aatgtgagtt agctcactca t					21

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
aattggatcc ggcgcgccgt ttaaacggcc ggccaatgtg ctgtggtttt cagggtc					57

<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatttctaga ttaattaagc ggccgcaagg ccatgaagct ttttctttc					49

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ttctcgacgt gggccttttt cttg					24

<210> SEQ ID NO 15
<211> LENGTH: 49
<212> TYPE: DNA
<213> ORGANISM: Artificial Sequence
<220> FEATURE:
<223> OTHER INFORMATION: Primer

<400> SEQUENCE: 15
tgcagcttta ataatcggt gtcactactt tgccttcgtt tatcttgcc					49

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
gagcaggcaa gataaacgaa ggcaaagtag tgacaccgat tatttaaag					49

<210> SEQ ID NO 17
<211> LENGTH: 49
<212> TYPE: DNA
<213> ORGANISM: Artificial Sequence
<220> FEATURE:
<223> OTHER INFORMATION: Primer

<400> SEQUENCE: 17

```
tatggaccct gaaaccacag ccacattgta accaccacga cggttgttg          49
```

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18

```
tttagcaaca accgtcgtgg tggttacaat gtggctgtgg tttcagggt           49
```

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19

```
ccagaaaccc tatacctgtg tggacgtaag gccatgaagc ttttctttt           49
```

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20

```
attggaaaga aaagcttca tggccttacg tccacacagg tatagggtt            49
```

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21

```
cataagaaca cctttggtgg ag                                        22
```

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22

```
aggattatca ttcataagtt tc                                        22
```

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23

```
ttcttggagc tgggacatgt ttg                                       23
```

<210> SEQ ID NO 24
<211> LENGTH: 22
<212> TYPE: DNA

<213> ORGANISM: Artificial Sequence
<220> FEATURE:
<223> OTHER INFORMATION: Primer

<400> SEQUENCE: 24
tgatgatatt tcataaataa tg                                    22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
atgcgtccat ctttacagtc ctg                                   23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tacgtacgga ccaatcgaag tg                                    22

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27
aattcgtttg agtacactac taatggcttt gttggcaata tgttttgc         49

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
atatagcaaa aacatattgc caacaaagcc attagtagtg tactcaaac        49

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
tatggaccct gaaccacag ccacattctt gttatttata aaaagacac         49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
ctcccgtgtc ttttataaa taacaagaat gtggctgtgg tttcagggt          49

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
taccgtaggc gtccttagga aagatagaag gccatgaagc ttttcttt                49

<210> SEQ ID NO 32
<211> LENGTH: 49
<212> TYPE: DNA
<213> ORGANISM: Artificial Sequence
<220> FEATURE:
<223> OTHER INFORMATION: Primer

<400> SEQUENCE: 32
attggaaaga aaagcttca tggccttcta tctttcctaa ggacgccta                49

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ttattgtttg gcatttgtag c                                             21

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ccaagcatct cataaaccta tg                                            22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tgtgcagatg cagatgtgag ac                                            22

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36
agttattgat accgtac                                                  17

<210> SEQ ID NO 37
<211> LENGTH: 19
<212> TYPE: DNA
<213> ORGANISM: Artificial Sequence
<220> FEATURE:

<223> OTHER INFORMATION: Primer

<400> SEQUENCE: 37
cgagataccg taggcgtcc                                              19

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttatgtatgc tcttctgact tttc                                        24

<210> SEQ ID NO 39
<211> LENGTH: 49
<212> TYPE: DNA
<213> ORGANISM: Artificial Sequence
<220> FEATURE:
<223> OTHER INFORMATION: Primer

<400> SEQUENCE: 39
aataattaga gattaaatcg ctcatttttt gccagtttct tcaggcttc              49

<210> SEQ ID NO 40
<211> LENGTH: 49
<212> TYPE: DNA
<213> ORGANISM: Artificial Sequence
<220> FEATURE:
<223> OTHER INFORMATION: Primer

<400> SEQUENCE: 40
agcctgaaga aactggcaaa aaatgagcga tttaatctct aattattag              49

<210> SEQ ID NO 41
<211> LENGTH: 49
<212> TYPE: DNA
<213> ORGANISM: Artificial Sequence
<220> FEATURE:
<223> OTHER INFORMATION: Primer

<400> SEQUENCE: 41
tatggaccct gaaccacag ccacattttt caatcattgg agcaatcat               49

<210> SEQ ID NO 42
<211> LENGTH: 49
<212> TYPE: DNA
<213> ORGANISM: Artificial Sequence
<220> FEATURE:
<223> OTHER INFORMATION: Primer

<400> SEQUENCE: 42
taaaatgatt gctccaatga ttgaaaaatg tggctgtggt ttcagggtc              49

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
accgtaggtg ttgtttggga aagtggaagg ccatgaagct ttttctttc              49

<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
ttggaaagaa aaagcttcat ggccttccac tttcccaaac aacacctac         49

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttattgctta gcgttggtag cag         23

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tttttggtgg ttccggcttc c         21

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
aaagttggca tagcggaaac tt         22

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gtcattgaca ccatct         16

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
agagataccg taggtgttg         19

<210> SEQ ID NO 50
<211> LENGTH: 33
<212> TYPE: DNA
<213> ORGANISM: Artificial Sequence
<220> FEATURE:
<223> OTHER INFORMATION: Primer -continued

<400> SEQUENCE: 50
aattggcgcg ccatgaaagc tctggtttat cac                                33

<210> SEQ ID NO 51
<211> LENGTH: 49
<212> TYPE: DNA
<213> ORGANISM: Artificial Sequence
<220> FEATURE:
<223> OTHER INFORMATION: Primer

<400> SEQUENCE: 51
tgaatcatga gttttatgtt aattagctca ggcagcgcct gcgttcgag               49

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
atcctctcga acgcaggcgc tgcctgagct aattaacata aaactcatg               49

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
aattgtttaa acaagtaaat aaattaatca gcat                               34

<210> SEQ ID NO 54
<211> LENGTH: 49
<212> TYPE: DNA
<213> ORGANISM: Artificial Sequence
<220> FEATURE:
<223> OTHER INFORMATION: Primer

<400> SEQUENCE: 54
acacaataca ataacaagaa gaacaaaatg aaagctctgg tttatcacg               49

<210> SEQ ID NO 55
<211> LENGTH: 49
<212> TYPE: DNA
<213> ORGANISM: Artificial Sequence
<220> FEATURE:
<223> OTHER INFORMATION: Primer

<400> SEQUENCE: 55
agcgtataca tctgttggga aagtagaagg ccatgaagct ttttctttc               49

<210> SEQ ID NO 56
<211> LENGTH: 49
<212> TYPE: DNA
<213> ORGANISM: Artificial Sequence
<220> FEATURE:
<223> OTHER INFORMATION: Primer

<400> SEQUENCE: 56
ttggaaagaa aaagcttcat ggccttctac tttcccaaca gatgtatac               49

<210> SEQ ID NO 57
<211> LENGTH: 22

```
<212> TYPE: DNA
<213> ORGANISM: Artificial Sequence
<220> FEATURE:
<223> OTHER INFORMATION: Primer

<400> SEQUENCE: 57
ttattgttta gcgttagtag cg                                              22

<210> SEQ ID NO 58
<211> LENGTH: 72
<212> TYPE: DNA
<213> ORGANISM: Artificial Sequence
<220> FEATURE:
<223> OTHER INFORMATION: Primer

<400> SEQUENCE: 58
cataatcaat ctcaaagaga acaacacaat acaataacaa gaagaacaaa atgaaagctc     60
tggtttatca cg                                                         72

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
taggcataat caccgaagaa g                                               21

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
aaaatggtaa gcagctgaaa g                                               21

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
agttgttaga actgttg                                                    17

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gacgatagcg tatacatct                                                  19

<210> SEQ ID NO 63
<211> LENGTH: 22
<212> TYPE: DNA
<213> ORGANISM: Artificial Sequence
<220> FEATURE:
<223> OTHER INFORMATION: Primer
```

<400> SEQUENCE: 63
cttagcctct agccatagcc at        22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ttagttttgc tggccgcatc ttc        23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cccattaata tactattgag a        21

<210> SEQ ID NO 66
<211> LENGTH: 7523
<212> TYPE: DNA
<213> ORGANISM: Artificial Sequence
<220> FEATURE:
<223> OTHER INFORMATION: Plasmid

<400> SEQUENCE: 66
ccagcttttg ttcccttag tgagggttaa ttgcgcgctt ggcgtaatca tggtcatagc        60
tgtttcctgt gtgaaattgt tatccgctca caattccaca acataggga gccggaagca       120
taaagtgtaa agcctggggt gcctaatgag tgaggtaact cacattaatt gcgttgcgct      180
cactgcccgc tttccagtcg ggaaacctgt cgtgccagct gcattaatga atcggccaac      240
gcgcggggag aggcggtttg cgtattgggc gctcttccgc ttcctcgctc actgactcgc      300
tgcgctcggt cgttcggctg cggcgagcgg tatcagctca ctcaaaggcg gtaatacggt      360
tatccacaga atcaggggat aacgcaggaa agaacatgtg agcaaaaggc cagcaaaagg      420
ccaggaaccg taaaaaggcc gcgttgctgg cgtttttcca taggctccgc cccctgacg      480
agcatcacaa aaatcgacgc tcaagtcaga ggtggcgaaa cccgacagga ctataaagat      540
accaggcgtt tccccctgga agctccctcg tgcgctctcc tgttccgacc ctgccgctta      600
ccggatacct gtccgccttt ctcccttcgg gaagcgtggc gctttctcat agctcacgct      660
gtaggtatct cagttcggtg taggtcgttc gctccaagct gggctgtgtg cacgaacccc      720
ccgttcagcc cgaccgctgc gccttatccg gtaactatcg tcttgagtcc aacccggtaa      780
gacacgactt atcgccactg gcagcagcca ctggtaacag gattagcaga gcgaggtatg      840
taggcggtgc tacagagttc ttgaagtggt ggcctaacta cggctacact agaaggacag      900
tatttggtat ctgcgctctg ctgaagccag ttaccttcgg aaaaagagtt ggtagctctt      960
gatccggcaa acaaaccacc gctggtagcg gtggtttttt tgtttgcaag cagcagatta     1020
cgcgcagaaa aaaaggatct caagaagatc ctttgatctt ttctacgggg tctgacgctc     1080
agtggaacga aaactcacgt taagggattt tggtcatgag attatcaaaa aggatcttca     1140
cctagatcct tttaaattaa aaatgaagtt ttaaatcaat ctaaagtata tatgagtaaa     1200
cttggtctga cagttaccaa tgcttaatca gtgaggcacc tatctcagcg atctgtctat     1260

```
ttcgttcatc catagttgcc tgactccccg tcgtgtagat aactacgata cgggagggct    1320
taccatctgg ccccagtgct gcaatgatac cgcgagaccc acgctcaccg gctccagatt    1380
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttaataac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg catttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta ataatgcagtc tcttgataac    2580 tttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca atttttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatattttag tagctcgtta cagtccggtg cgttttggt    3120 tttttgaaag tgcgtcttca gagcgctttt ggttttcaaa agcgctctga agttcctata    3180
ctttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactacccct tagctgttct    3480
atatgctgcc actcctcaat tggattagtc tcatccttca atgctatcat ttcctttgat    3540
attggatcat ctaagaaacc attattatca tgacattaac ctataaaaat aggcgtatca    3600
```

```
cgaggcccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcattttt ttttccccct agcggatgac tcttttttt tcttagcgat   4020 tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttcttttg cttttctttt tttttctct tgaactcgac     4980 ggatctatgc ggtgtgaaat accgcacaga tgcgtaagga gaaataccg catcaggaaa   5040 ttgtaaacgt taatattttg ttaaaattcg cgttaaattt tgttaaatc agctcatttt   5100 ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga agccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700 ccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggcccccaca aaccttcaaa ttaacgaatc aaattaacaa ccataggatg   5940
ataatgcgat tagttttta gccttatttc tggggtaatt aatcagcgaa gcgatgattt   6000
```

```
ttgatctatt aacagatata taaatggaaa agctgcataa ccactttaac taatactttc    6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt    6540 gaacgtgcaa acaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgcttttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct    7523
```

<210> SEQ ID NO 67
<211> LENGTH: 15456
<212> TYPE: DNA
<213> ORGANISM: Artificial Sequence
<220> FEATURE:
<223> OTHER INFORMATION: Template
<400> SEQUENCE: 67

```
aaagagtaat actagagata aacataaaaa atgtagaggt cgagtttaga tgcaagttca      60
aggagcgaaa ggtggatggg taggttatat agggatatag cacagagata tatagcaaag     120
agatactttt gagcaatgtt tgtggaagcg gtattcgcaa tattttagta gctcgttaca     180
gtccggtgcg ttttggttt tttgaaagtg cgtcttcaga gcgcttttgg ttttcaaaag     240
cgctctgaag ttcctatact ttctagagaa taggaacttc ggaataggaa cttcaaagcg     300
tttccgaaaa cgagcgcttc cgaaaatgca acgcgagctg cgcacataca gctcactgtt     360
cacgtcgcac ctatatctgc gtgttgcctg tatatatata tacatgagaa gaacggcata     420
gtgcgtgttt atgcttaaat gcgtactttat atgcgtctat ttatgtagga tgaaaggtag     480
```

```
tctagtacct cctgtgatat tatcccattc catgcggggt atcgtatgct tccttcagca    540
ctacccttta gctgttctat atgctgccac tcctcaattg gattagtctc atccttcaat    600
gctatcattt cctttgatat tggatcatac taagaaacca ttattatcat gacattaacc    660
tataaaaata ggcgtatcac gaggcccttt cgtctcgcgc gtttcggtga tgacggtgaa    720
aacctctgac acatgcagct cccggagacg gtcacagctt gtctgtaagc ggatgccggg    780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc ctttcccgca attttctttt tctattactc ttggcctcct ctagtacact    1020 ctatatttt ttatgcctcg gtaatgattt tcatttttt ttttccacct agcggatgac     1080 tcttttttt tcttagcgat tggcattatc acataatgaa ttatacatta tataaagtaa    1140
tgtgatttct tcgaagaata tactaaaaaa tgagcaggca agataaacga aggcaaagat    1200
gacagagcag aaagccctag taaagcgtat tacaaatgaa accaagattc agattgcgat    1260
ctctttaaag ggtggtcccc tagcgataga gcactcgatc ttcccagaaa agaggcaga    1320 agcagtagca gaacaggcca cacaatcgca agtgattaac gtccacacag gtataggtt    1380 tctggaccat atgatacatg ctctggccaa gcattccggc tggtcgctaa tcgttgagtg    1440
cattggtgac ttacacatag acgaccatca caccactgaa gactgcggga ttgctctcgg    1500
tcaagctttt aaagaggccc taggggccgt gcgtggagta aaaaggtttg gatcaggatt    1560
tgcgcctttg gatgaggcac tttccagagc ggtggtagat ctttcgaaca ggccgtacgc    1620
agttgtcgaa cttggtttgc aaagggagaa agtaggagat ctctcttgcg agatgatccc    1680
gcattttctt gaaagctttg cagaggctag cagaattacc ctccacgttg attgtctgcg    1740
aggcaagaat gatcatcacc gtagtgagag tgcgttcaag gctcttgcgg ttgccataag    1800
agaagccacc tcgcccaatg gtaccaacga tgttccctcc accaaaggtg ttcttatgta    1860
gtgacaccga ttatttaaag ctgcagcata cgatatatat acatgtgtat atatgtatac    1920
ctatgaatgt cagtaagtat gtatacgaac agtatgatac tgaagatgac aaggtaatgc    1980
atcattctat acgtgtcatt ctgaacgagg cgcgcttttc ttttttcttt ttgcttttc     2040 ttttttttc tcttgaactc gacggatcta tgcggtgtga ataccgcac agatgcgtaa      2100 ggagaaaata ccgcatcagg aaattgtaag cgttaatatt ttgttaaaat tcgcgttaaa    2160
tttttgttaa atcagctcat tttttaacca ataggccgaa atcggcaaaa tcccttataa    2220
atcaaaagaa tagaccgaga tagggttgag tgttgttcca gtttggaaca agagtccact    2280
attaaagaac gtggactcca acgtcaaagg gcgaaaaacc gtctatcagg gcgatggccc    2340
actacgtgaa ccatcaccct aatcaagttt tttggggtcg aggtgccgta aagcactaaa    2400
tcggaaccct aaagggagcc ccgatttag agcttgacgg ggaaagccgg cgaacgtggc    2460
gagaaaggaa gggaagaaag cgaaaggagc gggcgctagg gcgctggcaa gtgtagcggt    2520
cacgctgcgc gtaaccacca cacccgccgc gcttaatgcg ccgctacagg gcgcgtccat    2580
tcgccattca ggctgcgcaa ctgttgggaa gggcgcggtg cgggcctctt cgctattacg    2640
ccagctggcg aaagggggat gtgctgcaag gcgattaagt tgggtaacgc cagggttttc    2700
ccagtcacga cgttgtaaaa cgacggccag tgagcgcgcg taatacgact cactataggg    2760
cgaattgggt accgggcccc cctcgaggt cgacggcgcg ccactggtag agagcgactt     2820
tgtatgcccc aattgcgaaa cccgcgatat ccttctcgat tctttagtac ccgaccagga    2880
```

```
caaggaaaag gaggtcgaaa cgttttgaa gaaacaagag gaactacacg gaagctctaa    2940
agatggcaac cagccagaaa ctaagaaaat gaagttgatg gatccaactg gcaccgctgg    3000
cttgaacaac aataccagcc ttccaacttc tgtaaataac ggcggtacgc cagtgccacc    3060
agtaccgtta cctttcggta tacctccttt ccccatgttt ccaatgccct tcatgcctcc    3120
aacggctact atcacaaatc ctcatcaagc tgacgcaagc cctaagaaat gaataacaat    3180
actgacagta ctaaataatt gcctacttgg cttcacatac gttgcatacg tcgatatcga    3240
taataatgat aatgacagca ggattatcgt aatacgtaat agctgaaaat ctcaaaaatg    3300
tgtgggtcat tacgtaaata atgataggaa tgggattctt ctattttttcc tttttccatt    3360
ctagcagccg tcgggaaaac gtggcatcct ctctttcggg ctcaattgga gtcacgctgc    3420
cgtgagcatc ctctctttcc atatctaaca actgagcacg taaccaatgg aaaagcatga    3480
gcttagcgtt gctccaaaaa agtattggat ggttaatacc atttgtctgt tctcttctga    3540
ctttgactcc tcaaaaaaaa aaatctcaaa tcaacagatc gcttcaatta cgccctcaca    3600
aaaactttt tccttcttct tcgcccacgt taaatttat ccctcatgtt gtctaacgga    3660
tttctgcact tgatttatta taaaagaca aagacataat acttctctat caatttcagt    3720
tattgttctt ccttgcgtta ttcttctgtt cttcttttc ttttgtcata tataaccata    3780
accaagtaat acatattcaa actagtatga ctgacaaaaa aactcttaaa gacttaagaa    3840
atcgtagttc tgtttacgat tcaatggtta aatcacctaa tcgtgctatg ttgcgtgcaa    3900
ctggtatgca agatgaagac tttgaaaaac ctatcgtcgg tgtcatttca acttgggctg    3960
aaaacacacc ttgtaatatc cacttacatg actttggtaa actagccaaa gtcggtgtta    4020
aggaagctgg tgcttggcca gttcagttcg gaacaatcac ggtttctgat ggaatcgcca    4080
tgggaaccca aggaatgcgt ttctccttga catctcgtga tattattgca gattctattg    4140
aagcagccat gggaggtcat aatgcggatg cttttgtagc cattggcggt tgtgataaaa    4200
acatgcccgg ttctgttatc gctatggcta acatggatat cccagccatt tttgcttacg    4260
gcggaacaat tgcacctggt aatttagacg gcaaagatat cgatttagtc tctgtctttg    4320
aaggtgtcgg ccattggaac cacggcgata tgaccaaaga agaagttaaa gctttggaat    4380
gtaatgcttg tcccggtcct ggaggctgcg gtggtatgta tactgctaac acaatggcga    4440
cagctattga agttttggga cttagccttc cgggttcatc ttctcacccg gctgaatccg    4500
cagaaaagaa agcagatatt gaagaagctg gtcgcgctgt tgtcaaaatg ctcgaaatgg    4560
gcttaaaacc ttctgacatt ttaacgcgtg aagcttttga agatgctatt actgtaacta    4620
tggctctggg aggttcaacc aactcaaccc ttccctctt agctattgcc catgctgcta    4680
atgtggaatt gacacttgat gatttcaata ctttccaaga aaaagttcct catttggctg    4740
atttgaaacc ttctggtcaa tatgtattcc aagacctta caaggtcgga ggggtaccag    4800
cagttatgaa atatctcctt aaaaatggct tccttcatgg tgaccgtatc acttgtactg    4860
gcaaaacagt cgctgaaaat ttgaaggctt ttgatgattt aacacctggt caaaaggtta    4920
ttatgccgct tgaaaatcct aaacgtgaag atggtccgct cattattctc catggtaact    4980
tggctccaga cggtgccgtt gccaaagttt ctggtgtaaa agtgcgtcgt catgtcggtc    5040
ctgctaaggt cttaattct gaagaagaag ccattgaagc tgtcttgaat gatgatattg    5100
ttgatggtga tgttgttgtc gtacgttttg taggaccaaa gggcggtcct ggtatgcctg    5160
aaatgctttc cctttcatca atgattgttg gtaaggggca aggtgaaaaa gttgcccttc    5220
```

```
tgacagatgg ccgcttctca ggtggtactt atggtcttgt cgtgggtcat atcgctcctg    5280
aagcacaaga tggcggtcca atcgcctacc tgcaaacagg agacatagtc actattgacc    5340
aagacactaa ggaattacac tttgatatct ccgatgaaga gttaaaacat cgtcaagaga    5400
ccattgaatt gccaccgctc tattcacgcg gtatccttgg taaatatgct cacatcgttt    5460
cgtctgcttc taggggagcc gtaacagact tttggaagcc tgaagaaact ggcaaaaaat    5520
gttgtcctgg ttgctgtggt taagcggccg cgttaattca aattaattga tatagttttt    5580
taatgagtat tgaatctgtt tagaaataat ggaatattat ttttatttat ttatttatat    5640
tattggtcgg ctcttttctt ctgaaggtca atgacaaaat gatatgaagg aaataatgat    5700
ttctaaaatt ttacaacgta agatatttt acaaaagcct agctcatctt ttgtcatgca    5760
ctattttact cacgcttgaa attaacggcc agtccactgc ggagtcattt caaagtcatc    5820
ctaatcgatc tatcgttttt gatagctcat tttggagttc gcgattgtct tctgttattc    5880
acaactgttt taattttat ttcattctgg aactcttcga gttctttgta aagtctttca    5940
tagtagctta ctttatcctc aacatattt aacttcatgt caatttcggc tcttaaattt    6000
tccacatcat caagttcaac atcatctttt aacttgaatt tattctctag ctcttccaac    6060
caagcctcat tgctccttga tttactggtg aaaagtgata cactttgcgc gcaatccagg    6120
tcaaaacttt cctgcaaaga attcaccaat ttctcgacat catagtacaa tttgttttgt    6180
tctcccatca caatttaata tacctgatgg attcttatga agcgctgggt aatggacgtg    6240
tcactctact tcgccttttt ccctactcct tttagtacgg aagacaatgc taataaataa    6300
gagggtaata ataatattat taatcggcaa aaaagattaa acgccaagcg tttaattatc    6360
agaaagcaaa cgtcgtacca atccttgaat gcttcccaat tgtatattaa gagtcatcac    6420
agcaacatat tcttgttatt aaattaatta ttattgattt ttgatattgt ataaaaaaac    6480
caaatatgta taaaaaagt gaataaaaaa taccaagtat ggagaaatat attagaagtc    6540
tatacgttaa accacccggg ccccccctcg aggtcgacgg tatcgataag cttgatatcg    6600
aattcctgca gcccggggga tccactagtt ctagagcggc cgctctagaa ctagtaccac    6660
aggtgttgtc ctctgaggac ataaaataca caccgagatt catcaactca ttgctggagt    6720
tagcatatct acaattgggt gaaatgggga gcgatttgca ggcatttgct cggcatgccg    6780
gtagaggtgt ggtcaataag agcgacctca tgctatacct gagaaagcaa cctgacctac    6840
aggaaagagt tactcaagaa taagaatttt cgttttaaaa cctaagagtc actttaaaat    6900
ttgtatacac ttatttttt tataacttat ttaataataa aaatcataaa tcataagaaa    6960
ttcgcttact cttaattaat caggcagcgc ctgcgttcga gaggatgatc ttcatcgcct    7020
tctccttggc gccattgagg aatacctgat aggcgtgctc gatctcggcc agctcgaagc    7080
gatgggtaat catcttcttc aacggaagct tgtcggtcga ggcgaccttc atcagcatgg    7140
gcgtcgtgtt cgtgttcacc agtcccgtgg tgatcgtcag gttcttgatc cagagcttct    7200
gaatctcgaa gtcaaccttg acgccatgca cgccgacgtt ggcgatgtgc gcgccgggct    7260
tgacgatctc ctggcagatg tcccaagtcg ccggtatgcc caccgcctcg atcgcaacat    7320
cgactccctc tgccgcaatc ctatgcacgg cttcgacaac gttctccgtg ccggagttga    7380
tggtgtgcgt tgccccgagc tccttggcga gctggaggcg attctcgtcc atgtcgatca    7440
cgatgatggt cgaggggag tagaactggg cggtcaacag tacggacatg ccgacggggc    7500
ccgcgccgac aatagccacc gcatcgcccg gctggacatt cccatactgg acgccgattt    7560
cgtggccggt gggcaggatg tcgctcagca ggacggcgat ttcgtcgtca attgtctggg    7620
```

```
ggatcttgta gaggctgttg tcggcatgcg ggatgcggac gtattcggcc tgcacgccat    7680
cgatcatgta acccaggatc cacccgccgt cgcggcaatg ggagtaaagc tgcttcttgc    7740
agtagtcgca cgagccgcaa gaagtgacgc aggaaatcag gaccttgtcg cctttcttga    7800
actgcgtgac actctcgccc acttcctcga tgacgcctac cccttcatgg cccaggatgc    7860
gcccgtcggc gacctctgga ttcttgcctt tgtagatgcc gagatccgtg ccgcagatcg    7920
tggtcttcaa aacccgtact actacatccg tgggcttttg aagggtgggc ttgggcttgt    7980
cttcaagcga gatcttgtgg tcaccgtgat aaaccagagc tttcatcctc agctattgta    8040
atatgtgtgt ttgtttggat tattaagaag aataattaca aaaaaaatta caaaggaagg    8100
taattacaac agaattaaga aaggacaaga aggaggaaga gaatcagttc attatttctt    8160
ctttgttata taacaaaccc aagtagcgat ttggccatac attaaaagtt gagaaccacc    8220
ctccctggca acagccacaa ctcgttacca ttgttcatca cgatcatgaa actcgctgtc    8280
agctgaaatt tcacctcagt ggatctctct ttttattctt catcgttcca ctaaccttt     8340 tccatcagct ggcagggaac ggaaagtgga atcccattta gcgagcttcc tcttttcttc    8400
aagaaaagac gaagcttgtg tgtgggtgcg cgcgctagta tctttccaca ttaagaaata    8460
taccataaag gttacttaga catcactatg gctatatata tatatatata tatatatgta    8520
acttagcacc atcgcgcgtg catcactgca tgtgttaacc gaaagtttg gcgaacactt     8580 caccgacacg gtcatttaga tctgtcgtct gcattgcacg tcccttagcc ttaaatccta    8640
ggcgggagca ttctcgtgta attgtgcagc ctgcgtagca actcaacata gcgtagtcta    8700
cccagttttt caagggttta tcgttagaag attctccctt ttcttcctgc tcacaaatct    8760
taaagtcata cattgcacga ctaaatgcaa gcatgcggat cccccgggct gcaggaattc    8820
gatatcaagc ttatcgatac cgtcgactgg ccattaatct ttcccatatt agatttcgcc    8880
aagccatgaa agttcaagaa aggtctttag acgaattacc cttcatttct caaactggcg    8940
tcaagggatc ctggtatggt tttatcgttt tatttctggt tcttatagca tcgttttgga    9000
cttctctgtt cccattaggc ggttcaggag ccagcgcaga atcattcttt gaaggatact    9060 tatccttttcc aattttgatt gtctgttacg ttggacataa actgtatact agaaattgga    9120
ctttgatggt gaaactagaa gatatggatc ttgataccgg cagaaaacaa gtagatttga    9180
ctcttcgtag ggaagaaatg aggattgagc gagaaacatt agcaaaaaga tccttcgtaa    9240
caagattttt acatttctgg tgttgaaggg aaagatatga gctatacagc ggaatttcca    9300
tatcactcag attttgttat ctaattttt ccttcccacg tccgcgggaa tctgtgtata     9360
ttactgcatc tagatatatg ttatcttatc ttggcgcgta catttaattt tcaacgtatt    9420
ctataagaaa ttgcgggagt ttttttcatg tagatgatac tgactgcacg caaatatagg    9480
catgatttat aggcatgatt tgatggctgt accgatagga acgctaagag taacttcaga    9540
atcgttatcc tggcggaaaa aattcatttg taaactttaa aaaaaaagc caatatcccc     9600 aaaattatta agagcgcctc cattattaac taaaatttca ctcagcatcc acaatgtatc    9660
aggtatctac tacagatatt acatgtggcg aaaaagacaa gaacaatgca atagcgcatc    9720
aagaaaaaac acaaagcttt caatcaatga atcgaaaatg tcattaaaat agtatataaa    9780
ttgaaactaa gtcataaagc tataaaaaga aaatttattt aaatgcaaga tttaaagtaa    9840
attcacggcc ctgcaggcct cagctcttgt tttgttctgc aaataactta cccatctttt    9900
tcaaaacttt aggtgcaccc tcctttgcta gaataagttc tatccaatac atcctatttg    9960
```

```
gatctgcttg agcttctttc atcacggata cgaattcatt ttctgttctc acaattttgg    10020
acacaactct gtcttccgtt gccccgaaac tttctggcag ttttgagtaa ttccacatag    10080
gaatgtcatt ataactctgg ttcggaccat gaatttccct ctcaaccgtg taaccatcgt    10140
tattaatgat aaagcagatt gggtttatct tctctctaat ggctagtcct aattcttgga    10200
cagtcagttg caatgatcca tctccgataa acaataaatg tctagattct ttatctgcaa    10260
tttggctgcc tagagctgcg gggaaagtgt atcctataga tccccacaag ggttgaccaa    10320
taaaatgtga tttcgatttc agaaatatag atgaggcacc gaagaaagaa gtgccttgtt    10380
cagccacgat cgtctcatta ctttgggtca aattttcgac agcttgccac agtctatctt    10440
gtgacaacag cgcgttagaa ggtacaaaat cttcttgctt tttatctatg tacttgcctt    10500
tatattcaat ttcggacaag tcaagaagag atgatatcag ggattcgaag tcgaaatttt    10560
ggattctttc gttgaaaatt ttaccttcat cgatattcaa ggaaatcatt ttattttcat    10620
taagatggtg agtaaatgca cccgtactag aatcggtaag ctttacaccc aacataagaa    10680
taaaatcagc agattccaca aattccttca gtttgctc tgacagagta ccgttgtaaa    10740
tccccaaaaa tgagggcaat gcttcatcaa cagatgattt accaaagttc aaagtagtaa    10800
taggtaactt agtctttgaa ataaactgag taacagtctt ctctaggccg aacgatataa    10860
tttcatggcc tgtgattaca attggttt ct tggcattctt cagactttcc tgtattttgt    10920
tcagaatctc ttgatcagat gtattcgacg tggaattttc cttcttaaga ggcaaggatg    10980
gttttttcagc cttagcggca gctacatcta caggtaaatt gatgtaaacc ggctttcttt    11040
cctttagtaa ggcagacaac actctatcaa tttcaacagt tgcattctcg gctgtcaata    11100
aagtcctggc agcagtaacc ggttcgtgca tcttcataaa gtgcttgaaa tcaccatcag    11160
ccaacgtatg gtgaacaaac ttaccttcgt tctgcacttt cgaggtagga gatcccacga    11220
tctcaacaac aggcaggttc tcagcatagg agcccgctaa gccattaact gcggataatt    11280
cgccaacacc aaatgtagtc aagaatgccg cagcctttt cgttcttgcg tacccgtcgg    11340
ccatatagga ggcatttaac tcattagcat ttcccaccca tttcatatct ttgtgtgaaa    11400
taatttgatc tagaaattgc aaattgtagt cacctggtac tccgaatatt tcttctatac    11460
ctaattcgtg taatctgtcc aacagatagt cacctactgt atacattttg tttactagtt    11520
tatgtgtgtt tattcgaaac taagttcttg gtgttttaaa actaaaaaaa agactaacta    11580
taaaagtaga atttaagaag tttaagaaat agatttacag aattacaatc aatacctacc    11640
gtctttatat acttattagt caagtagggg aataatttca gggaactggt ttcaaccttt    11700
ttttcagct tttccaaat cagagagagc agaaggtaat agaaggtgta agaaaatgag    11760
atagatacat gcgtgggtca attgccttgt gtcatcattt actccaggca ggttgcatca    11820
ctccattgag gttgtgcccg ttttttgcct gtttgtgccc ctgttctctg tagttgcgct    11880
aagagaatgg acctatgaac tgatggttgg tgaagaaaac aatatttgg tgctgggatt    11940
cttttttttt ctggatgcca gcttaaaaag cgggctccat tatatttagt ggatgccagg    12000
aataaactgt tcacccagac acctacgatg ttatatattc tgtgtaaccc gccccctatt    12060
ttgggcatgc acgggttaca gcagaattaa aaggctaatt ttttgactaa ataaagttag    12120
gaaaatcact actattaatt atttacgtat tctttgaaat ggcagtattg ataatgataa    12180
actcgaactg aaaaagcgtg ttttttattc aaaaatgattc taactcccctt acgtaatcaa    12240
ggaatctttt tgccttggcc tccgcgtcat taaacttctt gttgttgacg ctaacattca    12300
acgctagtat atattcgttt ttttcaggta agttctttc aacgggtctt actgatgagg    12360
```

```
cagtcgcgtc tgaacctgtt aagaggtcaa atatgtcttc ttgaccgtac gtgtcttgca    12420
tgttattagc tttgggaatt tgcatcaagt cataggaaaa tttaaatctt ggctctcttg    12480
ggctcaaggt gacaaggtcc tcgaaaatag ggcgcgcccc accgcggtgg agctccagct    12540
tttgttccct ttagtgaggg ttaattgcgc gcttggcgta atcatggtca tagctgtttc    12600
ctgtgtgaaa ttgttatccg ctcacaattc cacacaacat acgagccgga agcataaagt    12660
gtaaagcctg gggtgcctaa tgagtgagct aactcacatt aattgcgttg cgctcactgc    12720
ccgctttcca gtcgggaaac ctgtcgtgcc agctgcatta tgaatcggc caacgcgcgg     12780 ggagaggcgg tttgcgtatt gggcgctctt ccgcttcctc gctcactgac tcgctgcgct    12840
cggtcgttcg gctgcggcga gcggtatcag ctcactcaaa ggcggtaata cggttatcca    12900
cagaatcagg ggataacgca ggaaagaaca tgtgagcaaa aggccagcaa aaggccagga    12960
accgtaaaaa ggccgcgttg ctggcgtttt tccataggct ccgcccccct gacgagcatc    13020
acaaaaatcg acgctcaagt cagaggtggc gaaacccgac aggactataa agataccagg    13080
cgtttccccc tggaagctcc ctcgtgcgct ctcctgttcc gaccctgccg cttaccggat    13140
acctgtccgc ctttctccct tcgggaagcg tggcgctttc tcatagctca cgctgtaggt    13200
atctcagttc ggtgtaggtc gttcgctcca agctgggctg tgtgcacgaa ccccccgttc    13260
agcccgaccg ctgcgcctta tccggtaact atcgtcttga gtccaacccg gtaagacacg    13320
acttatcgcc actggcagca gccactggta acaggattag cagagcgagg tatgtaggcg    13380
gtgctacaga gttcttgaag tggtggccta actacggcta cactagaaga acagtatttg    13440
gtatctgcgc tctgctgaag ccagttacct tcggaaaaag agttggtagc tcttgatccg    13500
gcaaacaaac caccgctggt agcggtggtt tttttgtttg caagcagcag attacgcgca    13560
gaaaaaaagg atctcaagaa gatcctttga tcttttctac ggggtctgac gctcagtgga    13620
acgaaaactc acgttaaggg attttggtca tgagattatc aaaaaggatc ttcacctaga    13680
tccttttaaa ttaaaaatga agttttaaat caatctaaag tatatatgag taaacttggt    13740
ctgacagtta ccaatgctta atcagtgagg cacctatctc agcgatctgt ctatttcgtt    13800
catccatagt tgcctgactc cccgtcgtgt agataactac gatacgggag ggcttaccat    13860
ctggccccag tgctgcaatg ataccgcgag acccacgctc accggctcca gatttatcag    13920
caataaacca gccagccgga agggccgagc gcagaagtgg tcctgcaact ttatccgcct    13980
ccatccagtc tattaattgt tgccgggaag ctagagtaag tagttcgcca gttaatagtt    14040
tgcgcaacgt tgttgccatt gctacaggca tcgtggtgtc acgctcgtcg tttggtatgg    14100
cttcattcag ctccggttcc caacgatcaa ggcgagttac atgatccccc atgttgtgca    14160
aaaaagcggt tagctccttc ggtcctccga tcgttgtcag aagtaagttg gccgcagtgt    14220
tatcactcat ggttatggca gcactgcata attctcttac tgtcatgcca tccgtaagat    14280
gcttttctgt gactggtgag tactcaacca agtcattctg agaatagtgt atgcggcgac    14340
cgagttgctc ttgcccggcg tcaatacggg ataataccgc gccacatagc agaactttaa    14400
aagtgctcat cattggaaaa cgttcttcgg ggcgaaaact ctcaaggatc ttaccgctgt    14460
tgagatccag ttcgatgtaa cccactcgtg cacccaactg atcttcagca tcttttactt    14520
tcaccagcgt ttctgggtga gcaaaaacag gaaggcaaaa tgccgcaaaa aagggaataa    14580
gggcgacacg gaaatgttga atactcatac tcttcctttt tcaatattat tgaagcattt    14640
atcagggtta ttgtctcatg agcggataca tatttgaatg tatttagaaa aataaacaaa    14700
```

```
tagggggttcc gcgcacattt ccccgaaaag tgccacctga acgaagcatc tgtgcttcat    14760
tttgtagaac aaaaatgcaa cgcgagagcg ctaattttc aaacaaagaa tctgagctgc     14820
atttttacag aacagaaatg caacgcgaaa gcgctatttt accaacgaag aatctgtgct    14880 tcattttttgt aaaacaaaaa tgcaacgcga gagcgctaat ttttcaaaca agaatctga    14940 gctgcatttt tacagaacag aaatgcaacg cgagagcgct attttaccaa caaagaatct    15000
atacttcttt tttgttctac aaaaatgcat cccgagagcg ctatttttct aacaaagcat    15060
cttagattac tttttttctc ctttgtgcgc tctataatgc agtctcttga taacttttttg   15120 cactgtaggt ccgttaaggt tagaagaagg ctactttggt gtctattttc cttccataa     15180 aaaaagcctg actccacttc ccgcgtttac tgattactag cgaagctgcg ggtgcatttt    15240
ttcaagataa aggcatcccc gattatattc tataccgatg tggattgcgc atactttgtg    15300
aacagaaagt gatagcgttg atgattcttc attggtcaga aaattatgaa cggtttcttc    15360
tattttgtct ctatatacta cgtataggaa atgtttacat tttcgtattg ttttcgattc    15420
actctatgaa tagttcttac tacaattttt ttgtct                              15456

<210> SEQ ID NO 68
<211> LENGTH: 1559
<212> TYPE: DNA
<213> ORGANISM: Artificial Sequence
<220> FEATURE:
<223> OTHER INFORMATION: Template

<400> SEQUENCE: 68
gcattgcgga ttacgtattc taatgttcag taccgttcgt ataatgtatg ctatacgaag       60
ttatgcagat tgtactgaga gtgcaccata ccacctttc aattcatcat tttttttta       120 ttcttttttt tgatttcggt ttccttgaaa ttttttgat tcggtaatct ccgaacagaa      180
ggaagaacga aggaaggagc acagacttag attggtatat atacgcatat gtagtgttga      240
agaaacatga aattgcccag tattcttaac ccaactgcac agaacaaaaa cctgcaggaa      300
acgaagataa atcatgtcga agctacata taaggaacgt gctgctactc atcctagtcc       360
tgttgctgcc aagctatttta atatcatgca cgaaaagcaa acaaacttgt gtgcttcatt      420
ggatgttcgt accaccaagg aattactgga gttagttgaa gcattaggtc ccaaaatttg      480
tttactaaaa acacatgtgg atatcttgac tgattttttcc atggagggca cagttaagcc     540
gctaaaggca ttatccgcca agtacaattt tttactcttc gaagacagaa aatttgctga      600
cattggtaat acagtcaaat tgcagtactc tgcgggtgta tacagaatag cagaatgggc      660
agacattacg aatgcacacg gtgtggtggg cccaggtatt gttagcggtt tgaagcaggc      720
ggcagaagaa gtaacaaagg aacctagagg ccttttgatg ttagcagaat tgtcatgcaa      780 gggctccta tctactggag aatatactaa gggtactgtt gacattgcga gagcgacaa        840 agattttgtt atcggcttta ttgctcaaag agacatgggt ggaagagatg aaggttacga      900
ttggttgatt atgacacccg gtgtgggttt agatgacaag ggagacgcat gggtcaaca      960 gtatagaacc gtggatgatg tggtctctac aggatctgac attattattg ttggaagagg     1020
actatttgca aagggaaggg atgctaaggt agagggtgaa cgttacagaa agcaggctg      1080 ggaagcatat ttgagaagat gcggccagca aaactaaaaa actgtattat aagtaaatgc     1140
atgtatacta aactcacaaa ttagagcttc aatttaatta tatcagttat taccctatgc    1200
ggtgtgaaat accgcacaga tgcgtaagga gaaataccg catcaggaaa ttgtaaacgt      1260
taatattttg ttaaaattcg cgttaaattt ttgttaaatc agctcatttt ttaaccaata    1320
```

```
ggccgaaatc ggcaaaatcc cttataaatc aaaagaatag accgagatag ggttgagtgt   1380
tgttccagtt tggaacaaga gtccactatt aaagaacgtg gactccaacg tcaaagggcg   1440
aaaaaccgtc tatcagggcg atggcccact acgtgaacca tcaccctaat caagataact   1500
tcgtataatg tatgctatac gaacggtacc agtgatgata caacgagtta gccaaggtg    1559
```

<210> SEQ ID NO 69
<211> LENGTH: 1047
<212> TYPE: DNA
<213> ORGANISM: Alcaligenes xylosoxydans

<400> SEQUENCE: 69

```
atgaaagctc tggtttatca cggtgaccac aagatctcgc ttgaagacaa gcccaagccc     60
acccttcaaa agcccacgga tgtagtagta cgggttttga agaccacgat ctgcggcacg    120
gatctcggca tctacaaagg caagaatcca gaggtcgccg acgggcgcat cctgggccat    180 gaagggtag cgtcatcga ggaagtgggc gagagtgtca cgcagttcaa gaaaggcgac    240
aaggtcctga tttcctgcgt cacttcttgc ggctcgtgcg actactgcaa gaagcagctt    300
tactcccatt gccgcgacgg cggtggatc ctgggttaca tgatcgatgg cgtgcaggcc    360
gaatacgtcc gcatcccgca tgccgacaac agcctctaca agatccccca gacaattgac    420
gacgaaatcg ccgtcctgct gagcgacatc ctgcccaccg ccacgaaat cggcgtccag    480 tatgggaatg tccagccggg cgatgcggtg gctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccggcgac ttgggacatc tgccaggaga tcgtcaagcc cggcgcgcac    780
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                        1047
```

<210> SEQ ID NO 70
<211> LENGTH: 348
<212> TYPE: PRT
<213> ORGANISM: Alcaligenes xylosoxydans

<400> SEQUENCE: 70

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95
```

```
Lys Lys Gln Leu Tyr Ser His Cys Arg Asp Gly Gly Trp Ile Leu Gly
            100                 105                 110
Tyr Met Ile Asp Gly Val Gln Ala Glu Tyr Val Arg Ile Pro His Ala
        115                 120                 125
Asp Asn Ser Leu Tyr Lys Ile Pro Gln Thr Ile Asp Asp Glu Ile Ala
    130                 135                 140
Val Leu Leu Ser Asp Ile Leu Pro Thr Gly His Glu Ile Gly Val Gln
145                 150                 155                 160
Tyr Gly Asn Val Gln Pro Gly Asp Ala Val Ala Ile Val Gly Ala Gly
                165                 170                 175
Pro Val Gly Met Ser Val Leu Leu Thr Ala Gln Phe Tyr Ser Pro Ser
            180                 185                 190
Thr Ile Ile Val Ile Asp Met Asp Glu Asn Arg Leu Gln Leu Ala Lys
        195                 200                 205
Glu Leu Gly Ala Thr His Thr Ile Asn Ser Gly Thr Glu Asn Val Val
    210                 215                 220
Glu Ala Val His Arg Ile Ala Ala Glu Gly Val Asp Val Ala Ile Glu
225                 230                 235                 240
Ala Val Gly Ile Pro Ala Thr Trp Asp Ile Cys Gln Glu Ile Val Lys
                245                 250                 255
Pro Gly Ala His Ile Ala Asn Val Gly Val His Gly Val Lys Val Asp
            260                 265                 270
Phe Glu Ile Gln Lys Leu Trp Ile Lys Asn Leu Thr Ile Thr Thr Gly
        275                 280                 285
Leu Val Asn Thr Asn Thr Thr Pro Met Leu Met Lys Val Ala Ser Thr
    290                 295                 300
Asp Lys Leu Pro Leu Lys Lys Met Ile Thr His Arg Phe Glu Leu Ala
305                 310                 315                 320
Glu Ile Glu His Ala Tyr Gln Val Phe Leu Asn Gly Ala Lys Glu Lys
                325                 330                 335
Ala Met Lys Ile Ile Leu Ser Asn Ala Gly Ala Ala
            340                 345

<210> SEQ ID NO 71
<211> LENGTH: 1644
<212> TYPE: DNA
<213> ORGANISM: Artificial Sequence
<220> FEATURE:
<223> OTHER INFORMATION: codon optimized L. lactis kivD coding region
      for S. cerevisiae expression

<400> SEQUENCE: 71
atgtatacag taggtgacta tctgttggac agattacacg aattaggtat agaagaaata      60 ttcgagtac caggtgacta caatttgcaa tttctagatc aaattatttc acacaaagat     120
atgaaatggg tgggaaatgc taatgagtta atgcctcct atatggccga cgggtacgca     180
agaacgaaaa aggctgcggc attcttgact acatttggtg ttggcgaatt atccgcagtt     240
aatggcttag cgggctccta tgctgagaac ctgcctgttg ttgagatcgt gggatctcct     300
acctcgaaag tgcagaacga aggtaagttt gttcaccata cgttggctga tggtgatttc     360
aagcacttta tgaagatgca cgaaccggtt actgctgcca ggactttatt gacagccgag     420
aatgcaactg ttgaaattga tagtgttg tctgccttac taaggaaag aaagccggtt     480 tacatcaatt tacctgtaga gtagctgcc gctaaggctg aaaaaccatc cttgcctctt     540
aagaaggaaa attccacgtc gaatacatct gatcaagaga ttctgaacaa atacaggaa     600
```

```
agtctgaaga atgccaagaa accaattgta atcacaggcc atgaaattat atcgttcggc      660
ctagagaaga ctgttactca gtttatttca aagactaagt tacctattac tactttgaac      720
tttggtaaat catctgttga tgaagcattg ccctcatttt tggggattta caacggtact      780
ctgtcagagc caaacttgaa ggaatttgtg gaatctgctg attttattct tatgtttgggt     840 gtaaagctta ccgattctag tacgggtgca tttactcacc atcttaatga aaataaaatg      900
atttccttga atatcgatga aggtaaaatt ttcaacgaaa gaatccaaaa tttcgacttc      960
gaatccctga tatcatctct tcttgacttg tccgaaattg aatataaagg caagtacata     1020
gataaaaagc aagaagattt tgtaccttct aacgcgctgt tgtcacaaga tagactgtgg     1080
caagctgtcg aaaatttgac ccaaagtaat gagacgatcg tggctgaaca aggcacttct     1140
ttcttcggtg cctcatctat atttctgaaa tcgaaatcac attttattgg tcaacccttg     1200
tggggatcta taggatacac tttccccgca gctctaggca gccaaattgc agataaagaa     1260
tctagacatt tattgtttat cggagatgga tcattgcaac tgactgtcca agaattagga     1320
ctagccatta gagagaagat aaacccaatc tgctttatca ttaataacga tggttacacg     1380
gttgagaggg aaattcatgg tccgaaccag agttataatg acattcctat gtggaattac     1440
tcaaaactgc cagaaagttt cggggcaacg gaagacagag ttgtgtccaa aattgtgaga     1500
acagaaaatg aattcgtatc cgtgatgaaa gaagctcaag cagatccaaa taggatgtat     1560
tggatagaac ttattctagc aaaggagggt gcacctaaag ttttgaaaaa gatgggtaag     1620
ttatttgcag aacaaaacaa gagc                                            1644

<210> SEQ ID NO 72
<211> LENGTH: 753
<212> TYPE: DNA
<213> ORGANISM: Saccharomyces cerevisiae

<400> SEQUENCE: 72
gcatgcttgc atttagtcgt gcaatgtatg actttaagat tgtgagcag  gaagaaaagg       60 gagaatcttc taacgataaa cccttgaaaa actgggtaga ctacgctatg ttgagttgct      120
acgcaggctg cacaattaca cgagaatgct cccgcctagg atttaaggct aagggacgtg      180
caatgcagac gacagatcta aatgaccgtg tcggtgaagt gttcgccaaa cttttcggtt      240
aacacatgca gtgatgcacg cgcgatggtg ctaagttaca tatatatata tatagccata      300
gtgatgtcta agtaacccttt atggtatatt tcttaatgtg gaaagatact agcgcgcgca      360
cccacacaca agcttcgtct tttcttgaag aaaagaggaa gctcgctaaa tgggattcca      420 cttttccgttc cctgccagct gatggaaaaa ggttagtgga acgatgaaga ataaaaagag     480
agatccactg aggtgaaatt tcagctgaca gcgagtttca tgatcgtgat gaacaatggt     540
aacgagttgt ggctgttgcc agggagggtg gttctcaact tttaatgtat ggccaaatcg     600
ctacttgggt ttgttatata acaaagaaga ataatgaac tgattctctt cctccttctt      660
gtcctttctt aattctgttg taattacctt cctttgtaat tttttttgta attattcttc     720
ttaataatcc aaacaaacac acatattaca ata                                  753

<210> SEQ ID NO 73
<211> LENGTH: 316
<212> TYPE: DNA
<213> ORGANISM: Saccharomyces cerevisiae

<400> SEQUENCE: 73
gagtaagcga atttcttatg atttatgatt tttattatta aataagttat aaaaaaaata       60
```

```
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtatttta tgtcctcaga    300
ggacaacacc tgtggt                                                    316
```

```
<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
ggaattcaca catgaaagct ctggtttatc                                      30

<210> SEQ ID NO 75
<211> LENGTH: 28
<212> TYPE: DNA
<213> ORGANISM: Artificial Sequence
<220> FEATURE:
<223> OTHER INFORMATION: primer

<400> SEQUENCE: 75
gcgtccaggg cgtcaaagat caggcagc                                        28

<210> SEQ ID NO 76
<211> LENGTH: 55
<212> TYPE: DNA
<213> ORGANISM: Artificial Sequence
<220> FEATURE:
<223> OTHER INFORMATION: primer

<400> SEQUENCE: 76
aaacaaacac acatattaca atagctgagg atgaaagctc tggtttatca cggtg          55

<210> SEQ ID NO 77
<211> LENGTH: 55
<212> TYPE: DNA
<213> ORGANISM: Artificial Sequence
<220> FEATURE:
<223> OTHER INFORMATION: primer

<400> SEQUENCE: 77
atcataagaa attcgcttac tcttaattaa tcaggcagcg cctgcgttcg agagg          55

<210> SEQ ID NO 78
<211> LENGTH: 8994
<212> TYPE: DNA
<213> ORGANISM: Artificial Sequence
<220> FEATURE:
<223> OTHER INFORMATION: constructed plasmid

<400> SEQUENCE: 78
```

```
ctagttctag agcggccgcc accgcggtgg agctccagct tttgttccct ttagtgaggg    60
ttaattgcgc gcttggcgta atcatggtca tagctgtttc ctgtgtgaaa ttgttatccg    120
ctcacaattc cacacaacat aggagccgga agcataaagt gtaaagcctg gggtgcctaa    180
tgagtgaggt aactcacatt aattgcgttg cgctcactgc ccgctttcca gtcgggaaac    240
ctgtcgtgcc agctgcatta atgaatcggc caacgcgcgg ggagaggcgg tttgcgtatt    300
```

```
gggcgctctt ccgcttcctc gctcactgac tcgctgcgct cggtcgttcg gctgcggcga    360
gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga cgaagcatc tgtgcttcat tttgtagaac aaaaatgcaa   2280
cgcgagagcg ctaattttc aaacaaagaa tctgagctgc attttacag aacagaaatg   2340
caacgcgaaa gcgctatttt accaacgaag aatctgtgct tcattttgt aaaacaaaaa   2400
tgcaacgcga gagcgctaat ttttcaaaca agaatctga ctgcatttt tacagaacag   2460
aaatgcaacg cgagagcgct attttaccaa caaagaatct atacttcttt tttgttctac   2520
aaaaatgcat cccgagagcg ctattttct aacaaagcat cttagattac ttttttctc   2580
ctttgtgcgc tctataatgc agtctcttga taacttttg cactgtaggt ccgttaaggt   2640
tagaagaagg ctactttggt gtctattttc tcttccataa aaaaagcctg actccacttc   2700
```

```
ccgcgtttac tgattactag cgaagctgcg ggtgcatttt ttcaagataa aggcatcccc    2760
gattatattc tataccgatg tggattgcgc atactttgtg aacagaaagt gatagcgttg    2820
atgattcttc attggtcaga aaattatgaa cggtttcttc tattttgtct ctatatacta    2880
cgtataggaa atgtttacat tttcgtattg ttttcgattc actctatgaa tagttcttac    2940 tacaatttt  ttgtctaaag agtaatacta gagataaaca taaaaaatgt agaggtcgag    3000
tttagatgca agttcaagga gcgaaaggtg gatgggtagg ttatataggg atatagcaca    3060
gagatatata gcaaagagat acttttgagc aatgtttgtg gaagcggtat tcgcaatatt    3120
ttagtagctc gttacagtcc ggtgcgtttt tggttttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgtttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaaataggcg tatcacgagg cccttcgtc  tcgcgcgttt    3660 cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaactttc accattatgg    3900
gaaatgcttc aagaaggtat tgacttaaac tccatcaaat ggtcaggtca ttgagtgttt    3960
tttatttgtt gtattttttt tttttagag  aaaatcctcc aatatcaaat taggaatcgt    4020
agtttcatga ttttctgtta cacctaactt tttgtgtggt gccctcctcc ttgtcaatat    4080
taatgttaaa gtgcaattct ttttccttat cacgttgagc cattagtatc aatttgctta    4140
cctgtattcc tttactatcc tccttttcct ccttcttgat aaatgtatgt agattgcgta    4200
tatagtttcg tctaccctat gaacatattc catttgtaa  tttcgtgtcg tttctattat    4260
gaatttcatt tataaagttt atgtacaaat atcataaaaa aagagaatct ttttaagcaa    4320
ggattttctt aacttcttcg gcgacagcat caccgacttc ggtggtactg ttggaaccac    4380
ctaaatcacc agttctgata cctgcatcca aaacctttt  aactgcatct tcaatggcct    4440
taccttcttc aggcaagttc aatgacaatt tcaacatcat tgcagcagac aagatagtgg    4500
cgatagggtc aaccttattc tttggcaaat ctggagcaga accgtggcat ggttcgtaca    4560
aaccaaatgc ggtgttcttg tctggcaaag aggccaagga cgcagatggc aacaaaccca    4620
aggaacctgg gataacggag gcttcatcgg agatgatatc accaaacatg ttgctggtga    4680
ttataatacc atttaggtgg gttgggttct taactaggat catggcggca gaatcaatca    4740
attgatgttg aaccttcaat gtagggaatt cgttcttgat ggtttcctcc acagtttttc    4800
tccataatct tgaagaggcc aaaagattag ctttatccaa ggaccaaata ggcaatggtg    4860
gctcatgttg tagggccatg aaagcggcca ttcttgtgat tctttgcact tctggaacgg    4920
tgtattgttc actatcccaa gcgacaccat caccatcgtc ttcctttctc ttaccaaagt    4980
aaatacctcc cactaattct ctgacaacaa cgaagtcagt acctttagca aattgtggct    5040
```

```
tgattggaga taagtctaaa agagagtcgg atgcaaagtt acatggtctt aagttggcgt      5100
acaattgaag ttctttacgg attttttagta aaccttgttc aggtctaaca ctaccggtac     5160
cccatttagg accagccaca gcacctaaca aaacggcatc aaccttcttg gaggcttcca      5220
gcgcctcatc tggaagtggg acacctgtag catcgatagc agcaccacca attaaatgat      5280
tttcgaaatc gaacttgaca ttggaacgaa catcagaaat agctttaaga accttaatgg      5340
cttcggctgt gatttcttga ccaacgtggt cacctggcaa aacgacgatc ttcttagggg      5400
cagacatagg ggcagacatt agaatggtat atccttgaaa tatatatata tattgctgaa      5460
atgtaaaagg taagaaaagt tagaaagtaa gacgattgct aaccacctat tggaaaaaac      5520
aataggtcct taaataatat tgtcaacttc aagtattgtg atgcaagcat ttagtcatga      5580
acgcttctct attctatatg aaaagccggt tccggcctct caccttttcct ttttctccca     5640 attttttcagt tgaaaaaggt atatgcgtca ggcgacctct gaaattaaca aaaaatttcc     5700
agtcatcgaa tttgattctg tgcgatagcg cccctgtgtg ttctcgttat gttgaggaaa      5760
aaaataatgg ttgctaagag attcgaactc ttgcatctta cgatacctga gtattcccac      5820
agttaactgc ggtcaagata tttcttgaat caggcgcctt agaccgctcg gccaaacaac      5880
caattacttg ttgagaaata gagtataatt atcctataaa tataacgttt ttgaacacac      5940
atgaacaagg aagtacagga caattgattt tgaagagaat gtggattttg atgtaattgt      6000
tgggattcca ttttttaataa ggcaataata ttaggtatgt ggatatacta gaagttctcc      6060
tcgaccgtcg atatgcggtg tgaaataccg cacagatgcg taaggagaaa ataccgcatc      6120
aggaaattgt aaacgttaat attttgttaa aattcgcgtt aaattttgt taaatcagct       6180 catttttta a ccaataggcc gaaatcggca aaatccctta taaatcaaaa gaatagaccg      6240 agataggggtt gagtgttgtt ccagtttgga acaagagtcc actattaaag aacgtggact     6300
ccaacgtcaa agggcgaaaa accgtctatc agggcgatgg cccactacgt gaaccatcac      6360
cctaatcaag tttttgggg tcgaggtgcc gtaaagcact aaatcggaac cctaaaggga       6420 gccccccgatt tagagcttga cggggaaagc cggcgaacgt ggcgagaaag gaagggaaga     6480
aagcgaaagg agcgggcgct agggcgctgg caagtgtagc ggtcacgctg cgcgtaacca     6540
ccacacccgc cgcgcttaat gcgccgctac agggcgcgtc gcgccattcg ccattcaggc     6600
tgcgcaactg ttgggaaggg cgatcggtgc gggcctcttc gctattacgc cagctggcga     6660 aaggggggatg tgctgcaagg cgattaagtt gggtaacgcc agggttttcc cagtcacgac     6720
gttgtaaaac gacggccagt gagcgcgcgt aatacgactc actatagggc gaattgggta     6780
ccgggccccc cctcgaggtc gacggtatcg ataagcttga tatcgaattc ctgcagcccg     6840
ggggatccgc atgcttgcat ttagtcgtgc aatgtatgac tttaagattt gtgagcagga     6900
agaaaaggga gaatcttcta acgataaacc cttgaaaaac tgggtagact acgctatgtt     6960
gagttgctac gcaggctgca caattacacg agaatgctcc cgcctaggat ttaaggctaa     7020
gggacgtgca atgcagacga cagatctaaa tgaccgtgtc ggtgaagtgt tcgccaaact     7080
tttcggttaa cacatgcagt gatgcacgcg cgatggtgct aagttacata tatatatata     7140
tatatatata tagccatagt gatgtctaag taacctttat ggtatatttc ttaatgtgga     7200
aagatactag cgcgcgcacc cacacacaag cttcgtcttt tcttgaagaa aagaggaagc     7260
tcgctaaatg ggattccact ttccgttccc tgccagctga tggaaaaagg ttagtggaac     7320
gatgaagaat aaaagagag atccactgag gtgaaatttc agctgacagc gagtttcatg     7380
atcgtgatga acaatggtaa cgagttgtgg ctgttgccag ggagggtggt tctcaacttt     7440
```

```
taatgtatgg ccaaatcgct acttgggttt gttatataac aaagaagaaa taatgaactg    7500
attctcttcc tccttcttgt cctttcttaa ttctgttgta attaccttcc tttgtaattt    7560
tttttgtaat tattcttctt aataatccaa acaaacacac atattacaat agctagctga    7620
ggatgaaggc attagtttat catggggatc acaaatttc gttagaagac aaaccaaaac     7680
ccactctgca gaaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaagggg     7860 ataaagtttt aatctcctgc gttactagct gtggatcgtg tgattattgc agaagcaac     7920 tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tatacccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactaccca atgttgatga     8520 aggtagcctc tactgataaa ttgcctttaa agaaaatgat tactcacagg tttgagttag    8580
ctgaaatcga acacgcatat caggttttct tgaatggcgc taagaaaaa gctatgaaga     8640 ttattctatc taatgcaggt gccgcctaat taattaagag taagcgaatt tcttatgatt    8700
tatgattttt attattaaat aagttataaa aaaataagt gtatacaaat tttaagtga      8760 ctcttaggtt ttaaaacgaa aattcttatt cttgagtaac tctttcctgt aggtcaggtt    8820
gctttctcag gtatagcatg aggtcgctct tattgaccac acctctaccg gcatgccgag    8880
caaatgcctg caaatcgctc cccatttcac ccaattgtag atatgctaac tccagcaatg    8940
agttgatgaa tctcggtgtg tattttatgt cctcagagga caacacctgt ggta         8994
```

<210> SEQ ID NO 79
<211> LENGTH: 2145
<212> TYPE: DNA
<213> ORGANISM: Artificial Sequence
<220> FEATURE:
<223> OTHER INFORMATION: constructed chimeric gene

<400> SEQUENCE: 79

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatatatata    300
tatagccata gtgatgtcta agtaaccttt atggtatatt tcttaatgtg gaaagatact     360
agcgcgcgca cccacacaca agcttcgtct tttcttgaag aaaagaggaa gctcgctaaa     420
tgggattcca ctttccgttc cctgccagct gatggaaaaa ggttagtgga acgatgaaga     480
```

| | |
|---|---|
| ataaaaagag agatccactg aggtgaaatt tcagctgaca gcgagtttca tgatcgtgat | 540 |
| gaacaatggt aacgagttgt ggctgttgcc agggagggtg gttctcaact tttaatgtat | 600 |
| ggccaaatcg ctacttgggt tgttatata acaaagaaga ataatgaac tgattctctt | 660 |
| cctccttctt gtcctttctt aattctgttg taattacctt cctttgtaat ttttttttgta | 720 |
| attattcttc ttaataatcc aaacaaacac acatattaca atagctagct gaggatgaag | 780 |
| gcattagttt atcatgggga tcacaaaatt tcgttagaag acaaaccaaa acccactctg | 840 |
| cagaaaccaa cagacgttgt ggttagggtg ttgaaaacaa caatttgcgg tactgacttg | 900 |
| ggaatataca aaggtaagaa tcctgaagtg cagatggca gaatcctggg tcatgagggc | 960 |
| gttggcgtca ttgaagaagt gggcgaatcc gtgacacaat tcaaaagggg ggataaagtt | 1020 |
| ttaatctcct gcgttactag ctgtggatcg tgtgattatt gcaagaagca actgtattca | 1080 |
| cactgtagag acggtggctg gattttaggt tacatgatcg acggtgtcca agccgaatac | 1140 |
| gtcagaatac cacatgctga caattcattg tataagatcc cgcaaactat cgatgatgaa | 1200 |
| attgcagtac tactgtccga tatttacct actggacatg aaattggtgt tcaatatggt | 1260 |
| aacgttcaac caggcgatgc tgtagcaatt gtaggagcag gtcctgttgg aatgtcagtt | 1320 |
| ttgttaactg ctcaatttta ctcgcctagt accattattg ttatcgacat ggacgaaaac | 1380 |
| cgtttacaat tagcgaagga gcttgggggcc acacacacta ttaactccgg tactgaaaat | 1440 |
| gttgtcgaag ctgtgcatcg tatagcagcc gaaggagtgg atgtagcaat agaagctgtt | 1500 |
| ggtatacccg caacctggga catctgtcag gaaattgtaa acccggcgc tcatattgcc | 1560 |
| aacgtgggag ttcatggtgt taaggtggac tttgaaattc aaaagttgtg gattaagaat | 1620 |
| ctaaccatca ccactggttt ggttaacact aatactaccc caatgttgat gaaggtagcc | 1680 |
| tctactgata aattgccttt aaagaaaatg attactcaca ggtttgagtt agctgaaatc | 1740 |
| gaacacgcat atcaggtttt cttgaatggc gctaaagaaa aagctatgaa gattattcta | 1800 |
| tctaatgcag gtgccgccta attaattaag agtaagcgaa tttcttatga tttatgattt | 1860 |
| ttattattaa ataagttata aaaaaaataa gtgtatacaa attttaaagt gactcttagg | 1920 |
| ttttaaaacg aaaattctta ttcttgagta actctttcct gtaggtcagg ttgctttctc | 1980 |
| aggtatagca tgaggtcgct cttattgacc acacctctac cggcatgccg agcaaatgcc | 2040 |
| tgcaaatcgc tccccatttc acccaattgt agatatgcta actccagcaa tgagttgatg | 2100 |
| aatctcggtg tgtattttat gtcctcagag gacaacacct gtggt | 2145 |

<210> SEQ ID NO 80
<211> LENGTH: 4280
<212> TYPE: DNA
<213> ORGANISM: Artificial Sequence
<220> FEATURE:
<223> OTHER INFORMATION: vector

<400> SEQUENCE: 80

| | |
|---|---|
| ggggatcctc tagagtcgac ctgcaggcat gcaagcttgg cgtaatcatg gtcatagctg | 60 |
| tttcctgtgt gaaattgtta tccgctcaca attccacaca acatacgagc cggaagcata | 120 |
| aagtgtaaag cctggggtgc ctaatgagtg agctaactca cattaattgc gttgcgctca | 180 |
| ctgcccgctt tccagtcggg aaacctgtcg tgccagctgc attaatgaat cggccaacgc | 240 |
| gcggggagag gcggttttgcg tattgggcgc tcttccgctt cctcgctcac tgactcgctg | 300 |
| cgctcggtcg ttcggctgcg gcgagcggta tcagctcact caaaggcggt aatacggtta | 360 |
| tccacagaat caggggataa cgcaggaaag aacatgtgag caaaaggcca gcaaaaggcc | 420 |

```
aggaaccgta aaaaggccgc gttgctggcg ttttttccata ggctccgccc ccctgacgag    480
catcacaaaa atcgacgctc aagtcagagg tggcgaaacc cgacaggact ataaagatac    540
caggcgtttc ccctggaag ctccctcgtg cgctctcctg ttccgaccct gccgcttacc     600
ggatacctgt ccgcctttct cccttcggga agcgtggcgc tttctcatag ctcacgctgt    660
aggtatctca gttcggtgta ggtcgttcgc tccaagctgg gctgtgtgca cgaaccccc    720 gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggttttttg tttgcaagca gcagattacg    1020
cgcagaaaaa aaggatctca agaagatcct ttgatctttt ctacggggtc tgacgctcag    1080
tggaacgaaa actcacgtta agggattttg gtcatgagat tatcaaaaag gatcttcacc    1140
tagatccttt taaattaaaa atgaagtttt aaatcaatct aaagtatata tgagtaaact    1200
tggtctgaca gttaccaatg cttaatcagt gaggcaccta tctcagcgat ctgtctattt    1260
cgttcatcca tagttgcctg actccccgtc gtgtagataa ctacgatacg ggagggctta    1320
ccatctggcc ccagtgctgc aatgataccg cgagacccac gctcaccggc tccagattta    1380
tcagcaataa accagccagc cggaagggcc gagcgcagaa gtggtcctgc aactttatcc    1440
gcctccatcc agtctattaa ttgttgccgg gaagctagag taagtagttc gccagttaat    1500
agtttgcgca acgttgttgc cattgctaca ggcatcgtgg tgtcacgctc gtcgtttggt    1560
atggcttcat tcagctccgg ttcccaacga tcaaggcgag ttacatgatc ccccatgttg    1620
tgcaaaaaag cggttagctc cttcggtcct ccgatcgttg tcagaagtaa gttggccgca    1680
gtgttatcac tcatggttat ggcagcactg cataattctc ttactgtcat gccatccgta    1740
agatgctttt ctgtgactgg tgagtactca accaagtcat tctgagaata gtgtatgcgg    1800
cgaccgagtt gctcttgccc ggcgtcaata cgggataata ccgcgccaca tagcagaact    1860
ttaaaagtgc tcatcattgg aaaacgttct tcggggcgaa aactctcaag atcttaccg    1920 ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040 ataaggcga cacggaaatg ttgaatactc atactcttcc ttttttcaata ttattgaagc    2100 atttatcagg gttattgtct catgagcgga tacatatttg aatgtattta gaaaataaa    2160 caaatagggg ttccgcgcac atttccccga aaagtgccac ctgacgtcta agaaaccatt    2220
attatcatga cattaaccta taaaaatagg cgtatcacga ggccctttcg tctcgcgcgt    2280
ttcggtgatg acggtgaaaa cctctgacac atgcagctcc cggagacggt cacagcttgt    2340
ctgtaagcga tgccgggag cagacaagcc cgtcagggcg cgtcagcggg tgttggcggg    2400
tgtcggggct ggcttaacta tgcggcatca gagcagattg tactgagagt gcaccatatg    2460
cggtgtgaaa taccgcacag atgcgtaagg agaaaatacc gcatcaggcg ccattcgcca    2520
ttcaggctgc gcaactgttg ggaagggcga tcggtgcggg cctcttcgct attacgccag    2580
ctggcgaaag ggggatgtgc tgcaaggcga ttaagttggg taacgccagg gttttcccag    2640
tcacgacgtt gtaaaacgac ggccagtgaa ttcgagctcg gtaccccgg ctctgagaca    2700 gtagtaggtt agtcatcgct ctaccgacgc gcaggaaaag aaagaagcat tgcggattac    2760
```

```
gtattctaat gttcagcccg cggaacgcca gcaaatcacc acccatgcgc atgatactga   2820
gtcttgtaca cgctgggctt ccagtgtact gagagtgcac cataccacag cttttcaatt   2880
caattcatca ttttttttt attctttttt ttgatttcgg tttctttgaa attttttga    2940 ttcggtaatc tccgaacaga aggaagaacg aaggaaggag cacagactta gattggtata   3000
tatacgcata tgtagtgttg aagaaacatg aaattgccca gtattcttaa cccaactgca   3060
cagaacaaaa acctgcagga aacgaagata aatcatgtcg aaagctacat ataaggaacg   3120
tgctgctact catcctagtc ctgttgctgc caagctattt aatatcatgc acgaaaagca   3180
aacaaacttg tgtgcttcat tggatgttcg taccaccaag gaattactgg agttagttga   3240
agcattaggt cccaaaattt gtttactaaa aacacatgtg gatatcttga ctgattttc    3300 catggagggc acagttaagc cgctaaaggc attatccgcc aagtacaatt ttttactctt   3360
cgaagacaga aaatttgctg acattggtaa tacagtcaaa ttgcagtact ctgcgggtgt   3420
atacagaata gcagaatggg cagacattac gaatgcacac ggtgtggtgg gcccaggtat   3480
tgttagcggt ttgaagcagg cggcagaaga agtaacaaag gaacctagag gccttttgat   3540
gttagcagaa ttgtcatgca agggctccct atctactgga gaatatacta agggtactgt   3600
tgacattgcg aagagcgaca aagattttgt tatcggcttt attgctcaaa gagacatggg   3660
tggaagagat gaaggttacg attggttgat tatgacaccc ggtgtgggtt tagatgacaa   3720
gggagacgca ttgggtcaac agtatagaac cgtggatgat gtggtctcta caggatctga   3780
cattattatt gttggaagag gactatttgc aaagggaagg gatgctaagg tagagggtga   3840
acgttacaga aaagcaggct gggaagcata tttgagaaga tgcggccagc aaaactaaaa   3900
aactgtatta taagtaaatg catgtatact aaactcacaa attagagctt caatttaatt   3960
atatcagtta ttaccctatg cggtgtgaaa taccgcacag atgcgtaagg agaaaatacc   4020
gcatcaggaa attgtaaacg ttaatatttt gttaaaattc gcgttaaatt tttgttaaat   4080
cagctcattt tttaaccaat aggccgaaat cggcaaaatc ttcagcccgc ggaacgccag   4140
caaatcacca cccatgcgca tgatactgag tcttgtacac gctgggcttc cagtgatgat   4200
acaacgagtt agccaaggtg agcacggatg tctaaattag aattacgttt taatatcttt   4260
ttttccatat ctagggctag                                              4280
```

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81

```
gcatgcttgc atttagtcgt gcaatgtatg                                     30
```

<210> SEQ ID NO 82
<211> LENGTH: 54
<212> TYPE: DNA
<213> ORGANISM: Artificial Sequence
<220> FEATURE:
<223> OTHER INFORMATION: primer

<400> SEQUENCE: 82

```
gaacattaga atacgtaatc cgcaatgcac tagtaccaca ggtgttgtcc tctg          54
```

<210> SEQ ID NO 83
<211> LENGTH: 54

```
<212> TYPE: DNA
<213> ORGANISM: Artificial Sequence
<220> FEATURE:
<223> OTHER INFORMATION: primer

<400> SEQUENCE: 83
cagaggacaa cacctgtggt actagtgcat tgcggattac gtattctaat gttc        54

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
caccttggct aactcgttgt atcatcac                                     28

<210> SEQ ID NO 85
<211> LENGTH: 100
<212> TYPE: DNA
<213> ORGANISM: Artificial Sequence
<220> FEATURE:
<223> OTHER INFORMATION: primer

<400> SEQUENCE: 85
ttttaagccg aatgagtgac agaaaaagcc cacaacttat caagtgatat tgaacaaagg  60
gcgaaacttc gcatgcttgc atttagtcgt gcaatgtatg                       100

<210> SEQ ID NO 86
<211> LENGTH: 98
<212> TYPE: DNA
<213> ORGANISM: Artificial Sequence
<220> FEATURE:
<223> OTHER INFORMATION: primer

<400> SEQUENCE: 86
cccaattggt aaatattcaa caagagacgc gcagtacgta acatgcgaat tgcgtaattc  60
acggcgataa caccttggct aactcgttgt atcatcac                          98

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
caaaagccca tgtcccacac caaaggatg                                    29

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
caccatcgcg cgtgcatcac tgcatg                                       26

<210> SEQ ID NO 89
<211> LENGTH: 28
<212> TYPE: DNA
<213> ORGANISM: Artificial Sequence
<220> FEATURE:
```

<223> OTHER INFORMATION: primer

<400> SEQUENCE: 89
tcggtttttg caatatgacc tgtgggcc　　　　　　　　　　　　　　　　　　　28

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
gagaagatgc ggccagcaaa ac　　　　　　　　　　　　　　　　　　　　　22

<210> SEQ ID NO 91
<211> LENGTH: 2745
<212> TYPE: DNA
<213> ORGANISM: Artificial Sequence
<220> FEATURE:
<223> OTHER INFORMATION: constructed coding region-terminator segment

<400> SEQUENCE: 91

| | | | | |
|---|---|---|---|---|
| atgactgaca | aaaaaactct | taaagactta | agaaatcgta | gttctgttta cgattcaatg | 60 |
| gttaaatcac | ctaatcgtgc | tatgttgcgt | gcaactggta | tgcaagatga agactttgaa | 120 |
| aaacctatcg | tcggtgtcat | ttcaacttgg | gctgaaaaca | caccttgtaa tatccactta | 180 |
| catgactttg | gtaaactagc | caaagtcggt | gttaaggaag | ctggtgcttg ccagttcag | 240 |
| ttcggaacaa | tcacggtttc | tgatggaatc | gccatgggaa | cccaaggaat gcgtttctcc | 300 |
| ttgacatctc | gtgatattat | tgcagattct | attgaagcag | ccatgggagg tcataatgcg | 360 |
| gatgcttttg | tagccattgg | cggttgtgat | aaaaacatgc | ccggttctgt tatcgctatg | 420 |
| gctaacatgg | atatcccagc | cattttttgct | tacggcggaa | caattgcacc tggtaattta | 480 |
| gacggcaaag | atatcgattt | agtctctgtc | tttgaaggtg | tcggccattg gaaccacggc | 540 |
| gatatgacca | agaagaagt | taaagctttg | gaatgtaatg | cttgtcccgg tcctggaggc | 600 |
| tgcggtggta | tgtatactgc | taacacaatg | gcgacagcta | ttgaagtttt gggacttagc | 660 |
| cttccgggtt | catcttctca | cccggctgaa | tccgcagaaa | agaaagcaga tattgaagaa | 720 |
| gctggtcgcg | ctgttgtcaa | aatgctcgaa | atgggcttaa | aaccttctga cattttaacg | 780 |
| cgtgaagctt | ttgaagatgc | tattactgta | actatggctc | tgggaggttc aaccaactca | 840 |
| acccttcacc | tcttagctat | tgcccatgct | gctaatgtgg | aattgacact tgatgatttc | 900 |
| aatactttcc | aagaaaagt | tcctcatttg | gctgatttga | aaccttctgg tcaatatgta | 960 |
| ttccaagacc | tttacaaggt | cggagggta | ccagcagtta | tgaaatatct ccttaaaaat | 1020 |
| ggcttccttc | atggtgaccg | tatcacttgt | actggcaaaa | cagtcgctga aaatttgaag | 1080 |
| gcttttgatg | atttaacacc | tggtcaaaag | gttattatgc | gcttgaaaaa tcctaaacgt | 1140 |
| gaagatggtc | cgctcattat | tctccatggt | aacttggctc | cagacggtgc cgttgccaaa | 1200 |
| gtttctggtg | taaaagtgcg | tcgtcatgtc | ggtcctgcta | aggtctttaa ttctgaagaa | 1260 |
| gaagccattg | aagctgtctt | gaatgatgat | attgttgatg | tgatgttgt tgtcgtacgt | 1320 |
| tttgtaggac | caagggcgg | tcctggtatg | cctgaaatgc | tttcccttc atcaatgatt | 1380 |
| gttggtaaag | ggcaaggtga | aaagttgcc | cttctgacag | atggccgctt ctcaggtggt | 1440 |
| acttatggtt | tgtcgtggg | tcatatcgct | cctgaagcac | aagatggcgg tccaatcgcc | 1500 |
| tacctgcaaa | caggagacat | agtcactatt | gaccaagaca | ctaaggaatt acactttgat | 1560 |

```
atctccgatg aagagttaaa acatcgtcaa gagaccattg aattgccacc gctctattca    1620
cgcggtatcc ttggtaaata tgctcacatc gtttcgtctg cttctagggg agccgtaaca    1680
gacttttgga agcctgaaga aactggcaaa aaatgttgtc ctggttgctg tggttaagcg    1740
gccgcgttaa ttcaaattaa ttgatatagt tttttaatga gtattgaatc tgtttagaaa    1800
taatggaata ttattttat ttatttattt atattattgg tcggctcttt tcttctgaag     1860
gtcaatgaca aaatgatatg aaggaaataa tgatttctaa aattttacaa cgtaagatat    1920
ttttacaaaa gcctagctca tcttttgtca tgcactattt tactcacgct tgaaattaac    1980
ggccagtcca ctgcggagtc atttcaaagt catcctaatc gatctatcgt ttttgatagc    2040
tcatttgga gttcgcgatt gtcttctgtt attcacaact gttttaattt ttatttcatt     2100
ctggaactct tcgagttctt tgtaaagtct ttcatagtag cttactttat cctccaacat    2160
atttaacttc atgtcaattt cggctcttaa attttccaca tcatcaagtt caacatcatc    2220
ttttaacttg aatttattct ctagctcttc caaccaagcc tcattgctcc ttgatttact    2280
ggtgaaaagt gatacacttt gcgcgcaatc caggtcaaaa cttcctgca aagaattcac     2340
caatttctcg acatcatagt acaatttgtt ttgttctccc atcacaattt aatatacctg    2400
atggattctt atgaagcgct gggtaatgga cgtgtcactc tacttcgcct ttttccctac    2460
tccttttagt acgaagaca atgctaataa ataagagggt aataataata ttattaatcg     2520
gcaaaaaga ttaaacgcca agcgtttaat tatcagaaag caaacgtcgt accaatcctt     2580
gaatgcttcc caattgtata ttaagagtca tcacagcaac atattcttgt tattaaatta    2640
attattattg attttgata ttgtataaaa aaaccaaata tgtataaaaa aagtgaataa     2700
aaaataccaa gtatggagaa atatattaga agtctatacg ttaaa                    2745
```

```
<210> SEQ ID NO 92
<211> LENGTH: 27
<212> TYPE: DNA
<213> ORGANISM: Artificial Sequence
<220> FEATURE:
<223> OTHER INFORMATION: primer

<400> SEQUENCE: 92
gacttttgga agcctgaaga aactggc                                         27

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
cttggcagca acaggactag                                                 20

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ccaggccaat tcaacagact gtcggc                                          26

<210> SEQ ID NO 95
```

<211> LENGTH: 2347
<212> TYPE: DNA
<213> ORGANISM: Artificial Sequence
<220> FEATURE:
<223> OTHER INFORMATION: constructed URA3 marker with flanking homologous repeat sequences for HIS gene replacement and marker excision

<400> SEQUENCE: 95

| | | | | | |
|---|---|---|---|---|---|
| gcattgcgga | ttacgtattc | taatgttcag | gtgctggaag | aagagctgct | taaccgccgc | 60 |
| gcccagggtg | aagatccacg | ctactttacc | ctgcgtcgtc | tggatttcgg | cggctgtcgt | 120 |
| ctttcgctgg | caacgccggt | tgatgaagcc | tgggacggtc | cgctctcctt | aaacggtaaa | 180 |
| cgtatcgcca | cctcttatcc | tcacctgctc | aagcgttatc | tcgaccagaa | aggcatctct | 240 |
| tttaaatcct | gcttactgaa | cggttctgtt | gaagtcgccc | cgcgtgccgg | actggcggat | 300 |
| gcgatttgcg | atctggtttc | caccggtgcc | acgctggaag | ctaacggcct | gcgcgaagtc | 360 |
| gaagttatct | atcgctcgaa | agcctgcctg | attcaacgcg | atggcgaaat | ggaagaatcc | 420 |
| aaacagcaac | tgatcgacaa | actgctgacc | cgtattcagg | gtgtgatcca | ggcgcgcgaa | 480 |
| tcaaaataca | tcatgatgca | cgcaccgacc | gaacgtctgg | atgaagtcat | ggtacctact | 540 |
| gagagtgcac | cataccacag | cttttcaatt | caattcatca | tttttttttt | attcttttt | 600 |
| ttgatttcgg | tttctttgaa | attttttga | ttcggtaatc | tccgaacaga | aggaagaacg | 660 |
| aaggaaggag | cacagactta | gattggtata | tatacgcata | tgtagtgttg | aagaaacatg | 720 |
| aaattgccca | gtattcttaa | cccaactgca | cagaacaaaa | acctgcagga | aacgaagata | 780 |
| aatcatgtcg | aaagctacat | ataaggaacg | tgctgctact | catcctagtc | ctgttgctgc | 840 |
| caagctatt | aatatcatgc | acgaaaagca | aacaaacttg | tgtgcttcat | tggatgttcg | 900 |
| taccaccaag | gaattactgg | agttagttga | agcattaggt | cccaaaattt | gtttactaaa | 960 |
| aacacatgtg | gatatcttga | ctgattttc | catggagggc | acagttaagc | cgctaaaggc | 1020 |
| attatccgcc | aagtacaatt | ttttactctt | cgaagacaga | aaatttgctg | acattggtaa | 1080 |
| tacagtcaaa | ttgcagtact | ctgcgggtgt | atacagaata | gcagaatggg | cagacattac | 1140 |
| gaatgcacac | ggtgtggtgg | gcccaggtat | tgttagcggt | ttgaagcagg | cggcagaaga | 1200 |
| agtaacaaag | gaacctagag | gccttttgat | gttagcagaa | ttgtcatgca | agggctccct | 1260 |
| atctactgga | gaatatacta | agggtactgt | tgacattgcg | aagagcgaca | aagattttgt | 1320 |
| tatcggcttt | attgctcaaa | gagacatggg | tggaagagat | gaaggttacg | attggttgat | 1380 |
| tatgacaccc | ggtgtgggtt | tagatgacaa | gggagacgca | ttgggtcaac | agtatagaac | 1440 |
| cgtggatgat | gtggtctcta | caggatctga | cattattatt | gttggaagag | gactatttgc | 1500 |
| aaagggaagg | gatgctaagg | tagagggtga | acgttacaga | aaagcaggct | gggaagcata | 1560 |
| tttgagaaga | tgcggccagc | aaaactaaaa | aactgtatta | taagtaaatg | catgtatact | 1620 |
| aaactcacaa | attagagctt | caatttaatt | atatcagtta | ttaccctatg | cggtgtgaaa | 1680 |
| taccgcacag | atgcgtaagg | agaaaatacc | gcatcaggaa | attgtaaacg | ttaatatttt | 1740 |
| gttaaaattc | gcgttaaatt | tttgttaaat | cagctcattt | tttaaccaat | aggccgaaat | 1800 |
| cggcaaaatc | tctagagtgc | tggaagaaga | gctgcttaac | cgccgcgccc | agggtgaaga | 1860 |
| tccacgctac | tttaccctgc | gtcgtctgga | tttcggcggc | tgtcgtcttt | cgctggcaac | 1920 |
| gccggttgat | gaagcctggg | acggtccgct | ctccttaaac | ggtaaacgta | tcgccacctc | 1980 |
| ttatcctcac | ctgctcaagc | gttatctcga | ccagaaaggc | atctctttta | aatcctgctt | 2040 |
| actgaacggt | tctgttgaag | tcgccccgcg | tgccggactg | gcggatgcga | tttgcgatct | 2100 |

```
ggtttccacc ggtgccacgc tggaagctaa cggcctgcgc gaagtcgaag ttatctatcg    2160
ctcgaaagcc tgcctgattc aacgcgatgg cgaaatggaa gaatccaaac agcaactgat    2220
cgacaaactg ctgacccgta ttcagggtgt gatccaggcg cgcgaatcaa aatacatcat    2280
gatgcacgca ccgaccgaac gtctggatga agtcatccag tgatgataca acgagttagc    2340
caaggtg                                                              2347

<210> SEQ ID NO 96
<211> LENGTH: 80
<212> TYPE: DNA
<213> ORGANISM: Artificial Sequence
<220> FEATURE:
<223> OTHER INFORMATION: primer

<400> SEQUENCE: 96
cttcgaagaa tatactaaaa aatgagcagg caagataaac gaaggcaaag gcattgcgga    60
ttacgtattc taatgttcag                                                80

<210> SEQ ID NO 97
<211> LENGTH: 80
<212> TYPE: DNA
<213> ORGANISM: Artificial Sequence
<220> FEATURE:
<223> OTHER INFORMATION: primer

<400> SEQUENCE: 97
cttcgaagaa tatactaaaa aatgagcagg caagataaac gaaggcaaag gcattgcgga    60
ttacgtattc taatgttcag                                                80

<210> SEQ ID NO 98
<211> LENGTH: 26
<212> TYPE: DNA
<213> ORGANISM: Artificial Sequence
<220> FEATURE:
<223> OTHER INFORMATION: primer

<400> SEQUENCE: 98
gacttgaata atgcagcggc gcttgc                                         26

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ccaccctctt caattagcta agatcatagc                                     30

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
aaaaattgat tctcatcgta aatgc                                          25

<210> SEQ ID NO 101
<211> LENGTH: 20
<212> TYPE: DNA
```

<213> ORGANISM: Artificial Sequence
<220> FEATURE:
<223> OTHER INFORMATION: primer

<400> SEQUENCE: 101
ctgcagcgag gagccgtaat                                                  20

<210> SEQ ID NO 102
<211> LENGTH: 90
<212> TYPE: DNA
<213> ORGANISM: Artificial Sequence
<220> FEATURE:
<223> OTHER INFORMATION: primer

<400> SEQUENCE: 102
atggttcatt taggtccaaa aaaaccacaa gccagaaagg gttccatggc cgatgtgcca      60
gcattgcgga ttacgtattc taatgttcag                                      90

<210> SEQ ID NO 103
<211> LENGTH: 91
<212> TYPE: DNA
<213> ORGANISM: Artificial Sequence
<220> FEATURE:
<223> OTHER INFORMATION: primer

<400> SEQUENCE: 103
ttaagcaccg atgataccaa cggacttacc ttcagcaatt cttttttggg ccaaagcagc      60
caccttggct aactcgttgt atcatcactg g                                    91

<210> SEQ ID NO 104
<211> LENGTH: 24
<212> TYPE: DNA
<213> ORGANISM: Artificial Sequence
<220> FEATURE:
<223> OTHER INFORMATION: primer

<400> SEQUENCE: 104
ctaggatgag tagcagcacg ttcc                                             24

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ccaattccgt gatgtctctt tgttgc                                           26

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gtgaacgagt tcacaaccgc                                                  20

<210> SEQ ID NO 107
<211> LENGTH: 22
<212> TYPE: DNA
<213> ORGANISM: Artificial Sequence
<220> FEATURE:
<223> OTHER INFORMATION: primer

```
<400> SEQUENCE: 107
gttcgttcca gaattatcac gc                                                  22

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
ggatccgcat gcttgcattt agtcgtgc                                            28

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gggatgcgga cgtattcggc                                                     20

<210> SEQ ID NO 110
<211> LENGTH: 99
<212> TYPE: DNA
<213> ORGANISM: Artificial Sequence
<220> FEATURE:
<223> OTHER INFORMATION: primer

<400> SEQUENCE: 110
tcctttctca attattattt tctactcata acctcacgca aaataacaca gtcaaatcaa         60
tcaaagtatg actgacaaaa aaactcttaa agacttaag                                99

<210> SEQ ID NO 111
<211> LENGTH: 77
<212> TYPE: DNA
<213> ORGANISM: Artificial Sequence
<220> FEATURE:
<223> OTHER INFORMATION: primer

<400> SEQUENCE: 111
gaacattaga atacgtaatc cgcaatgctt ctttcttttc cgtttaacgt atagacttct         60
aatatatttc tccatac                                                        77

<210> SEQ ID NO 112
<211> LENGTH: 45
<212> TYPE: DNA
<213> ORGANISM: Artificial Sequence
<220> FEATURE:
<223> OTHER INFORMATION: primer

<400> SEQUENCE: 112
aaacggaaaa gaaagaagca ttgcggatta cgtattctaa tgttc                         45

<210> SEQ ID NO 113
<211> LENGTH: 88
<212> TYPE: DNA
<213> ORGANISM: Artificial Sequence
<220> FEATURE:
<223> OTHER INFORMATION: primer

<400> SEQUENCE: 113
```

```
tattttttcgt tacataaaaa tgcttataaa actttaacta ataattagag attaaatcgc      60
caccttggct aactcgttgt atcatcac                                          88

<210> SEQ ID NO 114
<211> LENGTH: 1713
<212> TYPE: DNA
<213> ORGANISM: Streptococcus mutans

<400> SEQUENCE: 114
atgactgaca aaaaaactct aaagactta agaaatcgta gttctgttta cgattcaatg        60
gttaaatcac ctaatcgtgc tatgttgcgt gcaactggta tgcaagatga agactttgaa      120
aaacctatcg tcggtgtcat ttcaacttgg gctgaaaaca caccttgtaa tatccactta      180
catgactttg gtaaactagc caaagtcggt gttaaggaag ctggtgcttg gccagttcag      240
ttcggaacaa tcacggtttc tgatggaatc gccatgggaa cccaaggaat gcgtttctcc      300
ttgcatctcc gtgatattat tgcagattct attgaagcag ccatgggagg tcataatgcg      360
gatgcttttg tagccattgg cggttgtgat aaaaacatgc ccggttctgt tatcgctatg      420
gctaacatgg atatcccagc catttttgct tacggcggaa caattgcacc tggtaattta      480
gacggcaaag atatcgattt agtctctgtc tttgaaggtg tcggccattg gaaccacggc      540
gatatgacca agaagaagt taaagctttg gaatgtaatg cttgtcccgg tcctggaggc      600
tgcggtggta tgtatactgc taacacaatg gcgacagcta ttgaagtttt gggacttagc      660
cttccgggtt catcttctca cccggctgaa tccgcagaaa agaaagcaga tattgaagaa      720
gctggtcgcg ctgttgtcaa atgctcgaa atgggcttaa accttctga cattttaacg       780 cgtgaagctt ttgaagatgc tattactgta actatggctc tgggaggttc aaccaactca      840
acccttcacc tcttagctat tgcccatgct gctaatgtgg aattgacact tgatgatttc      900
aatactttcc aagaaaaagt tcctcatttg gctgatttga accttctgg tcaatatgta       960 ttccaagacc tttacaaggt cggagggggta ccagcagtta tgaaatatct ccttaaaaat     1020
ggcttccttc atggtgaccg tatcacttgt actggcaaaa cagtcgctga aaatttgaag     1080
gcttttgatg atttaacacc tggtcaaaag gttattatgc cgcttgaaaa tcctaaacgt     1140
gaagatggtc cgctcattat tctccatggt aacttggctc cagacggtgc cgttgccaaa     1200
gtttctggtc taaaagtgcg tcgtcatgtc ggtcctgcta aggtctttaa ttctgaagaa     1260
gaagccattg aagctgtctt gaatgatgat attgttgatg gtgatgttgt tgtcgtacgt     1320
tttgtaggac caaagggcgg tcctggtatg cctgaaatgc tttcccttc atcaatgatt      1380 gttggtaaag ggcaaggtga aaaagttgcc cttctgacag atggccgctt ctcaggtggt     1440
acttatggtc ttgtcgtggg tcatatcgct cctgaagcac aagatggcgg tccaatcgcc     1500
tacctgcaaa caggagacat agtcactatt gaccaagaca ctaaggaatt acacttttgat     1560 atctccgatg aagagttaaa acatcgtcaa gagaccattg aattgccacc gctctattca     1620
cgcggtatcc ttggtaaata tgctcacatc gtttcgtctg cttctagggg agccgtaaca     1680
gacttttgga agcctgaaga aactggcaaa aaa                                   1713

<210> SEQ ID NO 115
<211> LENGTH: 571
<212> TYPE: PRT
<213> ORGANISM: Streptococcus mutans

<400> SEQUENCE: 115

Met Thr Asp Lys Lys Thr Leu Lys Asp Leu Arg Asn Arg Ser Ser Val
```

-continued

```
1               5                   10                  15
Tyr Asp Ser Met Val Lys Ser Pro Asn Arg Ala Met Leu Arg Ala Thr
            20                  25                  30
Gly Met Gln Asp Glu Asp Phe Glu Lys Pro Ile Val Gly Val Ile Ser
            35                  40                  45
Thr Trp Ala Glu Asn Thr Pro Cys Asn Ile His Leu His Asp Phe Gly
 50                  55                  60
Lys Leu Ala Lys Val Gly Val Lys Glu Ala Gly Ala Trp Pro Val Gln
 65                  70                  75                  80
Phe Gly Thr Ile Thr Val Ser Asp Gly Ile Ala Met Gly Thr Gln Gly
                85                  90                  95
Met Arg Phe Ser Leu Thr Ser Arg Asp Ile Ile Ala Asp Ser Ile Glu
                100                 105                 110
Ala Ala Met Gly Gly His Asn Ala Asp Ala Phe Val Ala Ile Gly Gly
                115                 120                 125
Cys Asp Lys Asn Met Pro Gly Ser Val Ile Ala Met Ala Asn Met Asp
    130                 135                 140
Ile Pro Ala Ile Phe Ala Tyr Gly Gly Thr Ile Ala Pro Gly Asn Leu
145                 150                 155                 160
Asp Gly Lys Asp Ile Asp Leu Val Ser Val Phe Glu Gly Val Gly His
                165                 170                 175
Trp Asn His Gly Asp Met Thr Lys Glu Glu Val Lys Ala Leu Glu Cys
                180                 185                 190
Asn Ala Cys Pro Gly Pro Gly Gly Cys Gly Gly Met Tyr Thr Ala Asn
                195                 200                 205
Thr Met Ala Thr Ala Ile Glu Val Leu Gly Leu Ser Leu Pro Gly Ser
    210                 215                 220
Ser Ser His Pro Ala Glu Ser Ala Glu Lys Lys Ala Asp Ile Glu Glu
225                 230                 235                 240
Ala Gly Arg Ala Val Val Lys Met Leu Glu Met Gly Leu Lys Pro Ser
                245                 250                 255
Asp Ile Leu Thr Arg Glu Ala Phe Glu Asp Ala Ile Thr Val Thr Met
                260                 265                 270
Ala Leu Gly Gly Ser Thr Asn Ser Thr Leu His Leu Leu Ala Ile Ala
                275                 280                 285
His Ala Ala Asn Val Glu Leu Thr Leu Asp Asp Phe Asn Thr Phe Gln
    290                 295                 300
Glu Lys Val Pro His Leu Ala Asp Leu Lys Pro Ser Gly Gln Tyr Val
305                 310                 315                 320
Phe Gln Asp Leu Tyr Lys Val Gly Gly Val Pro Ala Val Met Lys Tyr
                325                 330                 335
Leu Leu Lys Asn Gly Phe Leu His Gly Asp Arg Ile Thr Cys Thr Gly
                340                 345                 350
Lys Thr Val Ala Glu Asn Leu Lys Ala Phe Asp Asp Leu Thr Pro Gly
                355                 360                 365
Gln Lys Val Ile Met Pro Leu Glu Asn Pro Lys Arg Glu Asp Gly Pro
    370                 375                 380
Leu Ile Ile Leu His Gly Asn Leu Ala Pro Asp Gly Ala Val Ala Lys
385                 390                 395                 400
Val Ser Gly Val Lys Val Arg Arg His Val Gly Pro Ala Lys Val Phe
                405                 410                 415
Asn Ser Glu Glu Glu Ala Ile Glu Ala Val Leu Asn Asp Asp Ile Val
                420                 425                 430
```

```
Asp Gly Asp Val Val Val Arg Phe Val Gly Pro Lys Gly Gly Pro
        435                 440                 445

Gly Met Pro Glu Met Leu Ser Leu Ser Ser Met Ile Val Gly Lys Gly
        450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
                500                 505                 510

Asp Thr Lys Glu Leu His Phe Asp Ile Ser Asp Glu Leu Lys His
            515                 520                 525

Arg Gln Glu Thr Ile Glu Leu Pro Pro Leu Tyr Ser Arg Gly Ile Leu
        530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

<210> SEQ ID NO 116
<211> LENGTH: 548
<212> TYPE: PRT
<213> ORGANISM: Lactococcus lactis

<400> SEQUENCE: 116

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
```

```
                    225                 230                 235                 240

Phe Gly Lys Ser Ser Val Asp Glu Ala Leu Pro Ser Phe Leu Gly Ile
                        245                 250                 255

Tyr Asn Gly Thr Leu Ser Glu Pro Asn Leu Lys Glu Phe Val Glu Ser
                        260                 265                 270

Ala Asp Phe Ile Leu Met Leu Gly Val Lys Leu Thr Asp Ser Ser Thr
                        275                 280                 285

Gly Ala Phe Thr His His Leu Asn Glu Asn Lys Met Ile Ser Leu Asn
                        290                 295                 300

Ile Asp Glu Gly Lys Ile Phe Asn Glu Arg Ile Gln Asn Phe Asp Phe
        305                 310                 315                 320

Glu Ser Leu Ile Ser Ser Leu Asp Leu Ser Glu Ile Glu Tyr Lys
                        325                 330                 335

Gly Lys Tyr Ile Asp Lys Lys Gln Glu Asp Phe Val Pro Ser Asn Ala
                        340                 345                 350

Leu Leu Ser Gln Asp Arg Leu Trp Gln Ala Val Glu Asn Leu Thr Gln
                        355                 360                 365

Ser Asn Glu Thr Ile Val Ala Glu Gln Gly Thr Ser Phe Phe Gly Ala
                        370                 375                 380

Ser Ser Ile Phe Leu Lys Ser Lys Ser His Phe Ile Gly Gln Pro Leu
        385                 390                 395                 400

Trp Gly Ser Ile Gly Tyr Thr Phe Pro Ala Ala Leu Gly Ser Gln Ile
                        405                 410                 415

Ala Asp Lys Glu Ser Arg His Leu Leu Phe Ile Gly Asp Gly Ser Leu
                        420                 425                 430

Gln Leu Thr Val Gln Glu Leu Gly Leu Ala Ile Arg Glu Lys Ile Asn
                        435                 440                 445

Pro Ile Cys Phe Ile Ile Asn Asn Asp Gly Tyr Thr Val Glu Arg Glu
                        450                 455                 460

Ile His Gly Pro Asn Gln Ser Tyr Asn Asp Ile Pro Met Trp Asn Tyr
        465                 470                 475                 480

Ser Lys Leu Pro Glu Ser Phe Gly Ala Thr Glu Asp Arg Val Val Ser
                        485                 490                 495

Lys Ile Val Arg Thr Glu Asn Glu Phe Val Ser Val Met Lys Glu Ala
                        500                 505                 510

Gln Ala Asp Pro Asn Arg Met Tyr Trp Ile Glu Leu Ile Leu Ala Lys
                        515                 520                 525

Glu Gly Ala Pro Lys Val Leu Lys Lys Met Gly Lys Leu Phe Ala Glu
                        530                 535                 540

Gln Asn Lys Ser
        545

<210> SEQ ID NO 117
<211> LENGTH: 1125
<212> TYPE: DNA
<213> ORGANISM: Artificial Sequence
<220> FEATURE:
<223> OTHER INFORMATION: horse ADH coding region codon optimized for S.
      cerevisiae expression

<400> SEQUENCE: 117
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
```

```
ccttttgccag taatcgcgggg acacgaggct gccggaatcg ttgaatccat aggtgaaggt    240
gttaccactg ttcgtcctgg tgataaagtg atcccactgt tcactcctca atgtggtaag    300
tgtagagtct gcaaacatcc tgagggtaat ttctgcctta aaaatgattt gtctatgcct    360
agaggtacta tgcaggatgg tacaagcaga tttacatgca gagggaaacc tatacaccat    420
ttccttggta cttctacatt tcccaatac acagtggtgg acgagatatc tgtcgctaaa    480
atcgatgcag cttcaccact ggaaaaagtt tgcttgatag ggtgcggatt ttccaccggt    540
tacggttccg cagttaaagt tgcaaaggtt acacagggtt cgacttgtgc agtattcggt    600
ttaggaggag taggactaag cgttattatg gggtgtaaag ctgcaggcgc agcgaggatt    660
ataggtgtag acatcaataa ggacaaattt gcaaaagcta aggaggtcgg ggctactgaa    720
tgtgttaacc ctcaagatta taagaaacca atacaagaag tccttactga aatgtcaaac    780
ggtggagttg atttctcttt tgaagttata ggccgtcttg atactatggt aactgcgttg    840
tcctgctgtc aagaggcata tggagtcagt gtgatcgtag tgttcctcc tgattcacaa    900 aatttgtcga tgaatcctat gctgttgcta agcggtcgta catggaaggg agctatattt    960
ggcggtttta agagcaagga tagtgttcca aaacttgttg ccgactttat ggcgaagaag   1020
tttgctcttg atcctttaat tacacatgta ttgccattcg agaaaatcaa tgaagggttt   1080
gatttgttaa gaagtggtga atctattcgt acaattttaa cttt                    1125
```

<210> SEQ ID NO 118
<211> LENGTH: 375
<212> TYPE: PRT
<213> ORGANISM: Equus caballus

<400> SEQUENCE: 118

```
Met Ser Thr Ala Gly Lys Val Ile Lys Cys Lys Ala Ala Val Leu Trp
1               5                   10                  15

Glu Glu Lys Lys Pro Phe Ser Ile Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205
```

Ile Met Gly Cys Lys Ala Ala Gly Ala Ala Arg Ile Ile Gly Val Asp
    210                 215                 220
Ile Asn Lys Asp Lys Phe Ala Lys Ala Lys Glu Val Gly Ala Thr Glu
225                 230                 235                 240
Cys Val Asn Pro Gln Asp Tyr Lys Lys Pro Ile Gln Glu Val Leu Thr
                245                 250                 255
Glu Met Ser Asn Gly Gly Val Asp Phe Ser Phe Glu Val Ile Gly Arg
            260                 265                 270
Leu Asp Thr Met Val Thr Ala Leu Ser Cys Cys Gln Glu Ala Tyr Gly
        275                 280                 285
Val Ser Val Ile Val Gly Val Pro Pro Asp Ser Gln Asn Leu Ser Met
    290                 295                 300
Asn Pro Met Leu Leu Leu Ser Gly Arg Thr Trp Lys Gly Ala Ile Phe
305                 310                 315                 320
Gly Gly Phe Lys Ser Lys Asp Ser Val Pro Lys Leu Val Ala Asp Phe
                325                 330                 335
Met Ala Lys Lys Phe Ala Leu Asp Pro Leu Ile Thr His Val Leu Pro
            340                 345                 350
Phe Glu Lys Ile Asn Glu Gly Phe Asp Leu Leu Arg Ser Gly Glu Ser
        355                 360                 365
Ile Arg Thr Ile Leu Thr Phe
    370                 375

<210> SEQ ID NO 119
<211> LENGTH: 643
<212> TYPE: DNA
<213> ORGANISM: Saccharomyces cerevisiae

<400> SEQUENCE: 119
gaaatgaata acaatactga cagtactaaa taattgccta cttggcttca catacgttgc        60
atacgtcgat atagataata atgataatga cagcaggatt atcgtaatac gtaatagttg       120
aaaatctcaa aaatgtgtgg gtcattacgt aaataatgat aggaatggga ttcttctatt       180 tttcctttt ccattctagc agccgtcggg aaaacgtggc atcctctctt tcgggctcaa        240
ttggagtcac gctgccgtga gcatcctctc tttccatatc taacaactga gcacgtaacc       300
aatggaaaag catgagctta gcgttgctcc aaaaaagtat tggatggtta ataccatttg       360
tctgttctct tctgactttg actcctcaaa aaaaaaaat ctacaatcaa cagatcgctt        420
caattacgcc ctcacaaaaa cttttttcct tcttcttcgc ccacgttaaa ttttatccct       480
catgttgtct aacggatttc tgcacttgat ttattataaa aagacaaaga cataatactt       540
ctctatcaat ttcagttatt gttcttcctt gcgttattct tctgttcttc ttttcttt         600 gtcatatata accataacca agtaatacat attcaaatct aga                        643

<210> SEQ ID NO 120
<211> LENGTH: 9089
<212> TYPE: DNA
<213> ORGANISM: Artificial Sequence
<220> FEATURE:
<223> OTHER INFORMATION: constructed plasmid

<400> SEQUENCE: 120
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180

```
accataccac agcttttcaa ttcaattcat cattttttt ttattcttt ttttgatttc      240 ggtttctttg aaattttttt gattcggtaa tctccgaaca gaaggaagaa cgaaggaagg      300
agcacagact tagattggta tatatacgca tatgtagtgt tgaagaaaca tgaaattgcc      360
cagtattctt aacccaactg cacagaacaa aaacctgcag gaaacgaaga taaatcatgt      420
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat ttgtttacta aaaacacatg      600
tggatatctt gactgatttt tccatggagg gcacagttaa gccgctaaag gcattatccg      660
ccaagtacaa ttttttactc ttcgaagaca gaaaatttgc tgacattggt aatacagtca      720
aattgcagta ctctgcgggt gtatacgaaa tagcagaatg gcagacatt acgaatgcac      780 acggtgtggt gggcccaggt attgttagcg gttttgaagca ggcggcagaa gaagtaacaa      840
aggaacctag aggcctttttg atgttagcag aattgtcatg caagggctcc ctatctactg      900
gagaatatac taagggtact gttgacattg cgaagagcga caaagatttt gttatcggct      960
ttattgctca aagagacatg ggtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttggaag aggactattt gcaagggaa      1140 gggatgctaa ggtagagggt gaacgttaca gaaaagcagg ctgggaagca tatttgaaga     1200
gatgcggcca gcaaaactaa aaaactgtat tataagtaaa tgcatgtata ctaaactcac     1260
aaattagagc ttcaatttaa ttatatcagt tattaccccta tgcggtgtga ataccgcac      1320 agatgcgtaa ggagaaaata ccgcatcagg aaattgtaaa cgttaatatt ttgttaaaat     1380
tcgcgttaaa ttttttgttaa atcagctcat tttttaacca ataggccgaa atcggcaaaa     1440
tcccttataa atcaaaagaa tagaccgaga tagggttgag tgttgttcca gtttggaaca     1500
agagtccact attaaagaac gtggactcca acgtcaaagg gcgaaaaacc gtctatcagg     1560
gcgatggccc actacgtgaa ccatcaccct aatcaagttt tttggggtcg aggtgccgta     1620
aagcactaaa tcggaacccct aaagggagcc cccgatttag agcttgacgg ggaaaagccgg     1680 cgaacgtggc gagaaaggaa gggaagaaag cgaaaggagc gggcgctagg gcgctggcaa     1740
gtgtagcggt cacgctgcgc gtaaccacca cacccgccgc gcttaatgcg ccgctacagg     1800
gcgcgtcgcg ccattcgcca ttcaggctgc gcaactgttg ggaagggcga tcggtgcggg     1860
cctcttcgct attacgccag ctggcgaaag ggggatgtgc tgcaaggcga ttaagttggg     1920
taacgccagg gttttcccag tcacgacgtt gtaaaacgac ggccagtgag cgcgcgtaat     1980
acgactcact ataggggaa ttgggtaccg ggcccccct cgaggtcgac tggccattaa     2040
tctttcccat attagatttc gccaagccat gaaagttcaa gaaaggtctt tagacgaatt     2100
acccttcatt tctcaaactg gcgtcaaggg atcctggtat ggttttatcg ttttatttct     2160
ggttcttata gcatcgtttt ggacttctct gttcccatta gcggttcag gagccagcgc     2220 agaatcattc tttgaaggat acttatcctt tccaattttg attgtctgtt acgttggaca     2280
taaactgtat actagaaatt ggactttgat ggtgaaacta aagatatgg atcttgatac     2340 cggcagaaaa caagtagatt tgactcttcg tagggaagaa atgaggattg agcgagaaac     2400
attagcaaaa agatccttcg taacaagatt tttacatttc tggtgttgaa gggaaagata     2460
tgagctatac agcggaattt ccatatcact cagattttgt tatctaattt tttccttccc     2520
acgtccgcgg gaatctgtgt atattactgc atctagatat atgttatctt atcttggcgc     2580
```

```
gtacatttaa ttttcaacgt attctataag aaattgcggg agttttttc atgtagatga    2640
tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaaga    2880
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tcttttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg ttttttacca tacccgggcc    3780
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca cttttttggcg catgggtgac cattaaatac    3960
aactgcattc cccgcagcta tcataccctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acattttcaa atactccaaa acatgaagag ttatctttgt aattctttaa    4380
gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca ataccctaccg tctttatata cttattagtc aagtagggga ataatttcag    4620
ggaactggtt tcaaccttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc    4800
tgttctctgt agttgcgcta agagaatgga cctatgaact gatggttggt gaagaaaaca    4860
atattttggt gctgggattc tttttttttc tggatgccag cttaaaaagc gggctccatt    4920
```

```
atatttagtg gatgccagga ataaactgtt cacccagaca cctacgatgt tatatattct   4980
gtgtaacccg ccccctattt tgggcatgta cgggttacag cagaattaaa aggctaattt   5040
tttgactaaa taaagttagg aaaatcacta ctattaatta tttacgtatt ctttgaaatg   5100
gcagtattga taatgataaa ctcgaactga aaaagcgtgt tttttattca aaatgattct   5160
aactccctta cgtaatcaag gaatcttttt gccttggcct ccgcgtcatt aaacttcttg   5220
ttgttgacgc taacattcaa cgctagtata tattcgtttt tttcaggtaa gttcttttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat   5400
ttaaatcttg gctctcttgg gctcaaggtg acaaggtcct cgaaaatagg gcgcgcccca   5460
ccgcggtgga gctccagctt tgttcccctt tagtgagggt taattgcgcg cttggcgtaa   5520
tcatggtcat agctgtttcc tgtgtgaaat tgttatccgc tcacaattcc acacaacata   5580
ggagccggaa gcataaagtg taaagcctgg ggtgcctaat gagtgaggta actcacatta   5640
attgcgttgc gctcactgcc cgcttttcag tcggaaaacc tgtcgtgcca gctgcattaa   5700
tgaatcggcc aacgcgcggg gagaggcggt ttgcgtattg ggcgctcttc cgcttcctcg   5760
ctcactgact cgctgcgctc ggtcgttcgg ctgcggcgag cggtatcagc tcactcaaag   5820
gcggtaatac ggttatccac agaatcaggg gataacgcag gaaagaacat gtgagcaaaa   5880
ggccagcaaa aggccaggaa ccgtaaaaag gccgcgttgc tggcgttttt ccataggctc   5940
cgcccccctg acgagcatca caaaaatcga cgctcaagtc agaggtggcg aaacccgaca   6000
ggactataaa gataccaggc gtttccccct ggaagctccc tcgtgcgctc tcctgttccg   6060
accctgccgc ttaccggata cctgtccgcc tttctccctt cgggaagcgt ggcgctttct   6120
catagctcac gctgtaggta tctcagttcg gtgtaggtcg ttcgctccaa gctgggctgt   6180
gtgcacgaac cccccgttca gcccgaccgc tgcgccttat ccggtaacta tcgtcttgag   6240
tccaacccgg taagacacga cttatcgcca ctggcagcag ccactggtaa caggattagc   6300
agagcgaggt atgtaggcgg tgctacagag ttcttgaagt ggtggcctaa ctacggctac   6360
actagaagga cagtatttgg tatctgcgct ctgctgaagc cagttacctt cggaaaaaga   6420
gttggtagct cttgatccgg caaacaaacc accgctggta gcggtggttt ttttgtttgc   6480
aagcagcaga ttacgcgcag aaaaaaagga tctcaagaag atcctttgat cttttctacg   6540
gggtctgacg ctcagtggaa cgaaaactca cgttaaggga ttttggtcat gagattatca   6600
aaaaggatct tcacctagat ccttttaaat taaaaatgaa gttttaaatc aatctaaagt   6660
atatatgagt aaacttggtc tgacagttac caatgcttaa tcagtgaggc acctatctca   6720
gcgatctgtc tatttcgttc atccatagtt gcctgactcc ccgtcgtgta gataactacg   6780
atacgggagg gcttaccatc tggccccagt gctgcaatga taccgcgaga cccacgctca   6840
ccggctccag atttatcagc aataaaccag ccagccggaa gggccgagcg cagaagtggt   6900
cctgcaactt tatccgcctc catccagtct attaattgtt gccgggaagc tagagtaagt   6960
agttcgccag ttaatagttt gcgcaacgtt gttgccattg ctacaggcat cgtggtgtca   7020
cgctcgtcgt ttggtatggc ttcattcagc tccggttccc aacgatcaag gcgagttaca   7080
tgatccccca tgttgtgcaa aaaagcggtt agctccttcg gtcctccgat cgttgtcaga   7140
agtaagttgg ccgcagtgtt atcactcatg gttatggcag cactgcataa ttctcttact   7200
gtcatgccat ccgtaagatg cttttctgtg actggtgagt actcaaccaa gtcattctga   7260
gaatagtgta tgcggcgacc gagttgctct tgcccggcgt caatacggga taataccgcg   7320
```

```
ccacatagca gaactttaaa agtgctcatc attggaaaac gttcttcggg gcgaaaactc      7380
tcaaggatct taccgctgtt gagatccagt tcgatgtaac ccactcgtgc acccaactga      7440
tcttcagcat cttttacttt caccagcgtt tctgggtgag caaaaacagg aaggcaaaat      7500
gccgcaaaaa agggaataag ggcgacacgg aaatgttgaa tactcatact cttccttttt      7560
caatattatt gaagcattta tcagggttat tgtctcatga gcggatacat atttgaatgt      7620
atttagaaaa ataaacaaat aggggttccg cgcacatttc cccgaaaagt gccacctgaa      7680
cgaagcatct gtgcttcatt ttgtagaaca aaaatgcaac gcgagagcgc taatttttca      7740
aacaaagaat ctgagctgca ttttacaga acagaaatgc aacgcgaaag cgctatttta       7800
ccaacgaaga atctgtgctt cattttgta aaacaaaaat gcaacgcgag agcgctaatt       7860
tttcaaacaa agaatctgag ctgcatttt acagaacaga aatgcaacgc gagagcgcta       7920
ttttaccaac aaagaatcta tacttctttt ttgttctaca aaatgcatc ccgagagcgc       7980 tatttttcta acaaagcatc ttagattact tttttctcc tttgtgcgct ctataatgca       8040
gtctcttgat aacttttgc actgtaggtc cgttaaggtt agaagaaggc tactttggtg       8100
tctattttct cttccataaa aaagcctga ctccacttcc cgcgtttact gattactagc       8160
gaagctgcgg gtgcatttt tcaagataaa ggcatccccg attatattct ataccgatgt       8220
ggattgcgca tactttgtga acagaaagtg atagcgttga tgattcttca ttggtcagaa      8280
aattatgaac ggtttcttct attttgtctc tatatactac gtataggaaa tgtttacatt      8340
ttcgtattgt tttcgattca ctctatgaat agttcttact acaatttttt tgtctaaaga     8400
gtaatactag agataaacat aaaaaatgta gaggtcgagt ttagatgcaa gttcaaggag      8460
cgaaaggtgg atgggtaggt tatataggga tatagcacag agatatatag caaagagata      8520
cttttgagca atgtttgtgg aagcggtatt cgcaatattt tagtagctcg ttacagtccg     8580
gtgcgttttt ggttttttga aagtgcgtct tcagagcgct tttggttttc aaaagcgctc     8640
tgaagttcct atactttcta gagaatagga acttcggaat aggaacttca aagcgtttcc     8700
gaaaacgagc gcttccgaaa atgcaacgcg agctgcgcac atacagctca ctgttcacgt     8760
cgcacctata tctgcgtgtt gcctgtatat atatatacat gagaagaacg gcatagtgcg     8820
tgtttatgct taaatgcgta cttatatgcg tctatttatg taggatgaaa ggtagtctag     8880
tacctcctgt gatattatcc cattccatgc ggggtatcgt atgcttcctt cagcactacc     8940
ctttagctgt tctatatgct gccactcctc aattggatta gtctcatcct tcaatgctat     9000
catttccttt gatattggat catactaaga aaccattatt atcatgacat taacctataa     9060
aaataggcgt atcacgaggc cctttcgtc                                        9089
```

<210> SEQ ID NO 121
<211> LENGTH: 1023
<212> TYPE: DNA
<213> ORGANISM: Saccharomyces cerevisiae

<400> SEQUENCE: 121

```
caccgcggtg gggcgcgccc tatttttcgag gaccttgtca ccttgagccc aagagagcca       60
agatttaaat tttcctatga cttgatgcaa attcccaaag ctaataacat gcaagacacg      120
tacggtcaag aagacatatt tgacctctta acaggttcag acgcgactgc ctcatcagta      180
agacccgttg aaaagaactt acctgaaaaa aacgaatata tactagcgtt gaatgttagc      240
gtcaacaaca gaagtttaa tgacgcggag gccaaggcaa aagattcct tgattacgta       300
```

```
agggagttag aatcattttg aataaaaaac acgcttttc agttcgagtt tatcattatc    360
aatactgcca tttcaaagaa tacgtaaata attaatagta gtgatttcc taactttatt    420 tagtcaaaaa attagccttt taattctgct gtaacccgta catgcccaaa ataggggcg    480 ggttacacag aatatataac atcgtaggtg tctgggtgaa cagtttattc ctggcatcca    540
ctaaatataa tggagcccgc tttttaagct ggcatccaga aaaaaaaga atcccagcac    600 caaaatattg ttttcttcac caaccatcag ttcataggtc cattctctta gcgcaactac    660
agagaacagg ggcacaaaca ggcaaaaaac gggcacaacc tcaatggagt gatgcaacct    720
gcctggagta aatgatgaca caaggcaatt gacccacgca tgtatctatc tcattttctt    780
acaccttcta ttaccttctg ctctctctga tttggaaaaa gctgaaaaaa aaggttgaaa    840
ccagttccct gaattattc ccctacttga ctaataagta tataaagacg gtaggtattg    900
attgtaattc tgtaaatcta tttcttaaac ttcttaaatt ctacttttat agttagtctt    960 tttttagtt ttaaaacacc aagaacttag tttcgaataa acacacataa actagtaaac   1020
aaa                                                                 1023

<210> SEQ ID NO 122
<211> LENGTH: 21
<212> TYPE: DNA
<213> ORGANISM: Artificial Sequence
<220> FEATURE:
<223> OTHER INFORMATION: primer

<400> SEQUENCE: 122
caaaagctga gctccaccgc g                                              21

<210> SEQ ID NO 123
<211> LENGTH: 44
<212> TYPE: DNA
<213> ORGANISM: Artificial Sequence
<220> FEATURE:
<223> OTHER INFORMATION: primer

<400> SEQUENCE: 123
gtttactagt ttatgtgtgt ttattcgaaa ctaagttctt ggtg                      44

<210> SEQ ID NO 124

<400> SEQUENCE: 124

000

<210> SEQ ID NO 125
<211> LENGTH: 39
<212> TYPE: DNA
<213> ORGANISM: Artificial Sequence
<220> FEATURE:
<223> OTHER INFORMATION: primer

<400> SEQUENCE: 125
cacacatatt acaatagcta gctgaggatg aaagctctg                            39

<210> SEQ ID NO 126
<211> LENGTH: 39
<212> TYPE: DNA
<213> ORGANISM: Artificial Sequence
<220> FEATURE:
<223> OTHER INFORMATION: primer

<400> SEQUENCE: 126
```
cagagctttc atcctcagct agctattgta atatgtgtg 39

<210> SEQ ID NO 127
<211> LENGTH: 9491
<212> TYPE: DNA
<213> ORGANISM: Artificial Sequence
<220> FEATURE:
<223> OTHER INFORMATION: constructed plasmid

<400> SEQUENCE: 127

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accataaatt cccgttttaa gagcttggtg agcgctagga gtcactgcca ggtatcgttt   240
gaacacggca ttagtcaggg aagtcataac acagtccttt cccgcaattt tcttttttcta  300
ttactcttgg cctcctctag tacactctat atttttttat gcctcggtaa tgattttcat   360
tttttttttt cccctagcgg atgactcttt tttttcttta gcgattggca ttatcacata   420
atgaattata cattatataa agtaatgtga tttcttcgaa gaatatacta aaaaatgagc   480
aggcaagata aacgaaggca aagatgacag agcagaaagc cctagtaaag cgtattacaa   540
atgaaaccaa gattcagatt gcgatctctt taaagggtgg tcccctagcg atagagcact   600
cgatcttccc agaaaagag gcagaagcag tagcagaaca ggccacacaa tcgcaagtga   660
ttaacgtcca cacaggtata gggtttctgg accatatgat acatgctctg gccaagcatt   720
ccggctggtc gctaatcgtt gagtgcattg gtgacttaca catagacgac catcacacca   780
ctgaagactg cgggattgct ctcggtcaag cttttaaaga ggccctactg gcgcgtggag   840
taaaaaggtt tggatcagga tttgcgcctt tggatgaggc actttccaga gcggtggtag   900
atctttcgaa caggccgtac gcagttgtcg aacttggttt gcaaagggag aaagtaggag   960
atctctcttg cgagatgatc ccgcattttc ttgaaagctt tgcagaggct agcagaatta  1020
ccctccacgt tgattgtctg cgaggcaaga atgatcatca ccgtagtgag agtgcgttca  1080
aggctcttgc ggttgccata agagaagcca cctcgcccaa tggtaccaac gatgttccct  1140
ccaccaaagg tgttcttatg tagtgacacc gattatttaa agctgcagca tacgatatat  1200
atacatgtgt atatatgtat acctatgaat gtcagtaagt atgtatacga acagtatgat  1260
actgaagatg acaaggtaat gcatcattct atacgtgtca ttctgaacga ggcgcgcttt  1320
cctttttttct ttttgctttt tcttttttttt tctcttgaac tcgacggatc tatgcggtgt  1380
gaaataccgc acagatgcgt aaggagaaaa taccgcatca ggaaattgta aacgttaata  1440
ttttgttaaa attcgcgtta aatttttgtt aaatcagctc attttttaac caataggccg  1500
aaatcggcaa aatcccttat aaatcaaaag aatagaccga gatagggttg agtgttgttc  1560
cagtttggaa caagagtcca ctattaaaga acgtggactc caacgtcaaa gggcgaaaaa  1620
ccgtctatca gggcgatggc ccactacgtg aaccatcacc taatcaagt tttttggggt  1680
cgaggtgccg taaagcacta atcggaacc ctaaagggag cccccgattt agagcttgac  1740
ggggaaagcc ggcgaacgtg gcgagaaagg aaggaagaa agcgaaagga gcgggcgcta  1800
gggcgctggc aagtgtagcg gtcacgctgc gcgtaaccac cacacccgcc gcgcttaatg  1860
cgccgctaca gggcgcgtcg cgccattcgc cattcaggct gcgcaactgt tgggaagggc  1920
gatcggtgcg ggcctcttcg ctattacgcc agctggcgaa aggggggatgt gctgcaaggc  1980
gattaagttg ggtaacgcca gggttttccc agtcacgacg ttgtaaaacg acggccagtg  2040
```

```
agcgcgcgta atacgactca ctatagggcg aattgggtac cgggccccccc ctcgaggtcg    2100 acggcgcgcc actggtagag agcgactttg tatgccccaa ttgcgaaacc cgcgatatcc    2160
ttctcgattc tttagtaccc gaccaggaca aggaaaagga ggtcgaaacg ttttttgaaga   2220 aacaagagga actacacgga agctctaaag atggcaacca gccagaaact aagaaaatga    2280
agttgatgga tccaactggc accgctggct tgaacaacaa taccagcctt ccaacttctg    2340
taaataacgg cggtacgcca gtgccaccag taccgttacc tttcggtata cctcctttcc    2400
ccatgtttcc aatgcccttc atgcctccaa cggctactat cacaaatcct catcaagctg    2460
acgcaagccc taagaaatga ataacaatac tgacagtact aaataattgc ctacttggct    2520
tcacatacgt tgcatacgtc gatatagata ataatgataa tgacagcagg attatcgtaa    2580
tacgtaatag ttgaaaatct caaaaatgtg tgggtcatta cgtaaataat gataggaatg    2640
ggattcttct attttttcctt tttccattct agcagccgtc gggaaaacgt ggcatcctct    2700
ctttcgggct caattggagt cacgctgccg tgagcatcct ctctttccat atctaacaac    2760
tgagcacgta accaatggaa aagcatgagc ttagcgttgc tccaaaaaag tattggatgg    2820
ttaataccat ttgtctgttc tcttctgact ttgactcctc aaaaaaaaaa aatctacaat    2880
caacagatcg cttcaattac gccctcacaa aaactttttt ccttcttctt cgcccacgtt    2940 aaatttatc cctcatgttg tctaacggat ttctgcactt gatttattat aaaaagacaa     3000
agacataata cttctctatc aatttcagtt attgttcttc cttgcgttat tcttctgttc    3060
ttctttttct tttgtcatat ataaccataa ccaagtaata catattcaaa ctagtatgac    3120
tgacaaaaaa actcttaaag acttaagaaa tcgtagttct gtttacgatt caatggttaa    3180
atcacctaat cgtgctatgt tgcgtgcaac tggtatgcaa gatgaagact ttgaaaaacc    3240
tatcgtcggt gtcatttcaa cttgggctga aaacacacct tgtaatatcc acttacatga    3300
ctttggtaaa ctagccaaag tcggtgttaa ggaagctggt gcttggccag ttcagttcgg   3360
aacaatcacg gtttctgatg aatcgccat gggaacccaa ggaatgcgtt tctccttgac    3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaagaaa gcagatattg aagaagctgg    3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag ggtaccagc agttatgaaa tatctcctta aaaatggctt    4140
ccttcatggt gaccgtatca cttgtactgg caaaacagtc gctgaaaatt tgaaggcttt   4200
tgatgattta acacctggtc aaaaggttat tatgccgctt gaaaatccta acgtgaaga    4260 tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
```

```
cattgaagct gtcttgaatg atgatattgt tgatggtgat gttgttgtcg tacgttttgt     4440
aggaccaaag ggcggtcctg gtatgcctga aatgctttcc ctttcatcaa tgattgttgg     4500
taaagggcaa ggtgaaaaag ttgcccttct gacagatggc cgcttctcag gtggtactta     4560
tggtcttgtc gtgggtcata tcgctcctga agcacaagat ggcggtccaa tcgcctacct     4620
gcaaacagga gacatagtca ctattgacca agacactaag gaattacact tgatatctc     4680 cgatgaagag ttaaaacatc gtcaagagac cattgaattg ccaccgctct attcacgcgg     4740
tatccttggt aaatatgctc acatcgtttc gtctgcttct aggggagccg taacagactt     4800
ttggaagcct gaagaaactg gcaaaaaatg ttgtcctggt tgctgtggtt aagcggccgc     4860
gttaattcaa attaattgat atagtttttt aatgagtatt gaatctgttt agaaataatg     4920
gaatattatt tttatttatt tatttatatt attggtcggc tcttttcttc tgaaggtcaa     4980
tgacaaaatg atatgaagga aataatgatt tctaaaattt tacaacgtaa gatattttta     5040
caaaagccta gctcatcttt tgtcatgcac tattttactc acgcttgaaa ttaacggcca     5100
gtccactgcg gagtcatttc aaagtcatcc taatcgatct atcgtttttg atagctcatt     5160
ttggagttcg cgattgtctt ctgttattca caactgtttt aattttttatt tcattctgga     5220 actcttcgag ttctttgtaa agtctttcat agtagcttac tttatcctcc aacatattta     5280
acttcatgtc aatttcggct cttaaatttt ccacatcatc aagttcaaca tcatcttta     5340 acttgaattt attctctagc tcttccaacc aagcctcatt gctccttgat ttactggtga     5400
aaagtgatac actttgcgcg caatccaggt caaaactttc ctgcaaagaa ttcaccaatt     5460
tctcgacatc atagtacaat ttgttttgtt ctcccatcac aatttaatat acctgatgga     5520
ttcttatgaa gcgctgggta atggacgtgt cactctactt cgcctttttc cctactcctt     5580
ttagtacgga agacaatgct aataaataag agggtaataa taatattatt aatcggcaaa     5640
aaagattaaa cgccaagcgt ttaattatca gaaagcaaac gtcgtaccaa tccttgaatg     5700
cttcccaatt gtatattaag agtcatcaca gcaacatatt cttgttatta aattaattat     5760
tattgatttt tgatattgta taaaaaaacc aaatatgtat aaaaaaagtg aataaaaaat     5820
accaagtatg gagaaatata ttagaagtct atacgttaaa ccaccgcggt ggagctccag     5880 ctttgttcc ctttagtgag ggttaattgc gcgcttggcg taatcatggt catagctgtt     5940
tcctgtgtga attgttatc cgctcacaat tccacacaac ataggagccg aagcataaa      6000 gtgtaaagcc tggggtgcct aatgagtgag gtaactcaca ttaattgcgt tgcgctcact     6060
gcccgctttc cagtcgggaa acctgtcgtg ccagctgcat taatgaatcg gccaacgcgc     6120
ggggagaggc ggtttgcgta ttgggcgctc ttccgcttcc tcgctcactg actcgctgcg     6180
ctcggtcgtt cggctgcggc gagcggtatc agctcactca aaggcggtaa tacggttatc     6240
cacagaatca ggggataacg caggaaagaa catgtgagca aaaggccagc aaaaggccag     6300
gaaccgtaaa aaggccgcgt tgctggcgtt tttccatagg ctccgccccc ctgacgagca     6360
tcacaaaaat cgacgctcaa gtcagaggtg gcgaaacccg acaggactat aaagatacca     6420
ggcgtttccc cctggaagct ccctcgtgcg ctctcctgtt ccgaccctgc cgcttaccgg     6480
atacctgtcc gcctttctcc cttcgggaag cgtggcgctt tctcatagct cacgctgtag     6540
gtatctcagt tcggtgtagg tcgttcgctc caagctgggc tgtgtgcacg aacccccgt     6600 tcagcccgac cgctgcgcct tatccggtaa ctatcgtctt gagtccaacc cggtaagaca     6660
cgacttatcg ccactggcag cagccactgg taacaggatt agcagagcga ggtatgtagg     6720
cggtgctaca gagttcttga agtggtggcc taactacggc tacactagaa ggacagtatt     6780
```

```
tggtatctgc gctctgctga agccagttac cttcggaaaa agagttggta gctcttgatc    6840
cggcaaacaa accaccgctg gtagcggtgg ttttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020 gatccttttta aattaaaaat gaagttttaa atcaatctaa agtatatatg agtaaacttg    7080
gtctgacagt taccaatgct taatcagtga ggcacctatc tcagcgatct gtctatttcg    7140
ttcatccata gttgcctgac tccccgtcgt gtagataact acgatacggg agggcttacc    7200
atctggcccc agtgctgcaa tgataccgcg agacccacgc tcaccggctc cagatttatc    7260
agcaataaac cagccagccg aagggccga gcgcagaagt ggtcctgcaa ctttatccgc    7320
ctccatccag tctattaatt gttgccggga agctagagta agtagttcgc cagttaatag    7380
tttgcgcaac gttgttgcca ttgctacagg catcgtggtg tcacgctcgt cgtttggtat    7440
ggcttcattc agctccggtt cccaacgatc aaggcgagtt acatgatccc ccatgttgtg    7500
caaaaaagcg gttagctcct tcggtcctcc gatcgttgtc agaagtaagt tggccgcagt    7560
gttatcactc atggttatgg cagcactgca taattctctt actgtcatgc catccgtaag    7620
atgcttttct gtgactggtg agtactcaac caagtcattc tgagaatagt gtatgcggcg    7680
accgagttgc tcttgcccgg cgtcaatacg ggataatacc gcgccacata gcagaacttt    7740
aaaagtgctc atcattggaa aacgttcttc ggggcgaaaa ctctcaagga tcttaccgct    7800
gttgagatcc agttcgatgt aacccactcg tgcacccaac tgatcttcag catcttttac    7860
tttcaccagc gtttctgggt gagcaaaaac aggaaggcaa aatgccgcaa aaaagggaat    7920
aagggcgaca cggaaatgtt gaatactcat actcttcctt tttcaatatt attgaagcat    7980
ttatcagggt tattgtctca tgagcggata catatttgaa tgtatttaga aaaataaaca    8040
aataggggtt ccgcgcacat ttccccgaaa agtgccacct gaacgaagca tctgtgcttc    8100
attttgtaga acaaaaatgc aacgcgagag cgctaatttt tcaaacaaag aatctgagct    8160 gcattttttac agaacagaaa tgcaacgcga aagcgctatt ttaccaacga gaatctgtg    8220 cttcattttt gtaaaacaaa aatgcaacgc gagagcgcta ttttttcaaa caagaatct    8280 gagctgcatt tttacagaac agaaatgcaa cgcgagagcg ctattttacc aacaaagaat    8340
ctatacttct tttttgttct acaaaaatgc atcccgagag cgctattttt ctaacaaagc    8400
atcttagatt acttttttc tcctttgtgc gctctataat gcagtctctt gataacttt    8460 tgcactgtag gtccgttaag gttagaagaa ggctactttg gtgtctattt tctcttccat    8520
aaaaaaagcc tgactccact tcccgcgttt actgattact agcgaagctg cgggtgcatt    8580
ttttcaagat aaaggcatcc ccgattatat tctataccga tgtggattgc gcatactttg    8640
tgaacagaaa gtgatagcgt tgatgattct tcattggtca gaaaattatg aacggtttct    8700
tctattttgt ctctatatac tacgtatagg aaatgtttac attttcgtat tgttttcgat    8760
tcactctatg aatagttctt actacaattt ttttgtctaa agagtaatac tagagataaa    8820
cataaaaaat gtagaggtcg agtttagatg caagttcaag gagcgaaagg tggatgggta    8880
ggttatatag ggatatagca cagagatata tagcaaagag atactttga gcaatgtttg    8940 tggaagcggt attcgcaata ttttagtagc tcgttacagt ccggtgcgtt tttggttttt    9000
tgaaagtgcg tcttcagagc gcttttggtt ttcaaaagcg ctctgaagtt cctatacttt    9060
ctagagaata ggaacttcgg aataggaact tcaaagcgtt tccgaaaacg agcgcttccg    9120
```

```
aaaatgcaac gcgagctgcg cacatacagc tcactgttca cgtcgcacct atatctgcgt    9180
gttgcctgta tatatatata catgagaaga acggcatagt gcgtgtttat gcttaaatgc    9240
gtacttatat gcgtctattt atgtaggatg aaaggtagtc tagtacctcc tgtgatatta    9300
tcccattcca tgcggggtat cgtatgcttc cttcagcact accctttagc tgttctatat    9360
gctgccactc ctcaattgga ttagtctcat ccttcaatgc tatcatttcc tttgatattg    9420
gatcatctaa gaaaccatta ttatcatgac attaacctat aaaaataggc gtatcacgag    9480
gccctttcgt c                                                        9491

<210> SEQ ID NO 128
<211> LENGTH: 1000
<212> TYPE: DNA
<213> ORGANISM: Saccharomyces cerevisiae

<400> SEQUENCE: 128
gttaattcaa attaattgat atagtttttt aatgagtatt gaatctgttt agaaataatg      60
gaatattatt tttatttatt tatttatatt attggtcggc tctttttcttc tgaaggtcaa     120 tgacaaaatg atatgaagga ataatgatt tctaaaattt tacaacgtaa gatattttta      180
caaaagccta gctcatcttt tgtcatgcac tattttactc acgcttgaaa ttaacggcca      240
gtccactgcg gagtcatttc aaagtcatcc taatcgatct atcgttttg atagctcatt      300 ttggagttcg cgattgtctt ctgttattca caactgtttt aattttattt tcattctgga     360
actcttcgag ttctttgtaa agtctttcat agtagcttac tttatcctcc aacatattta     420
acttcatgtc aatttcggct cttaaatttt ccacatcatc aagttcaaca tcatctttta     480
acttgaattt attctctagc tcttccaacc aagcctcatt gctccttgat ttactggtga     540
aaagtgatac actttgcgcg caatccaggt caaaactttc ctgcaaagaa ttcaccaatt     600
tctcgacatc atagtacaat ttgttttgtt ctcccatcac aatttaatat acctgatgga     660
ttcttatgaa gcgctgggta atggacgtgt cactctactt cgccttttc cctactcctt     720 ttagtacgga agacaatgct aataaataag agggtaataa taatattatt aatcggcaaa     780
aaagattaaa cgccaagcgt ttaattatca gaaagcaaac gtcgtaccaa tccttgaatg     840
cttcccaatt gtatattaag agtcatcaca gcaacatatt cttgttatta aattaattat     900
tattgatttt tgatattgta taaaaaaacc aaatatgtat aaaaaaagtg aataaaaaat     960
accaagtatg gagaaatata ttagaagtct atacgttaaa                         1000

<210> SEQ ID NO 129
<211> LENGTH: 13114
<212> TYPE: DNA
<213> ORGANISM: Artificial Sequence
<220> FEATURE:
<223> OTHER INFORMATION: constructed plasmid

<400> SEQUENCE: 129
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accataaatt cccgttttaa gagcttggtg agcgctagga gtcactgcca ggtatcgttt     240
gaacacggca ttagtcaggg aagtcataac acagtccttt ccgcaattt tcttttttcta     300 ttactcttgg cctcctctag tacactctat attttttat gcctcggtaa tgattttcat     360
tttttttttt ccacctagcg gatgactctt ttttttttctt agcgattggc attatcacat     420
```

```
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat tttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aggtgttcct tatgtagtga caccgattat ttaaagctgc agcatacgat   1200
atatatacat gtgtatatat gtataccat gaatgtcagt aagtatgtat acgaacagta    1260
tgatactgaa gatgacaagg taatgcatca ttctatacgt gtcattctga acgaggcgcg   1320 cttcctttt tcttttttgc ttttttcttt ttttctctt gaactcgacg gatctatgcg    1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aagaataga ccgagatagg gttgagtgtt    1560
gttccagttt ggaacaagag tccactatta agaacgtgg actccaacgt caaagggcga    1620 aaaccgtct atcagggcga tggcccacta cgtggccggc ttcacatacg ttgcatacgt    1680
cgatatagat aataatgata atgacagcag gattatcgta atacgtaata gctgaaaatc   1740 tcaaaatgt gtgggtcatt acgtaaataa tgataggaat gggattcttc tattttcct    1800 ttttccattc tagcagccgt cgggaaaacg tggcatcctc tctttcgggc tcaattggag   1860
tcacgctgcc gtgagcatcc tctctttcca tatctaacaa ctgagcacgt aaccaatgga   1920
aaagcatgag cttagcgttg ctccaaaaaa gtattggatg gttaatacca tttgtctgtt   1980
ctcttctgac tttgactcct caaaaaaaaa aatctacaat caacagatcg cttcaattac   2040
gccctcacaa aaactttttt ccttcttctt cgcccacgtt aaatttatc cctcatgttg    2100 tctaacggat ttctgcactt gatttattat aaaaagacaa agacataata cttctctatc   2160
aatttcagtt attgttcttc cttgcgttat tcttctgttc ttctttttct tttgtcatat   2220
ataaccataa ccaagtaata catattcaaa acgtgagta tgactgacaa aaaactctt    2280 aaagacttaa gaaatcgtag ttctgtttac gattcaatgg ttaaatcacc taatcgtgct   2340
atgttgcgtg caactggtat gcaagatgaa gactttgaaa aacctatcgt cggtgtcatt   2400
tcaacttggg ctgaaaacac accttgtaat atccacttac atgactttgg taaactagcc   2460
aaagtcggtg ttaaggaagc tggtgcttgg ccagttcagt tcggaacaat cacggtttct   2520
gatggaatcg ccatgggaac ccaaggaatg cgttctccct tgcatctcg tgatattatt    2580 gcagattcta ttgaagcagc catgggaggt cataatgcgg atgcttttgt agccattggc   2640
ggttgtgata aaaacatgcc cggttctgtt atcgctatgg ctaacatgga tatcccagcc   2700
atttttgctt acggcggaac aattgcacct ggtaatttag acggcaaaga tatcgattta   2760
```

```
gtctctgtct ttgaaggtgt cggccattgg aaccacggcg atatgaccaa agaagaagtt    2820
aaagctttgg aatgtaatgc ttgtcccggt cctggaggct gcggtggtat gtatactgct    2880
aacacaatgg cgacagctat tgaagttttg ggacttagcc ttccgggttc atcttctcac    2940
ccggctgaat ccgcagaaaa gaaagcagat attgaagaag ctggtcgcgc tgttgtcaaa    3000
atgctcgaaa tgggcttaaa accttctgac attttaacgc gtgaagcttt tgaagatgct    3060
attactgtaa ctatggctct gggaggttca accaactcaa cccttcacct cttagctatt    3120
gcccatgctg ctaatgtgga attgacactt gatgatttca atactttcca agaaaaagtt    3180
cctcatttgg ctgatttgaa accttctggt caatatgtat ccaagacct ttacaaggtc     3240 ggagggtac cagcagttat gaaatatctc cttaaaaatg gcttccttca tggtgaccgt     3300
atcacttgta ctggcaaaac agtcgctgaa aatttgaagg cttttgatga tttaacacct    3360
ggtcaaaagg ttattatgcc gcttgaaaat cctaaacgtg aagatggtcc gctcattatt    3420
ctccatggta acttggctcc agacggtgcc gttgccaaag tttctggtgt aaaagtgcgt    3480
cgtcatgtcg gtcctgctaa ggtctttaat tctgaagaag aagccattga agctgtcttg    3540
aatgatgata ttgttgatgg tgatgttgtt gtcgtacgtt ttgtaggacc aaagggcggt    3600
cctggtatgc ctgaaatgct tcccttttca tcaatgattg ttggtaaagg caaggtgaa    3660 aaagttgccc ttctgacaga tggccgcttc tcaggtggta cttatggtct tgtcgtgggt    3720
catatcgctc ctgaagcaca agatggcggt ccaatcgcct acctgcaaac aggagacata    3780
gtcactattg accaagacac taaggaatta cactttgata tctccgatga agagttaaaa    3840
catcgtcaag agaccattga attgccaccg ctctattcac gcggtatcct tggtaaaatat   3900 gctcacatcg tttcgtctgc ttctagggga gccgtaacag acttttggaa gcctgaagaa    3960
actggcaaaa aatgttgtcc tggttgctgt ggttaagcgg ccgcgttaat tcaaattaat    4020
tgatatagtt ttttaatgag tattgaatct gtttagaaat aatggaatat tattttatt     4080 tatttattta tattattggt cggctctttt ccttctgaagg tcaatgacaa aatgatatga    4140
aggaaataat gatttctaaa attttacaac gtaagatatt tttacaaaag cctagctcat    4200
cttttgtcat gcactatttt actcacgctt gaaattaacg gccagtccac tgcggagtca    4260
tttcaaagtc atcctaatcg atctatcgtt tttgatagct cattttggag ttcgcgagga    4320
tccactagtt ctagagcggc cgctctagaa ctagtaccac aggtgttgtc ctctgaggac    4380
ataaaataca caccgagatt catcaactca ttgctggagt tagcatatct acaattgggt    4440
gaaatgggga gcgatttgca ggcatttgct cggcatgccg gtagaggtgt ggtcaataag    4500
agcgacctca tgctataccg gagaaagcaa cctgacctac aggaaagagt tactcaagaa    4560
taagaatttt cgttttaaaa cctaagagtc actttaaaat ttgtatacac ttattttttt    4620
tataacttat ttaataataa aaatcataaa tcataagaaa ttcgcttact cttaattaat    4680 caaaagtta aaattgtacg aatagattca ccacttctta acaaatcaaa ccctcattg      4740 attttctcga atggcaatac atgtgtaatt aaaggatcaa gagcaaactt cttcgccata    4800
aagtcggcaa caagttttgg aacactatcc ttgctcttaa aaccgccaaa tatagctccc    4860
ttccatgtac gaccgcttag caacagcata ggattcatcg acaaattttg tgaatcagga    4920
ggaacaccta cgatcacact gactccatat gcctcttgac agcaggacaa cgcagttacc    4980
atagtatcaa gacggcctat aacttcaaaa gagaaatcaa ctccaccgtt tgacatttca    5040
gtaaggactt cttgtattgg tttcttataa tcttgagggt taacacattc agtagccccg    5100
acctccttag cttttgcaaa tttgtcctta ttgatgtcta cacctataat cctcgctgcg    5160
```

```
cctgcagctt tacaccccat aataacgctt agtcctactc ctcctaaacc gaatactgca   5220
caagtcgaac cctgtgtaac cttttgcaact ttaactgcgg aaccgtaacc ggtggaaaat   5280
ccgcacccta tcaagcaaac ttttttccagt ggtgaagctg catcgatttt agcgacagat   5340
atctcgtcca ccactgtgta ttgggaaaat gtagaagtac caaggaaatg gtgtataggt   5400
ttccctctgc atgtaaatct gcttgtacca tcctgcatag tacctctagg catagacaaa   5460 tcattttaa ggcagaaatt accctcagga tgtttgcaga ctctacactt accacattga   5520
ggagtgaaca gtgggatcac tttatcacca ggacgaacag tggtaacacc ttcacctatg   5580
gattcaacga ttccggcagc ctcgtgtccc gcgattactg gcaaaggagt aactagagtg   5640
ccactcacca catggtcgtc ggatctacag attccgtgg caaccatctt gattctaacc   5700
tcgtgtgctt ttggtggcgc tacttctact tcttctatgc taaacggctt tttctcttcc   5760
cacaaaactg ccgctttaca cttaataact ttaccggctg ttgacatcct cagctagcta   5820
ttgtaatatg tgtgtttgtt tggattatta agaagaataa ttacaaaaaa aattacaaag   5880
gaaggtaatt acaacagaat taagaaagga caagaaggag gaagagaatc agttcattat   5940
ttcttctttg ttatataaca aacccaagta gcgatttggc catacattaa aagttgagaa   6000
ccaccctccc tggcaacagc cacaactcgt taccattgtt catcacgatc atgaaactcg   6060
ccgtcagctg aaatttcacc tcagtggatc tctctttta ttcttcatcg ttccactaac   6120 cttttttccat cagctggcag ggaacggaaa gtggaatccc atttagcgag cttcctcttt   6180
tcttcaagaa aagacgaagc ttgtgtgtgg gtgcgcgcgc tagtatcttt ccacattaag   6240
aaatatacca taaaggttac ttagacatca ctatggctat atatatatat atatatatat   6300
gtaacttagc accatcgcgc gtgcatcact gcatgtgtta accgaaaagt ttggcgaaca   6360
cttcaccgac acggtcattt agatctgtcg tctgcattgc acgtccctta gccttaaatc   6420
ctaggcggga gcattctcgt gtaattgtgc agcctgcgta gcaactcaac atagcgtagt   6480
ctacccagtt tttcaagggt ttatcgttag aagattctcc cttttcttcc tgctcacaaa   6540
tcttaaagtc atacattgca cgactaaatg caagcgacgt cagggaaaga tatgagctat   6600
acagcggaat ttccatatca ctcagatttt gttatctaat ttttccttc ccacgtccgc   6660 gggaatctgt gtatattact gcatctagat atatgttatc ttatcttggc gcgtacattt   6720
aattttcaac gtattctata agaaattgcg ggagtttttt tcatgtagat gatactgact   6780
gcacgcaaat ataggcatga tttataggca tgatttgatg gctgtaccga taggaacgct   6840
aagagtaact tcagaatcgt tatcctggcg gaaaaaattc atttgtaaac tttaaaaaaa   6900
aaagccaata tccccaaaat tattaagagc gcctccatta ttaactaaaa tttcactcag   6960
catccacaat gtatcaggta tctactacag atattacatg tggcgaaaaa gacaagaaca   7020
atgcaatagc gcatcaagaa aaaacacaaa gctttcaatc aatgaatcga aaatgtcatt   7080
aaaatagtat ataaattgaa actaagtcat aaagctataa aagaaaatt tatttaaatg   7140 caagatttaa agtaaattca cggccctgca ggcctcagct cttgttttgt tctgcaaata   7200
acttacccat cttttttcaaa actttaggtg caccctcctt tgctagaata agttctatcc   7260
aatacatcct atttggatct gcttgagctt ctttcatcac ggatacgaat tcattttctg   7320
ttctcacaat tttggacaca actctgtctt ccgttgcccc gaaactttct ggcagttttg   7380
agtaattcca cataggaatg tcattataac tctggttcgg accatgaatt tccctctcaa   7440
ccgtgtaacc atcgttatta atgataaagc agattgggtt tatcttctct ctaatggcta   7500
```

```
gtcctaattc ttggacagtc agttgcaatg atccatctcc gataaacaat aaatgtctag    7560
attctttatc tgcaatttgg ctgcctagag ctgcggggaa agtgtatcct atagatcccc    7620
acaagggttg accaataaaa tgtgatttcg atttcagaaa tatagatgag gcaccgaaga    7680
aagaagtgcc ttgttcagcc acgatcgtct cattactttg ggtcaaattt tcgacagctt    7740
gccacagtct atcttgtgac aacagcgcgt tagaaggtac aaaatcttct tgctttttat    7800
ctatgtactt gcctttatat tcaatttcgg acaagtcaag aagagatgat atcagggatt    7860
cgaagtcgaa attttggatt ctttcgttga aaattttacc ttcatcgata ttcaaggaaa    7920
tcattttatt ttcattaaga tggtgagtaa atgcacccgt actagaatcg gtaagcttta    7980
cacccaacat aagaataaaa tcagcagatt ccacaaattc cttcaagttt ggctctgaca    8040
gagtaccgtt gtaaatcccc aaaaatgagg gcaatgcttc atcaacagat gatttaccaa    8100
agttcaaagt agtaataggt aacttagtct ttgaaataaa ctgagtaaca gtcttctcta    8160
ggccgaacga tataatttca tggcctgtga ttacaattgg tttcttggca ttcttcagac    8220
tttcctgtat tttgttcaga atctcttgat cagatgtatt cgacgtggaa ttttccttct    8280
taagaggcaa ggatggtttt tcagccttag cggcagctac atctacaggt aaattgatgt    8340
aaaccggctt tctttccttt agtaaggcag acaaacactct atcaatttca acagttgcat    8400
tctcggctgt caataaagtc ctggcagcag taaccggttc gtgcatcttc ataaagtgct    8460
tgaaatcacc atcagccaac gtatggtgaa caaacttacc ttcgttctgc actttcgagg    8520
taggagatcc cacgatctca acaacaggca ggttctcagc ataggagccc gctaagccat    8580
taactgcgga taattcgcca acaccaaatg tagtcaagaa tgccgcagcc tttttcgttc    8640
ttgcgtaccc gtcggccata taggaggcat ttaactcatt agcatttccc acccatttca    8700
tatctttgtg tgaaataatt tgatctagaa attgcaaatt gtagtcacct ggtactccga    8760
atatttcttc tatacctaat tcgtgtaatc tgtccaacag atagtcacct actgtataca    8820
tgtttaaact ttgtttacta gtttatgtgt gtttattcga aactaagttc ttggtgtttt    8880
aaaactaaaa aaaagactaa ctataaaagt agaatttaag aagtttaaga aatagattta    8940
cagaattaca atcaataacct accgtctttta tatacttatt agtcaagtag gggaataatt    9000
tcagggaact ggtttcaacc ttttttttca gcttttttcca aatcagagag agcagaaggt    9060
aatagaaggt gtaagaaaat gagatagata catgcgtggg tcaattgcct tgtgtcatca    9120
tttactccag gcaggttgca tcactccatt gaggttgtgc ccgttttttg cctgtttgtg    9180
cccctgttct ctgtagttgc gctaagagaa tggacctatg aactgatggt tggtgaagaa    9240 aacaatatttt tggtgctggg attctttttt tttctggatg ccagcttaaa aagcgggctc    9300
cattatattt agtggatgcc aggaataaac tgttcaccca gacacctacg atgttatata    9360
ttctgtgtaa cccgcccccct atttttgggca tgtacgggtt acagcagaat taaaaggcta    9420
attttttgac taaataaagt taggaaaatc actactatta attatttacg tattctttga    9480
aatggcagta ttggagctcc agcttttgtt ccctttagtg agggttaatt gcgcgcttgg    9540
cgtaatcatg gtcatagctg tttcctgtgt gaaattgtta ccgctcaca attccacaca    9600 acatacgagc cggaagcata aagtgtaaag cctggggtgc ctaatgagtg agctaactca    9660
cattaattgc gttgcgctca ctgcccgctt tccagtcggg aaacctgtcg tgccagctgc    9720
attaatgaat cggccaacgc gcggggagag gcggtttgcg tattgggcgc tcttccgctt    9780
cctcgctcac tgactcgctg cgctcggtcg ttcggctgcg gcgagcggta tcagctcact    9840
caaaggcggt aatacggtta tccacagaat caggggataa cgcaggaaag aacatgtgag    9900
```

```
caaaaggcca gcaaaaggcc aggaaccgta aaaaggccgc gttgctggcg ttttcccata    9960
ggctccgccc ccctgacgag catcacaaaa atcgacgctc aagtcagagg tggcgaaacc   10020
cgacaggact ataaagatac caggcgtttc ccctggaag ctccctcgtg cgctctcctg    10080
ttccgaccct gccgcttacc ggatacctgt ccgcctttct cccttcggga agcgtggcgc   10140
tttctcatag ctcacgctgt aggtatctca gttcggtgta ggtcgttcgc tccaagctgg   10200
gctgtgtgca cgaaccccc gttcagcccg accgctgcgc cttatccggt aactatcgtc    10260
ttgagtccaa cccggtaaga cacgacttat cgccactggc agcagccact ggtaacagga   10320
ttagcagagc gaggtatgta ggcggtgcta cagagttctt gaagtggtgg cctaactacg   10380
gctacactag aagaacagta tttggtatct gcgctctgct gaagccagtt accttcggaa   10440
aaagagttgg tagctcttga tccggcaaac aaaccaccgc tggtagcggt ggtttttttg   10500
tttgcaagca gcagattacg cgcagaaaaa aaggatctca agaagatcct ttgatctttt   10560
ctacggggtc tgacgctcag tggaacgaaa actcacgtta agggattttg gtcatgagat   10620
tatcaaaaag gatcttcacc tagatccttt taaattaaaa atgaagtttt aaatcaatct   10680
aaagtatata tgagtaaact tggtctgaca gttaccaatg cttaatcagt gaggcaccta   10740
tctcagcgat ctgtctattt cgttcatcca tagttgcctg actccccgtc gtgtagataa   10800
ctacgatacg ggagggctta ccatctggcc ccagtgctgc aatgataccg cgagacccac   10860
gctcaccggc tccagattta tcagcaataa accagccagc cggaagggcc gagcgcagaa   10920
gtggtcctgc aactttatcc gcctccatcc agtctattaa ttgttgccgg gaagctagag   10980
taagtagttc gccagttaat agtttgcgca acgttgttgc cattgctaca ggcatcgtgg   11040
tgtcacgctc gtcgtttggt atggcttcat tcagctccgg ttcccaacga tcaaggcgag   11100
ttacatgatc ccccatgttg tgcaaaaaag cggttagctc cttcggtcct ccgatcgttg   11160
tcagaagtaa gttggccgca gtgttatcac tcatggttat ggcagcactg cataattctc   11220
ttactgtcat gccatccgta agatgctttt ctgtgactgg tgagtactca accaagtcat   11280
tctgagaata gtgtatgcgg cgaccgagtt gctcttgccc ggcgtcaata cgggataata   11340
ccgcgccaca tagcagaact ttaaaagtgc tcatcattgg aaaacgttct cggggcgaa    11400
aactctcaag gatcttaccg ctgttgagat ccagttcgat gtaacccact cgtgcaccca   11460
actgatcttc agcatctttt actttcacca gcgtttctgg gtgagcaaaa acaggaaggc   11520
aaaatgccgc aaaaaaggga ataagggcga cacggaaatg ttgaatactc atactcttcc   11580
tttttcaata ttattgaagc atttatcagg gttattgtct catgagcgga tacatatttg   11640
aatgtattta gaaaaataaa caaatagggg ttccgcgcac atttccccga aaagtgccac   11700
ctgaacgaag catctgtgct tcattttgta gaacaaaaat gcaacgcgag agcgctaatt   11760
tttcaaacaa gaatctgag ctgcattttt acagaacaga aatgcaacgc gaaagcgcta   11820
ttttaccaac gaagaatctg tgcttcattt ttgtaaaaca aaaatgcaac gcgagagcgc   11880
taatttttca acaaagaat ctgagctgca ttttacaga acagaaatgc aacgcgagag   11940
cgctatttta ccaacaaaga atctatactt ctttttgtt ctacaaaaat gcatcccgag   12000
agcgctattt ttctaacaaa gcatcttaga ttactttttt tctccctttgt gcgctctata   12060
atgcagtctc ttgataactt tttgcactgt aggtccgtta aggttagaag aaggctactt   12120
tggtgtctat tttctcttcc ataaaaaaag cctgactcca cttcccgcgt ttactgatta   12180
ctagcgaagc tgcgggtgca ttttttcaag ataaaggcat ccccgattat attctatacc   12240
```

```
gatgtggatt gcgcatactt tgtgaacaga aagtgatagc gttgatgatt cttcattggt    12300
cagaaaatta tgaacggttt cttctatttt gtctctatat actacgtata ggaaatgttt    12360
acattttcgt attgttttcg attcactcta tgaatagttc ttactacaat ttttttgtct    12420
aaagagtaat actagagata aacataaaaa atgtagaggt cgagtttaga tgcaagttca    12480
aggagcgaaa ggtggatggg taggttatat agggatatag cacagagata tatagcaaag    12540
agatactttt gagcaatgtt tgtggaagcg gtattcgcaa tattttagta gctcgttaca    12600
gtccggtgcg ttttggttt tttgaaagtg cgtcttcaga gcgcttttgg ttttcaaaag     12660
cgctctgaag ttcctatact ttctagaaaa taggaacttc ggaataggaa cttcaaagcg    12720
tttccgaaaa cgagcgcttc cgaaaatgca acgcgagctg cgcacataca gctcactgtt    12780
cacgtcgcac ctatatctgc gtgttgcctg tatatatata tacatgagaa gaacggcata    12840
gtgcgtgttt atgcttaaat gcgtacttat atgcgtctat ttatgtagga tgaaaggtag    12900
tctagtacct cctgtgatat tatcccattc catgcggggt atcgtatgct tccttcagca    12960
ctacccttta gctgttctat atgctgccac tcctcaattg gattagtctc atccttcaat    13020
gctatcattt cctttgatat tggatcatac taagaaacca ttattatcat gacattaacc    13080
tataaaaata ggcgtatcac gaggccctt cgtc                                 13114

<210> SEQ ID NO 130
<211> LENGTH: 4236
<212> TYPE: DNA
<213> ORGANISM: Artificial Sequence
<220> FEATURE:
<223> OTHER INFORMATION: construct

<400> SEQUENCE: 130
gatccgcatt gcggattacg tattctaatg ttcagataac ttcgtatagc atacattata      60
cgaagttatg cagattgtac tgagagtgca ccataccaca gcttttcaat tcaattcatc     120
attttttttt tattcttttt tttgatttcg gtttctttga aattttttg attcggtaat      180 ctccgaacag aaggaagaac gaaggaagga gcacagactt agattggtat atatacgcat     240
atgtagtgtt gaagaaacat gaaattgccc agtattctta acccaactgc acagaacaaa     300
aacctgcagg aaacgaagat aaatcatgtc gaaagctaca tataaggaac gtgctgctac     360
tcatcctagt cctgttgctg ccaagctatt taatatcatg cacgaaaagc aaacaaactt     420
gtgtgcttca ttggatgttc gtaccaccaa ggaattactg gagttagttg aagcattagg     480
tcccaaaatt tgtttactaa aaacacatgt ggatatcttg actgattttt ccatggaggg     540
cacagttaag ccgctaaagg cattatccgc caagtacaat ttttactct tcgaagacag     600 aaaatttgct gacattggta atacagtcaa attgcagtac tctgcgggtg tatacagaat     660
agcagaatgg gcagacatta cgaatgcaca cggtgtggtg ggcccaggta ttgttagcgg    720
tttgaagcag gcggcagaag aagtaacaaa ggaacctaga ggccttttga tgttagcaga    780
attgtcatgc aagggctccc tatctactgg agaatatact aagggtactg ttgacattgc    840
gaagagcgac aaagattttg ttatcggctt tattgctcaa agagacatgg gtggaagaga    900
tgaaggttac gattggttga ttatgacacc cggtgtgggt ttagatgaca agggagcgc     960 attgggtcaa cagtatagaa ccgtggatga tgtggtctct acaggatctg acattattat   1020
tgttggaaga ggactatttg caaagggaag ggatgctaag gtagagggtg aacgttacag   1080
aaaagcaggc tgggaagcat atttgagaag atgcggccag caaaactaaa aaactgtatt   1140
ataagtaaat gcatgtatac taaactcaca aattagagct tcaatttaat tatatcagtt   1200
```

```
attaccctat gcggtgtgaa ataccgcaca gatgcgtaag gagaaaatac cgcatcagga    1260
aattgtaaac gttaatattt tgttaaaatt cgcgttaaat ttttgttaaa tcagctcatt    1320
ttttaaccaa taggccgaaa tcggcaaaat cccttataaa tcaaaagaat agaccgagat    1380
agggttgagt gttgttccag tttgaacaa gagtccacta ttaaagaacg tggactccaa     1440
cgtcaaaggg cgaaaaaccg tctatcaggg cgatggccca ctacgtgaac catcacccta    1500
atcaagataa cttcgtatag catacattat acgaagttat ccagtgatga tacaacgagt    1560
tagccaaggt gaattcactg gccgtcgttt tacaacgtcg tgactgggaa accctggcg     1620 ttacccaact taatcgcctt gcagcacatc ccccttcgc cagctggcgt aatagcgaag     1680
aggcccgcac cgatcgccct tcccaacagt tgcgcagcct gaatggcgaa tggcgcctga    1740
tgcggtattt tctccttacg catctgtgcg gtatttcaca ccgcatatgg tgcactctca    1800
gtacaatctg ctctgatgcc gcatagttaa gccagccccg acacccgcca cacccgctg     1860 acgcgccctg acgggcttgt ctgctcccgg catccgctta cagacaagct gtgaccgtct    1920
ccgggagctg catgtgtcag aggttttcac cgtcatcacc gaaacgcgcg agacgaaagg    1980
gcctcgtgat acgcctattt ttataggtta atgtcatgat aataatggtt tcttagacgt    2040
caggtggcac ttttcgggga atgtgcgcg gaacccctat ttgtttattt ttctaaatac     2100
attcaaatat gtatccgctc atgagacaat aaccctgata aatgcttcaa taatattgaa    2160
aaaggaagag tatgagtatt caacatttcc gtgtcgccct tattcccttt tttgcggcat    2220
tttgccttcc tgttttgct cacccagaaa cgctggtgaa agtaaaagat gctgaagatc     2280
agttgggtgc acgagtgggt tacatcgaac tggatctcaa cagcggtaag atccttgaga    2340
gttttcgccc cgaagaacgt tttccaatga tgagcacttt taaagttctg ctatgtggcg    2400
cggtattatc ccgtattgac gccgggcaag agcaactcgg tcgccgcata cactattctc    2460
agaatgactt ggttgagtac tcaccagtca cagaaaagca tcttacggat ggcatgacag    2520
taagagaatt atgcagtgct gccataacca tgagtgataa cactgcggcc aacttacttc    2580
tgacaacgat cggaggaccg aaggagctaa ccgcttttt gcacaacatg ggggatcatg     2640
taactcgcct tgatcgttgg gaaccggagc tgaatgaagc cataccaaac gacgagcgtg    2700
acaccacgat gcctgtagca atggcaacaa cgttgcgcaa actattaact ggcgaactac    2760
ttactctagc ttcccggcaa caattaatag actggatgga ggcggataaa gttgcaggac    2820
cacttctgcg ctcggccctt ccggctggct ggtttattgc tgataaatct ggagccggtg    2880
agcgtgggtc tcgcggtatc attgcagcac tggggccaga tggtaagccc tcccgtatcg    2940
tagttatcta cacgacgggg agtcaggcaa ctatggatga acgaaataga cagatcgctg    3000
agataggtgc ctcactgatt aagcattggt aactgtcaga ccaagtttac tcatatatac    3060
tttagattga tttaaaactt cattttaat ttaaaggat ctaggtgaag atccttttg       3120 ataatctcat gaccaaaatc ccttaacgtg agttttcgtt ccactgagcg tcagaccccg    3180
tagaaaagat caaaggatct tcttgagatc ctttttttct gcgcgtaatc tgctgcttgc    3240
aaacaaaaaa accaccgcta ccagcggtgg tttgtttgcc ggatcaagag ctaccaactc    3300
tttttccgaa ggtaactggc ttcagcagag cgcagatacc aaatactgtc cttctagtgt    3360
agccgtagtt aggccaccac ttcaagaact ctgtagcacc gcctacatac ctcgctctgc    3420
taatcctgtt accagtggct gctgccagtg gcgataagtc gtgtcttacc gggttggact    3480
caagacgata gttaccggat aaggcgcagc ggtcgggctg aacggggggt tcgtgcacac    3540
```

```
agcccagctt ggagcgaacg acctacaccg aactgagata cctacagcgt gagctatgag    3600
aaagcgccac gcttcccgaa gggagaaagg cggacaggta tccggtaagc ggcagggtcg    3660
gaacaggaga gcgcacgagg gagcttccag ggggaaacgc ctggtatctt tatagtcctg    3720
tcgggtttcg ccacctctga cttgagcgtc gattttgtg atgctcgtca gggggcgga     3780 gcctatggaa aaacgccagc aacgcggcct ttttacggtt cctggccttt tgctggcctt    3840
ttgctcacat gttctttcct gcgttatccc ctgattctgt ggataaccgt attaccgcct    3900
ttgagtgagc tgataccgct cgccgcagcc gaacgaccga gcgcagcgag tcagtgagcg    3960
aggaagcgga gagcgcccca atacgcaaac cgcctctccc cgcgcgttgg ccgattcatt    4020
aatgcagctg gcacgacagg tttcccgact ggaaagcggg cagtgagcgc aacgcaatta    4080
atgtgagtta gctcactcat taggcacccc aggctttaca ctttatgctt ccggctcgta    4140
tgttgtgtgg aattgtgagc ggataacaat ttcacacagg aaacagctat gaccatgatt    4200
acgccaagct tgcatgcctg caggtcgact ctagag                              4236
```

<210> SEQ ID NO 131
<211> LENGTH: 7523
<212> TYPE: DNA
<213> ORGANISM: Artificial Sequence
<220> FEATURE:
<223> OTHER INFORMATION: construct

<400> SEQUENCE: 131

```
ccagcttttg ttcccttag tgagggttaa ttgcgcgctt ggcgtaatca tggtcatagc     60
tgtttcctgt gtgaaattgt tatccgctca caattccaca caacatagga gccggaagca   120
taaagtgtaa agcctggggt gcctaatgag tgaggtaact cacattaatt gcgttgcgct   180
cactgcccgc tttccagtcg ggaaacctgt cgtgccagct gcattaatga atcggccaac   240
gcgcggggag aggcggtttg cgtattgggc gctcttccgc ttcctcgctc actgactcgc   300
tgcgctcggt cgttcggctg cggcgagcgg tatcagctca ctcaaaggcg gtaatacggt   360
tatccacaga atcaggggat aacgcaggaa agaacatgtg agcaaaaggc cagcaaaagg   420
ccaggaaccg taaaaaggcc gcgttgctgg cgtttttcca taggctccgc cccctgacg    480 agcatcacaa aaatcgacgc tcaagtcaga ggtggcgaaa cccgacagga ctataaagat   540
accaggcgtt ccccctggaa gctccctcg tgcgctctcc tgttccgacc ctgccgctta    600
ccggatacct gtccgccttt ctcccttcgg gaagcgtggc gctttctcat agctcacgct   660
gtaggtatct cagttcggtg taggtcgttc gctccaagct gggctgtgtg cacgaacccc   720
ccgttcagcc cgaccgctgc gccttatccg gtaactatcg tcttgagtcc aacccggtaa   780
gacacgactt atcgccactg gcagcagcca ctggtaacag gattagcaga gcgaggtatg   840
taggcggtgc tacagagttc ttgaagtggt ggcctaacta cggctacact agaaggacag   900
tatttggtat ctgcgctctg ctgaagccag ttaccttcgg aaaaagagtt ggtagctctt   960
gatccggcaa acaaaccacc gctggtagcg gtggttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
```

```
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tccccatgt    1620 tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta ataatgcagtc tcttgataac    2580 ttttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacatttc gtattgttttt    2880 cgattcactc tatgaatagt tcttactaca attttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatatttag tagctcgtta cagtccggtg cgttttttggt    3120 tttttgaaag tgcgtcttca gagcgctttt ggttttcaaa agcgctctga agttcctata    3180
ctttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac tcctgtgat    3420 attatcccat tccatgcggg gtatcgtatg cttccttcag cactacccctt tagctgttct    3480 atatgctgcc actcctcaat tggattagtc tcatccttca atgctatcat ttcctttgat    3540
attggatcat ctaagaaacc attattatca tgacattaac ctataaaaat aggcgtatca    3600
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
```

```
gcgcgtcagc gggtgttggc gggtgtcggg gctggcttaa ctatgcggca tcagagcaga    3780
ttgtactgag agtgcaccat aaattcccgt tttaagagct tggtgagcgc taggagtcac    3840
tgccaggtat cgtttgaaca cggcattagt cagggaagtc ataacacagt cctttcccgc    3900
aattttcttt ttctattact cttggcctcc tctagtacac tctatatttt tttatgcctc    3960
ggtaatgatt ttcatttttt ttttccccct agcggatgac tcttttttttt tcttagcgat    4020 tggcattatc acataatgaa ttatacatta tataaagtaa tgtgatttct tcgaagaata    4080
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtatagggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agctttgcag    4620
aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttg cttttttcttt ttttttctct tgaactcgac    4980
ggatctatgc ggtgtgaaat accgcacaga tgcgtaagga gaaataccg catcaggaaa    5040 ttgtaaacgt taatattttg ttaaaattcg cgttaaattt tgttaaatc agctcatttt    5100 ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaaccgtc tatcagggcg atggcccact acgtgaacca tcaccctaat    5280
caagtttttt ggggtcgagg tgccgtaaag cactaaatcg gaaccctaaa gggagccccc    5340
gatttagagc ttgacgggga agccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacagggcg cgtcgcgcca ttcgccattc aggctgcgca    5520
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg gtaccgggc    5700 ccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa cataaagat tctacaatac tagcttttat ggttatgaag aggaaaaatt    5880
ggcagtaacc tggccccaca aaccttcaaa ttaacgaatc aaattaacaa ccataggatg    5940
ataatgcgat tagttttta gccttatttc tggggtaatt aatcagcgaa gcgatgattt    6000
ttgatctatt aacagatata taatggaaa agctgcataa ccactttaac taatactttc    6060
aacattttca gtttgtatta cttcttattc aaatgtcata aaagtatcaa caaaaaattg    6120
```

```
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt     6540 gaacgtgcaa aacaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtatttatg tcctcagagg acaacacctg     7500
tggtccgcca ccgcggtgga gct                                           7523
```

```
<210> SEQ ID NO 132
<211> LENGTH: 29
<212> TYPE: DNA
<213> ORGANISM: Artificial Sequence
<220> FEATURE:
<223> OTHER INFORMATION: Primer

<400> SEQUENCE: 132
ctcgaaacaa taagacgacg atggctctg                                       29

<210> SEQ ID NO 133
<211> LENGTH: 29
<212> TYPE: DNA
<213> ORGANISM: Artificial Sequence
<220> FEATURE:
<223> OTHER INFORMATION: Primer

<400> SEQUENCE: 133
gtctagacca gaagttaaga aggctgtag                                       29

<210> SEQ ID NO 134
<211> LENGTH: 26
<212> TYPE: DNA
<213> ORGANISM: Artificial Sequence
<220> FEATURE:
```

<223> OTHER INFORMATION: Primer

<400> SEQUENCE: 134
tagcacccaa tagagcgccg actgtg                                               26

<210> SEQ ID NO 135
<211> LENGTH: 4519
<212> TYPE: DNA
<213> ORGANISM: Artificial Sequence
<220> FEATURE:
<223> OTHER INFORMATION: Plasmid

<400> SEQUENCE: 135

```
caccttggct aactcgttgt atcatcactg gataacttcg tataatgtat gctatacgaa    60
gttatcgaac agagaaacta aatccacatt aattgagagt tctatctatt agaaaatgca   120
aactccaact aaatgggaaa acagataacc tcttttattt ttttttaatg tttgatattc   180
gagtcttttt cttttgttag gtttatattc atcatttcaa tgaataaaag aagcttctta   240
ttttggttgc aaagaatgaa aaaaaggat  ttttttcatac ttctaaagct tcaattataa   300
ccaaaaattt tataaatgaa gagaaaaaat ctagtagtat caagttaaac ttagaaaaac   360
tcatcgagca tcaaatgaaa ctgcaattta ttcatatcag gattatcaat accatatttt   420
tgaaaaagcc gtttctgtaa tgaaggagaa aactcaccga ggcagttcca taggatggca   480
agatcctggt atcggtctgc gattccgact cgtccaacat caatacaacc tattaatttc   540
ccctcgtcaa aaataaggtt atcaagtgag aaatcaccat gagtgacgac tgaatccggt   600
gagaatggca aaagcttatg catttctttc cagacttgtt caacaggcca gccattacgc   660
tcgtcatcaa aatcactcgc atcaaccaaa ccgttattca ttcgtgattg cgcctgagcg   720
agacgaaata cgcgatcgct gttaaaagga caattacaaa caggaatcga atgcaaccgg   780
cgcaggaaca ctgccagcgc atcaacaata ttttcacctg aatcaggata ttcttctaat   840
acctggaatg ctgttttgcc ggggatcgca gtggtgagta accatgcatc atcaggagta   900
cggataaaat gcttgatggt cggaagaggc ataaattccg tcagccagtt tagtctgacc   960
atctcatctg taacatcatt ggcaacgcta cctttgccat gtttcagaaa caactctggc  1020
gcatcgggct tcccatacaa tcgatagatt gtcgcacctg attgcccgac attatcgcga  1080
gcccatttat acccatataa atcagcatcc atgttggaat ttaatcgcgg cctcgaaacg  1140
tgagtctttt ccttacccat ctcgagtttt aatgttactt ctcttgcagt tagggaacta  1200
taatgtaact caaataaga  ttaaacaaac taaaataaaa agaagttata cagaaaaacc  1260
catataaacc agtactaatc cataataata atacacaaaa aaactatcaa ataaaaccag  1320
aaaacagatt gaatagaaaa attttttcga tctcctttta tattcaaaat tcgatatatg  1380
aaaaagggaa ctctcagaaa atcaccaaat caatttaatt agatttttct tttccttcta  1440
gcgttggaaa gaaaatttt  tcttttttt  tttagaaatg aaaaatttt  gccgtaggaa  1500
tcaccgtata aaccctgtat aaacgctact ctgttcacct gtgtaggcta tgattgaccc  1560
agtgttcatt gttattgcga gagagcggga gaaagaacc  gatacaagag atccatgctg  1620
gtatagttgt ctgtccaaca cttttgatgaa cttgtaggac gatgatgtgt atttagacga  1680
gtacgtgtgt gactattaag tagttatgat agagaggttt gtacggtgtg ttctgtgtaa  1740
ttcgattgag aaaatggtta tgaatcccta gataacttcg tataatgtat gctatacgaa  1800
gttatcgaa  cattagaata cgtaatccgc aatgcgggga tcctctagag tcgacctgca  1860
ggcatgcaag cttggcgtaa tcatggtcat agctgttttcc tgtgtgaaat tgttatccgc  1920
```

-continued

```
tcacaattcc acacaacata cgagccggaa gcataaagtg taaagcctgg ggtgcctaat    1980
gagtgagcta actcacatta attgcgttgc gctcactgcc cgctttccag tcgggaaacc    2040
tgtcgtgcca gctgcattaa tgaatcggcc aacgcgcggg gagaggcggt ttgcgtattg    2100
ggcgctcttc cgcttcctcg ctcactgact cgctgcgctc ggtcgttcgg ctgcggcgag    2160
cggtatcagc tcactcaaag gcggtaatac ggttatccac agaatcaggg gataacgcag    2220
gaaagaacat gtgagcaaaa ggccagcaaa aggccaggaa ccgtaaaaag gccgcgttgc    2280
tggcgttttt ccataggctc cgcccccctg acgagcatca caaaaatcga cgctcaagtc    2340
agaggtggcg aaacccgaca ggactataaa gataccaggc gtttccccct ggaagctccc    2400
tcgtgcgctc tcctgttccg accctgccgc ttaccggata cctgtccgcc tttctccctt    2460
cgggaagcgt ggcgctttct catagctcac gctgtaggta tctcagttcg gtgtaggtcg    2520
ttcgctccaa gctgggctgt gtgcacgaac cccccgttca gcccgaccgc tgcgccttat    2580
ccggtaacta tcgtcttgag tccaacccgg taagacacga cttatcgcca ctggcagcag    2640
ccactggtaa caggattagc agagcgaggt atgtaggcgg tgctacagag ttcttgaagt    2700
ggtggcctaa ctacggctac actagaagga cagtatttgg tatctgcgct ctgctgaagc    2760
cagttacctt cggaaaaaga gttggtagct cttgatccgg caaacaaacc accgctggta    2820
gcggtggttt ttttgtttgc aagcagcaga ttacgcgcag aaaaaaagga tctcaagaag    2880
atcctttgat cttttctacg gggtctgacg ctcagtggaa cgaaaactca cgttaaggga    2940
ttttggtcat gagattatca aaaaggatct cacctagat ccttttaaat taaaaatgaa     3000
gttttaaatc aatctaaagt atatatgagt aaacttggtc tgacagttac caatgcttaa    3060
tcagtgaggc acctatctca gcgatctgtc tatttcgttc atccatagtt gcctgactcc    3120
ccgtcgtgta gataactacg atacgggagg gcttaccatc tggccccagt gctgcaatga    3180
taccgcgaga cccacgctca ccggctccag atttatcagc aataaaccag ccagccggaa    3240
gggccgagcg cagaagtggt cctgcaactt tatccgcctc catccagtct attaattgtt    3300
gccgggaagc tagagtaagt agttcgccag ttaatagttt gcgcaacgtt gttgccattg    3360
ctacaggcat cgtggtgtca cgctcgtcgt ttggtatggc ttcattcagc tccggttccc    3420
aacgatcaag gcgagttaca tgatccccca tgttgtgcaa aaaagcggtt agctccttcg    3480
gtcctccgat cgttgtcaga agtaagttgg ccgcagtgtt atcactcatg gttatggcag    3540
cactgcataa ttctcttact gtcatgccat ccgtaagatg cttttctgtg actggtgagt    3600
actcaaccaa gtcattctga gaatagtgta tgcggcgacc gagttgctct tgcccggcgt    3660
caatacggga taataccgcg ccacatagca gaactttaaa agtgctcatc attggaaaac    3720
gttcttcggg gcgaaaactc tcaaggatct taccgctgtt gagatccagt tcgatgtaac    3780
ccactcgtgc acccaactga tcttcagcat cttttacttt caccagcgtt tctgggtgag    3840
caaaaacagg aaggcaaaat gccgcaaaaa agggaataag ggcgacacgg aaatgttgaa    3900
tactcatact cttcctttt caatattatt gaagcattta tcagggttat tgtctcatga    3960
gcggatacat atttgaatgt atttagaaaa ataaacaaat aggggttccg cgcacatttc    4020
cccgaaaagt gccacctgac gtctaagaaa ccattattat catgacatta acctataaaa    4080
ataggcgtat cacgaggccc tttcgtctcg cgcgtttcgg tgatgacggt gaaaacctct    4140
gacacatgca gctcccggag acggtcacag cttgtctgta agcggatgcc gggagcagac    4200
aagcccgtca gggcgcgtca gcgggtgttg gcgggtgtcg gggctggctt aactatgcgg    4260
```

| | |
|---|---|
| catcagagca gattgtactg agagtgcacc atatgcggtg tgaaataccg cacagatgcg | 4320 |
| taaggagaaa ataccgcatc aggcgccatt cgccattcag gctgcgcaac tgttgggaag | 4380 |
| ggcgatcggt gcgggcctct tcgctattac gccagctggc gaaaggggga tgtgctgcaa | 4440 |
| ggcgattaag ttgggtaacg ccagggtttt cccagtcacg acgttgtaaa acgacggcca | 4500 |
| gtgaattcga gctcggtac | 4519 |

```
<210> SEQ ID NO 136
<211> LENGTH: 86
<212> TYPE: DNA
<213> ORGANISM: Artificial Sequence
<220> FEATURE:
<223> OTHER INFORMATION: Primer

<400> SEQUENCE: 136
```

| | |
|---|---|
| aggataaaaa aagcttgtga ataaaaatct ttcgctaaaa atcaatataa gaaaatggta | 60 |
| caccttggct aactcgttgt atcatc | 86 |

```
<210> SEQ ID NO 137
<211> LENGTH: 90
<212> TYPE: DNA
<213> ORGANISM: Artificial Sequence
<220> FEATURE:
<223> OTHER INFORMATION: Primer

<400> SEQUENCE: 137
```

| | |
|---|---|
| tgcatacttt atgcgtttat gcgttttgcg ccccttggaa aaaaattgat tctcatcgta | 60 |
| gcattgcgga ttacgtattc taatgttcag | 90 |

```
<210> SEQ ID NO 138
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 138
```

| | |
|---|---|
| ttatgtatgc tcttctgact tttcgtgtga tgaggctcgt ggaaaaaatg aataatttat | 60 |
| gaatttgaga acaattttgt gttgttacgg tattttacta tggaataatc aatcaattga | 120 |
| ggattttatg caaatatcgt ttgaatattt ttccgaccct tgagtacttt tcttcataa | 180 |
| ttgcataata ttgtccgctg ccccttttc tgttagacgg tgtcttgatc tacttgctat | 240 |
| cgttcaacac caccttattt tctaactatt ttttttttag ctcatttgaa tcagcttatg | 300 |
| gtgatggcac attttttgcat aaacctagct gtcctcgttg aacataggaa aaaaaatat | 360 |
| ataaacaagg ctcttttcact ctccttgcaa tcagatttgg gtttgttccc tttattttca | 420 |
| tatttcttgt catattcctt tctcaattat tattttctac tcataacctc acgcaaaata | 480 |
| acacagtcaa atcaatcaaa atgactgaca aaaaaactct taaagactta agaaatcgta | 540 |
| gttctgttta cgattcaatg gttaaatcac ctaatcgtgc tatgttgcgt gcaactggta | 600 |
| tgcaagatga agactttgaa aaacctatcg tcggtgtcat ttcaacttgg gctgaaaaca | 660 |
| caccttgtaa tatccactta catgactttg gtaaactagc caaagtcggt gttaaggaag | 720 |
| ctggtgcttg gccagttcag ttcggaacaa tcacggtttc tgatggaatc gccatgggaa | 780 |
| cccaaggaat gcgtttctcc ttgacatctc gtgatattat tgcagattct attgaagcag | 840 |
| ccatgggagg tcataatgcg gatgcttttg tagccattgg cggtgtgat aaaaacatgc | 900 |
| ccggttctgt tatcgctatg gctaacatgg atatcccagc catttttgct tacggcggaa | 960 |

```
caattgcacc tggtaattta gacggcaaag atatcgattt agtctctgtc tttgaaggtg   1020
tcggccattg gaaccacggc gatatgacca agaagaagt  taaagctttg aatgtaatg    1080 cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct cctaaaaat  ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740 aggtcttta  ttctgaagaa gaagccattg aagctgtctt gaatgatgat attgttgatg   1800
gtgatgttgt tgtcgtacgt tttgtaggac caaagggcgg tcctggtatg cctgaaatgc   1860 tttcccttc  atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattatt                                                 2237
```

<210> SEQ ID NO 139
<211> LENGTH: 4420
<212> TYPE: DNA
<213> ORGANISM: Artificial Sequence
<220> FEATURE:
<223> OTHER INFORMATION: PDC1 A-ilvDSm-BUC cassette

<400> SEQUENCE: 139

```
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt ttcttcataa    180
ttgcataata ttgtccgctg cccctttttc tgttagacgg tgtcttgatc tacttgctat    240
cgttcaacac caccttattt tctaactatt tttttttag  ctcatttgaa tcagcttatg    300
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tatttctac  tcataacctc acgcaaaata    480
acacagtcaa atcaatcaaa atgactgaca aaaaaactct taaagactta agaaatcgta    540 gttctgtttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
```

-continued

```
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc cattttttgct tacggcggaa    960 caattgcacc tggtaattta gacggcaaag atatcgattt agtctctgtc tttgaaggtg    1020
tcggccattg gaaccacggc gatatgacca agaagaagt taaagctttg aatgtaatg    1080 cttgtcccgg tcctggaggc tgcggtggta tgtatactgc taacacaatg gcgacagcta    1140
ttgaagtttt gggacttagc cttccgggtt catcttctca cccggctgaa tccgcagaaa    1200
agaaagcaga tattgaagaa gctggtcgcg ctgttgtcaa aatgctcgaa atgggcttaa    1260
aaccttctga cattttaacg cgtgaagctt ttgaagatgc tattactgta actatggctc    1320
tgggaggttc aaccaactca acccttcacc tcttagctat tgcccatgct gctaatgtgg    1380
aattgacact tgatgatttc aatactttcc aagaaaaagt tcctcatttg gctgatttga    1440
aaccttctgg tcaatatgta ttccaagacc tttacaaggt cggaggggta ccagcagtta    1500
tgaaatatct ccttaaaaat ggcttccttc atggtgaccg tatcacttgt actggcaaaa    1560
cagtcgctga aaatttgaag gcttttgatg atttaacacc tggtcaaaag gttattatgc    1620
cgcttgaaaa tcctaaacgt gaagatggtc cgctcattat tctccatggt aacttggctc    1680
cagacggtgc cgttgccaaa gtttctggtg taaaagtgcg tcgtcatgtc ggtcctgcta    1740
aggtctttaa ttctgaagaa gaagccattg aagctgtctt gaatgatgat attgttgatg    1800
gtgatgttgt tgtcgtacgt tttgtaggac caaagggcgg tcctggtatg cctgaaatgc    1860 tttcccttc atcaatgatt gttggtaaag ggcaaggtga aaaagttgcc cttctgacag    1920
atggccgctt ctcaggtggt acttatggtc ttgtcgtggg tcatatcgct cctgaagcac    1980
aagatggcgg tccaatcgcc tacctgcaaa caggagacat agtcactatt gaccaagaca    2040
ctaaggaatt acactttgat atctccgatg aagagttaaa acatcgtcaa gagaccattg    2100
aattgccacc gctctattca cgcggtatcc ttggtaaata tgctcacatc gtttcgtctg    2160
cttctagggg agccgtaaca gacttttgga agcctgaaga aactggcaaa aaatgagcga    2220
tttaatctct aattattagt taaagtttta taagcatttt tatgtaacga aaaataaatt    2280
ggttcatatt attactgcac tgtcacttac catggaaaga ccagacaaga agttgccgac    2340
agtctgttga attggcctgg ttaggcttaa gtctgggtcc gcttctttac aaatttggag    2400
aatttctctt aaacgatatg tatattcttt tcgttggaaa agatgtcttc caaaaaaaaa    2460
accgatgaat tagtggaacc aaggaaaaaa aaagaggtat ccttgattaa ggaacactgt    2520
ttaaacagtg tggttccaa aaccctgaaa ctgcattagt gtaatagaag actagacacc    2580
tcgatacaaa taatggttac tcaattcaaa actgccagcg aattcgactc tgcaattgct    2640
caagacaagc tagttgtcgt agatttctac gccacttggt gcggtccatg taaaatgatt    2700
gctccaatga ttgaaaaatg tggctgtggt ttcagggtcc ataaagcttt tcaattcatc    2760
tttttttttt ttgttctttt ttttgattcc ggtttctttg aaatttttt gattcggtaa    2820 tctccgagca aaggaagaa cgaaggaagg agcacagact tagattggta tatatacgca    2880
tatgtggtgt tgaagaaaca tgaaattgcc cagtattctt aacccaactg cacagaacaa    2940
aaacctgcag gaaacgaaga taatcatgt cgaaagctac atataaggaa cgtgctgcta    3000
ctcatcctag tcctgttgct gccaagctat ttaatatcat gcacgaaaag caaacaaact    3060
tgtgtgcttc attggatgtt cgtaccacca aggaattact ggagttagtt gaagcattag    3120
```

```
gtcccaaaat tgtttacta aaaacacatg tggatatctt gactgatttt tccatggagg    3180
gcacagttaa gccgctaaag gcattatccg ccaagtacaa tttttactc ttcgaagaca    3240 gaaaatttgc tgacattggt aatacagtca aattgcagta ctctgcgggt gtatacagaa    3300
tagcagaatg ggcagacatt acgaatgcac acggtgtggt gggcccaggt attgttagcg    3360
gtttgaagca ggcggcggaa gaagtaacaa aggaacctag aggcctttg atgttagcag     3420 aattgtcatg caagggctcc ctagctactg gagaatatac taagggtact gttgacattg    3480
cgaagagcga caaagatttt gttatcggct ttattgctca aagagacatg ggtggaagag    3540
atgaaggtta cgattggttg attatgacac ccggtgtggg tttagatgac aagggagacg    3600
cattgggtca acagtataga accgtggatg atgtggtctc tacaggatct gacattatta    3660
ttgttggaag aggactattt gcaaagggaa gggatgctaa ggtagagggt gaacgttaca    3720
gaaaagcagg ctgggaagca tatttgagaa gatgcggcca gcaaaactaa aaaactgtat    3780
tataagtaaa tgcatgtata ctaaactcac aaattagagc ttcaatttaa ttatatcagt    3840
tattacccgg gaatctcggt cgtaatgatt tctataatga cgaaaaaaaa aaaattggaa    3900
agaaaaagct tcatggcctt ccactttccc aaacaacacc tacggtatct ctcaagtctt    3960
atggggttcc attggtttca ccactggtgc taccttgggt gctgctttcg ctgctgaaga    4020
aattgatcca agaagagag ttatcttatt cattggtgac ggttctttgc aattgactgt    4080
tcaagaaatc tccaccatga tcagatgggg cttgaagcca tacttgttcg tcttgaacaa    4140
cgatggttac accattgaaa agttgattca cggtccaaag gctcaataca acgaaattca    4200
aggttgggac cacctatcct tgttgccaac tttcggtgct aaggactatg aaacccacag    4260
agtcgctacc accggtgaat gggacaagtt gacccaagac aagtctttca cgacaactc    4320 taagatcaga atgattgaaa tcatgttgcc agtcttcgat gctccacaaa acttggttga    4380
acaagctaag ttgactgctg ctaccaacgc taagcaataa                         4420

<210> SEQ ID NO 140
<211> LENGTH: 2686
<212> TYPE: DNA
<213> ORGANISM: Artificial Sequence
<220> FEATURE:
<223> OTHER INFORMATION: pUC19

<400> SEQUENCE: 140
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
```

```
gtcgttcggc tgcggcgagc ggtatcagct cactcaaagg cggtaatacg gttatccaca      780
gaatcagggg ataacgcagg aaagaacatg tgagcaaaag gccagcaaaa ggccaggaac      840
cgtaaaaagg ccgcgttgct ggcgtttttc cataggctcc gcccccctga cgagcatcac      900
aaaaatcgac gctcaagtca gaggtggcga acccgacag gactataaag ataccaggcg       960
tttccccctg gaagctccct cgtgcgctct cctgttccga ccctgccgct taccggatac     1020
ctgtccgcct ttctcccttc gggaagcgtg gcgctttctc atagctcacg ctgtaggtat     1080
ctcagttcgg tgtaggtcgt tcgctccaag ctgggctgtg tgcacgaacc ccccgttcag     1140
cccgaccgct gcgccttatc cggtaactat cgtcttgagt ccaacccggt aagacacgac     1200
ttatcgccac tggcagcagc cactggtaac aggattagca gagcgaggta tgtaggcggt     1260
gctacagagt tcttgaagtg gtggcctaac tacggctaca ctagaaggac agtatttggt     1320
atctgcgctc tgctgaagcc agttaccttc ggaaaaagag ttggtagctc ttgatccggc     1380
aaacaaacca ccgctggtag cggtggtttt tttgtttgca agcagcagat tacgcgcaga     1440
aaaaaaggat ctcaagaaga tcctttgatc ttttctacgg ggtctgacgc tcagtggaac     1500
gaaaactcac gttaagggat tttggtcatg agattatcaa aaaggatctt cacctagatc     1560
cttttaaatt aaaaatgaag ttttaaatca atctaaagta tatatgagta aacttggtct     1620
gacagttacc aatgcttaat cagtgaggca cctatctcag cgatctgtct atttcgttca     1680
tccatagttg cctgactccc cgtcgtgtag ataactacga tacgggaggg cttaccatct     1740
ggccccagtg ctgcaatgat accgcgagac ccacgctcac cggctccaga tttatcagca     1800 ataaccagc cagccggaag ggccgagcgc agaagtggtc ctgcaacttt atccgcctcc      1860
atccagtcta ttaattgttg ccgggaagct agagtaagta gttcgccagt taatagtttg     1920
cgcaacgttg ttgccattgc tacaggcatc gtggtgtcac gctcgtcgtt ggtatggct      1980 tcattcagct ccggttccca acgatcaagg cgagttacat gatccccat gttgtgcaaa      2040 aaagcggtta gctccttcgg tcctccgatc gttgtcagaa gtaagttggc cgcagtgtta     2100
tcactcatgg ttatggcagc actgcataat tctcttactg tcatgccatc cgtaagatgc     2160
ttttctgtga ctggtgagta ctcaaccaag tcattctgag aatagtgtat gcggcgaccg     2220
agttgctctt gcccggcgtc aatacgggat aataccgcgc cacatagcag aactttaaaa     2280
gtgctcatca ttggaaaacg ttcttcgggg cgaaaactct caaggatctt accgctgttg     2340
agatccagtt cgatgtaacc cactcgtgca cccaactgat cttcagcatc ttttactttc     2400
accagcgttt ctgggtgagc aaaaacagga aggcaaaatg ccgcaaaaaa gggaataagg     2460
gcgacacgga aatgttgaat actcatactc ttccttttc aatattattg aagcatttat      2520
cagggttatt gtctcatgag cggatacata tttgaatgta tttagaaaaa taaacaaata     2580
ggggttccgc gcacatttcc ccgaaaagtg ccacctgacg tctaagaaac cattattatc     2640
atgacattaa cctataaaaa taggcgtatc acgaggccct ttcgtc                    2686

<210> SEQ ID NO 141
<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 141
aaggaaataa agcaaataac aataacacca ttattttaat ttttttttcta ttactgtcgc      60 taacacctgt atggttgcaa ccaggtgaga atccttctga tgcatacttt atgcgtttat     120
```

```
gcgttttgcg ccccttggaa aaaaattgat tctcatcgta aatgcatact acatgcgttt    180
atgggaaaag cctccatatc caaggtcgc gtttctttta gaaaaactaa tacgtaaacc    240
tgcattaagg taagattata tcagaaaatg tgttgcaaga aatgcattat gcaattttt    300 gattatgaca atctctcgaa agaaatttca tatgatgaga cttgaataat gcagcggcgc    360
ttgctaaaag aacttgtata taagagctgc cattctcgat caatatactg tagtaagtcc    420
tttcctctct ttcttattac acttatttca cataatcaat ctcaaagaga acaacacaat    480
acaataacaa gaagaacaaa atgaaagctc tggtttatca cggtgaccac aagatctcgc    540
ttgaagacaa gcccaagccc acccttcaaa agcccacgga tgtagtagta cgggttttga    600
agaccacgat ctgcggcacg atctcggca tctacaaagg caagaatcca gaggtcgccg    660
acgggcgcat cctgggccat gaaggggtag gcgtcatcga ggaagtgggc gagagtgtca    720
cgcagttcaa gaaaggcgac aaggtcctga tttcctgcgt cacttcttgc ggctcgtgcg    780
actactgcaa gaagcagctt tactcccatt gccgcgacgg cggtggatc ctgggttaca    840 tgatcgatgg cgtgcaggcc gaatacgtcc gcatcccgca tgccgacaac agcctctaca    900
agatccccca gacaattgac gacgaaatcg ccgtcctgct gagcgacatc ctgcccaccg    960
gccacgaaat cggcgtccag tatgggaatg tccagccggg cgatgcggtg gctattgtcg   1020
gcgcgggccc cgtcggcatg tccgtactgt tgaccgccca gttctactcc cctcgacca    1080 tcatcgtgat cgacatggac gagaatcgcc tccagctcgc caaggagctc ggggcaacgc    1140
acaccatcaa ctccggcacg gagaacgttg tcgaagccgt gcataggatt gcggcagagg   1200
gagtcgatgt tgcgatcgag gcggtgggca taccggcgac ttgggacatc tgccaggaga   1260
tcgtcaagcc cggcgcgcac atcgccaacg tcggcgtgca tggcgtcaag gttgacttcg   1320
agattcagaa gctctggatc aagaacctga cgatcaccac gggactggtg aacacgaaca   1380
cgacgcccat gctgatgaag gtcgcctcga ccgacaagct tccgttgaag aagatgatta   1440
cccatcgctt cgagctggcc gagatcgagc acgcctatca ggtattcctc aatggcgcca   1500
aggagaaggc gatgaagatc atcctctcga acgcaggcgc tgcctgagct aattaacata   1560
aaactcatga ttcaacgttt gtgtattttt ttacttttga aggttataga tgtttaggta   1620 ataattggc atagatatag ttttagtata ataaatttct gatttggttt aaaatatcaa    1680 ctatttttt tcacatatgt tcttgtaatt acttttctgt cctgtcttcc aggttaaaga    1740
ttagcttcta atattttagg tggtttatta tttaatttta tgctgattaa tttatttact   1800
tgtttaaacg gccggccaat gtggctgtgg tttcagggtc cataaagctt ttcaattcat    1860 ctttttttt tttgttcttt tttttgattc cggtttcttt gaatttttt tgattcggta    1920 atctccgagc agaaggaaga acgaaggaag gagcacagac ttagattggt atatatacgc   1980
atatgtggtg ttgaagaaac atgaaattgc ccagtattct taacccaact gcacagaaca    2040
aaaacctgca ggaaacgaag ataaatcatg tcgaaagcta catataagga acgtgctgct    2100
actcatccta gtcctgttgc tgccaagcta tttaatatca tgcacgaaaa gcaaacaaac    2160
ttgtgtgctt cattggatgt tcgtaccacc aaggaattac tggagttagt tgaagcatta    2220
ggtcccaaaa tttgtttact aaaaacacat gtggatatct tgactgattt ttccatggag    2280
ggcacagtta agccgctaaa ggcattatcc gccaagtaca atttttttact cttcgaagac    2340 agaaaatttg ctgacattgg taatacagtc aaattgcagt actctgcggg tgtatacaga    2400
atagcagaat gggcagacat tacgaatgca cacggtgtgg tgggcccagg tattgttagc    2460
```

```
ggtttgaagc aggcggcgga agaagtaaca aaggaaccta gaggcctttt gatgttagca    2520
gaattgtcat gcaagggctc cctagctact ggagaatata ctaagggtac tgttgacatt    2580
gcgaagagcg acaaagattt tgttatcggc tttattgctc aaagagacat gggtggaaga    2640
gatgaaggtt acgattggtt gattatgaca cccggtgtgg gtttagatga caagggagac    2700
gcattgggtc aacagtatag aaccgtggat gatgtggtct ctacaggatc tgacattatt    2760
attgttggaa gaggactatt tgcaaaggga agggatgcta aggtagaggg tgaacgttac    2820
agaaaagcag gctgggaagc atatttgaga agatgcggcc agcaaaacta aaaaactgta    2880
ttataagtaa atgcatgtat actaaactca caaattagag cttcaattta attatatcag    2940
ttattacccg ggaatctcgg tcgtaatgat ttctataatg acgaaaaaaa aaaaattgga    3000
aagaaaaagc ttcatggcct tctactttcc aacagatgt atacgctatc gtccaagtct    3060
tgtggggttc cattggtttc acagtcggcg ctctattggg tgctactatg gccgctgaag    3120
aacttgatcc aaagaagaga gttattttat tcattggtga cggttctcta caattgactg    3180
ttcaagaaat ctctaccatg attagatggg gtttgaagcc atacatttt gtcttgaata    3240 acaacggtta caccattgaa aaattgattc acggtcctca tgccgaatat aatgaaattc    3300 aaggtttggga ccacttggcc ttattgccaa cttttggtgc tagaaactac gaaacccaca    3360
gagttgctac cactggtgaa tgggaaaagt tgactcaaga caaggacttc caagacaact    3420
ctaagattag aatgattgaa gttatgttgc agtctttga tgctccacaa aacttggtta    3480
aacaagctca attgactgcc gctactaacg ctaaacaata a    3521
```

<210> SEQ ID NO 142
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 142

```
gtattttggt agattcaatt ctctttccct ttccttttcc ttcgctcccc ttccttatca      60
gcattgcgga ttacgtattc taatgttcag ataacttcgt atagcataca ttatacgaag     120
ttatgcagat tgtactgaga gtgcaccata ccacagcttt tcaattcaat tcatcatttt     180
ttttttattc ttttttttga tttcggtttc tttgaaattt ttttgattcg gtaatctccg     240
aacagaagga agaacgaagg aaggagcaca gacttagatt ggtatatata cgcatatgta     300
gtgttgaaga aacatgaaat tgcccagtat tcttaaccca actgcacaga acaaaaacct     360
gcaggaaacg aagataaatc atgtcgaaag ctacatataa ggaacgtgct gctactcatc     420
ctagtcctgt tgctgccaag ctatttaata tcatgcacga aaagcaaaca aacttgtgtg     480
cttcattgga tgttcgtacc accaaggaat tactggagtt agttgaagca ttaggtccca     540
aaatttgttt actaaaaaca catgtggata tcttgactga ttttccatg gagggcacag     600 ttaagccgct aaaggcatta tccgccaagt acaatttttt actcttcgaa gacagaaaat     660
ttgctgacat tggtaataca gtcaaattgc agtactctgc gggtgtatac agaatagcag     720
aatgggcaga cattacgaat gcacacgtg tggtgggccc aggtattgtt agcggtttga     780
agcaggcggc agaagaagta acaaaggaac ctagaggcct tttgatgtta gcagaattgt     840
catgcaaggg ctccctatct actggagaat atactaaggg tactgttgac attgcgaaga     900
gcgacaaaga ttttgttatc ggctttattg ctcaaagaga catgggtgga agagatgaag     960
gttacgattg gttgattatg acacccggtg tgggtttaga tgacaaggga gacgcattgg    1020
```

| | |
|---|---|
| gtcaacagta tagaaccgtg gatgatgtgg tctctacagg atctgacatt attattgttg | 1080 |
| gaagaggact atttgcaaag ggaagggatg ctaaggtaga gggtgaacgt tacagaaaag | 1140 |
| caggctggga agcatatttg agaagatgcg gccagcaaaa ctaaaaaact gtattataag | 1200 |
| taaatgcatg tatactaaac tcacaaatta gagcttcaat ttaattatat cagttattac | 1260 |
| cctatgcggt gtgaaatacc gcacagatgc gtaaggagaa ataccgcat caggaaattg | 1320 |
| taaacgttaa tattttgtta aaattcgcgt taaattttg ttaaatcagc tcatttttta | 1380 |
| accaataggc cgaaatcggc aaaatccctt ataaatcaaa agaatagacc gagatagggt | 1440 |
| tgagtgttgt tccagtttgg aacaagagtc cactattaaa gaacgtggac tccaacgtca | 1500 |
| aagggcgaaa aaccgtctat cagggcgatg gcccactacg tgaaccatca ccctaatcaa | 1560 |
| gataacttcg tatagcatac attatacgaa gttatccagt gatgatacaa cgagttagcc | 1620 |
| aaggtgacac tctcccccc cctccccctc tgatctttcc tgttgcctct ttttccccca | 1680 |
| accaa | 1685 |

<210> SEQ ID NO 143
<211> LENGTH: 4506
<212> TYPE: DNA
<213> ORGANISM: Artificial Sequence
<220> FEATURE:
<223> OTHER INFORMATION: Sc Hap1 DNA

<400> SEQUENCE: 143

| | |
|---|---|
| atgtcgaata cccttataa ttcatctgtg ccttccattg catccatgac ccagtcttcg | 60 |
| gtctcaagaa gtcctaacat gcatacagca actacgcccg gtgccaacac cagctctaac | 120 |
| tctccaccct tgcacatgtc ttcagattcg tccaagatca agaggaagcg taacagaatt | 180 |
| ccgctcagtt gcaccatttg tcggaaaagg aaagtcaaat gtgacaaact cagaccacac | 240 |
| tgccagcagt gcactaaaac tggggtagcc catctctgcc actacatgga acagacctgg | 300 |
| gcagaagagg cagagaaaga attgctgaag gacaacgaat taaagaagct tagggagcgc | 360 |
| gtaaaatctt tagaaaagac tcttctaag gtgcactctt ctccttcgtc taactccttg | 420 |
| aaaagttaca cactcccga gagcagcaac ctgtttatgg gtagcgatga acacaccacc | 480 |
| cttgttaatg caaatacagg ctctgcttcc tctgcctcgc atatgcatca gcaacaacag | 540 |
| caacagcagc aacaggaaca acaacaagac ttttccagaa gtgcgaacgc caacgcgaat | 600 |
| tcctcgtccc tttctatctc aaataaatat gacaacgatg agctggactt aactaaggac | 660 |
| tttgatcttt tgcatatcaa aagtaacgga accatccact taggtgccac ccactggttg | 720 |
| tctatcatga aggtgaccc gtacctaaaa cttttgtggg gtcatatctt cgctatgagg | 780 |
| gaaaagttaa atgaatggta ctaccaaaaa aattcgtact ctaagctgaa gtcaagcaaa | 840 |
| tgtcccatca atcacgcgca agcgccgcct tctgccgctg ccgccgctac cagaaaatgt | 900 |
| cctgttgatc actccgcgtt ttcgtctggc atggtggccc caaggagga gactcctctt | 960 |
| cctaggaaat gtccagttga ccacaccatg ttctcttcgg gaatgattcc tcccagagag | 1020 |
| gacacttcgt cccagaagag gtgtcccgtt gaccacacca tgtattccgc aggaatgatg | 1080 |
| ccgcccaagg acgagacacc ttccccattt tccactaaag ctatgataga ccataacaag | 1140 |
| catacaatga atccgcctca gtcaaaatgt cctgtggacc atagaaacta tgaaggat | 1200 |
| tatccctctg acatggcaaa ttcttcttcg aacccggcaa gtcgttgccc cattgaccat | 1260 |
| tcaagcatga aaaatacagc ggccttacca gcttcaacgc acaataccat cccacaccac | 1320 |

```
caaccacagt ccggatctca tgctcgttcg catcccgcac aaagcaggaa acatgattcc    1380
tacatgacag aatctgaagt cctcgcaaca ctttgtgaga tgttgccacc aaagcgcgtc    1440
atcgcattat tcatcgagaa attcttcaaa catttatacc ctgccattcc aatcttagat    1500
gaacagaatt tcaaaaatca cgtgaatcaa atgctttcgt tgtcttcgat gaatcccaca    1560
gttaacaact ttggtatgag catgccatct tcatctacac tagagaacca acccataaca    1620
caaatcaatc ttccaaaact ttccgattct tgtaacttag gtattctgat aataatcttg    1680
agattgacat ggctatccat accttctaat tcctgcgaag tcgacctggg agaagaaagt    1740
ggctcatttt tagtgcccaa cgaatctagc aatatgtctg catctgcatt gacctcgatg    1800
gctaaagaag aatcacttct gctaaagcat gagacaccgg tcgaggcact ggagctatgt    1860
caaaaatact tgattaaatt cgatgaactt tctagtattt ccaataacaa cgttaattta    1920
accacggtgc agtttgccat ttttacaac ttctatatga aaagtgcctc taatgatttg    1980
actaccttga caaataccaa caacactggc atggccaatc ctggtcacga ttccgagtct    2040
caccagatcc tattgtccaa tattactcaa atggccttta gttgtgggtt acacagagac    2100
cctgataatt ttcctcaatt aaacgctacc attccagcaa ccagccagga cgtgtctaac    2160
aacgggagca aaaaggcaaa ccctagcacc aatccaactt gaataacaa catgtctgct    2220
gccactacca acagcagtag cagatctggc agtgctgatt caagaagtgg ttctaaccct    2280
gtgaacaaga aggaaaatca ggttagtatc gaaagattta aacacacttg gaggaaaatt    2340
tggtattaca ttgttagcat ggatgttaac caatctcttt ccctggggag ccctcgacta    2400
ctaagaaatc tgagggattt cagcgataca aagctaccaa gtgcgtcaag gattgattat    2460
gttcgcgata tcaaagagtt aatcattgtg aagaatttta ctcttttttt ccaaattgat    2520
ttgtgtatta ttgctgtatt aaatcacatt ttgaatgttt cttttagcaag aagcgtgaga    2580
aaatttgaac tggattcatt gattaattta ttgaaaaatc tgacctatgg tactgagaat    2640
gtcaatgatg tagtgagctc cttgatcaac aaagggttat taccaacttc ggaaggtggt    2700
tctgtagatt caaataatga tgaaatttac ggtctaccga aactacccga tattctaaac    2760
catggtcaac ataaccaaaa cttgtatgct gatggaagaa atacttctag tagtgatata    2820
gataagaaat tggaccttcc tcacgaatct acaacgagag ctctattctt ttccaagcat    2880
atgacaatta gaatgttgct gtacttattg aactacattt tgtttactca ttatgaacca    2940
atgggcagtg aagatcctgg tactaatatc ctagctaagg agtacgctca agaggcatta    3000
aattttgcca tggatggcta cagaaactgc atgattttct tcaacaatat cagaaacacc    3060
aattcactat tcgattacat gaatgttatc ttgtcttacc cttgtttgga cattggacat    3120
cgttctttac aatttatcgt ttgtttgatc ctgagagcta aatgtggccc attgactggt    3180
atgcgtgaat catcgatcat tactaatggt acatcaagtg gatttaatag ttcggtagaa    3240
gatgaggacg tcaaagttaa acaagaatct tctgatgaat tgaaaaaga cgatttcatg    3300
aaagatgtaa atttggattc aggcgattca ttagcagaga ttctaatgtc aagaatgctg    3360
ctatttcaaa aactaacaaa acaactatca agaagtaca actacgctat tcgtatgaac    3420
aaatccactg gattctttgt ctcttttacta gatacacctt caaagaaatc agactcgaaa    3480
tcgggtggta gttcattcat gttgggtaat tggaaacatc caaaggtttc aaacatgagc    3540
ggatttcttg ctggtgacaa agaccaatta cagaaatgcc ccgtgtacca agatgcgctg    3600
gggtttgtta gtccaaccgg tgctaatgaa ggttctgctc cgatgcaagg catgtcctta    3660
cagggctcta ctgctaggat gggagggacc cagttgccac caattagatc atacaaacct    3720
```

```
atcacgtaca caagtagtaa tctacgtcgt atgaatgaaa cgggtgaggc agaagctaag    3780
agaagaagat ttaatgatgg ctatattgat aataatagta acaacgatat acctagagga    3840
atcagcccaa aaccttcaaa tgggctatca tcggtgcagc cactattatc gtcattttcc    3900
atgaaccagc taaacggggg taccattcca acggttccat cgttaaccaa cattacttca    3960
caaatgggag ctttaccatc tttagatagg atcaccacta atcaaataaa tttgccagac    4020
ccatctagag atgaagcatt tgacaactcc atcaagcaaa tgacgcctat gacaagtgca    4080
ttcatgaatg ctaatactac aattccaagt tcaactttaa acgggaatat gaacatgaat    4140
ggagctggaa ctgcgaatac agatacaagt gccaacggca gtgctttatc gacactgaca    4200
agcccacaag gctcagactt agcatccaat tctgctacac agtataaacc tgacttagaa    4260 gacttttga  tgcaaaattc taactttaat gggctaatga taaatccttc cagtctggta    4320
gaagttgttg gtggatacaa cgatcctaat aaccttggaa gaaatgacgc ggttgatttt    4380
ctacccgttg ataatgttga aattgatggt gttggaataa aaatcaacta tcatctacta    4440
actagtattt acgttactag tatattatca tatacggtgt tagaagatga cgcaaatgat    4500
gagaaa                                                              4506
```